(12) United States Patent
Hanigan et al.

(10) Patent No.: US 9,540,337 B2
(45) Date of Patent: Jan. 10, 2017

(54) GAMMA-GLUTAMYL TRANSPEPTIDASE INHIBITORS AND METHODS OF USE

(71) Applicants: The Board of Regents of the University of Oklahoma, Norman, OK (US); Ohio State Innovation Foundation, Columbus, OH (US)

(72) Inventors: Marie H. Hanigan, Edmond, OK (US); Pui Kai Li, Galloway, OH (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 390 days.

(21) Appl. No.: 13/974,704

(22) Filed: Aug. 23, 2013

(65) Prior Publication Data

US 2014/0024685 A1 Jan. 23, 2014

Related U.S. Application Data

(63) Continuation-in-part of application No. 13/428,224, filed on Mar. 23, 2012, now Pat. No. 8,741,937.

(60) Provisional application No. 61/693,137, filed on Aug. 24, 2012.

(51) Int. Cl.
| | | |
|---|---|---|
| *A61K 31/41* | (2006.01) | |
| *A01N 43/82* | (2006.01) | |
| *C07D 285/135* | (2006.01) | |
| *A61K 31/433* | (2006.01) | |

(52) U.S. Cl.
CPC ......... *C07D 285/135* (2013.01); *A61K 31/433* (2013.01)

(58) Field of Classification Search
CPC .......................... A61K 31/433; C07D 285/135
USPC ........................................... 514/363; 548/138
See application file for complete search history.

(56) References Cited

U.S. PATENT DOCUMENTS

| | | | |
|---|---|---|---|
| 5,854,006 A | 12/1998 | Hanigan | |
| 6,617,355 B1 | 9/2003 | Gaston et al. | |
| 7,173,030 B2 * | 2/2007 | Pyring ................. | A61K 31/433 514/236.2 |
| 7,432,301 B2 | 10/2008 | Gaston et al. | |
| 8,741,937 B2 * | 6/2014 | Hanigan ............ | C07D 285/135 514/359 |
| 2005/0009821 A1 | 1/2005 | Pyring et al. | |
| 2007/0066614 A1 | 3/2007 | Pyring et al. | |
| 2010/0197745 A1 | 8/2010 | Hanigan | |
| 2013/0085168 A1 | 4/2013 | Hanigan | |

FOREIGN PATENT DOCUMENTS

| | | |
|---|---|---|
| WO | 9849190 | 11/1998 |
| WO | WO 2004/103980 A1 | 12/2004 |
| WO | WO 2009/100121 A1 | 8/2009 |

OTHER PUBLICATIONS

PCT/US2009/033063, Hanigan, International Search Report and Written Opinion, May 12, 2009.
King et al., "A novel, Species-specific Class of Uncompetitive Inhibitors of (gamma)-Glutamyl Transpeptidase," *J. Bil. Chem. Epub*, (Feb. 2009) vol. 284, No. 14, pp. 9059-9065.
Okada et al., "Crystal structures of Gamma-glutamyltranspeptidase from *Escherichia coli*, a key enzyme in glutathione metabolism, and its reaction intermediate," *Proc. Natl. Acad. Sci. USA*, (Apr. 25, 2006), vol. 103, No. 17, pp. 6471-6476.
Townsend et al., "Inhibition of Gamma-Glutamyl Transpeptidase or Cysteine S-Conjugate Beta-Lyase Activity Blocks the Nephrotoxicity of Cisplatin in Mice," *J. Pharm.Exp. Ther.*, (2002) vol. 300, No. 1, pp. 142-148.
Wickham et al., "Divergent effects of compounds on the hydrolysis and transpeptidation reactions of y-glutamyl transpeptidase," (Jun. 2011), *Journal of Enzyme Inhibition and Medicinal Chem.*, 1-14.
Wickham et al., "Inhibition of human y-glutamyl transpeptidase: development of more potent, physiologically relevant, uncompetitive inhibitors," (2013) *Biochem. J.*, vol. 450, pp. 547-557.
U.S. Appl. No. 12/365,517, Hanigan, Preliminary Amendment filed Sep. 1, 2010.
U.S. Appl. No. 12/365,517, Hanigan, Office Action Restriction, dated May 3, 2011.
U.S. Appl. No. 12/365,517, Hanigan, Response to Office Action Restriction, filed Aug. 22, 2011.
U.S. Appl. No. 12/365,517, Hanigan, Office Action, dated Sep. 23, 2011.
U.S. Appl. No. 12/365,517, Hanigan, Express Abandonment, filed Mar. 23, 2012.
U.S. Appl. No. 13/428,224, Hanigan, Office Action Restriction, dated Apr. 11, 2013.
U.S. Appl. No. 13/428,224 , Hanigan, Office Action, dated Oct. 4, 2013.
U.S. Appl. No. 13/428,224, Hanigan, Response to Office Action, dated Jan. 8, 2014.
Avetisyan, et al.; "Synthesis and hypoglycemic activity of sulfonamide 1, 3, 4 thiadiazoles"; Khimiko-Farmatsevticheskii Zhurnal (1981), vol. 15, No. 6; pp. 69-72 (Abstract).
Wickham, et al.; "Divergent effects of compounds on the hydrolysis and transpeptidation reactions of γ-glutamyl transpeptidase," Journal of Enzyme Inhibition and Medicinal Chem. (Aug. 24, 2011), vol. 27, No. 4, pp. 476-489. DOI:103.3109/14756366.2011.597748. Epub Aug. 24, 2011.

* cited by examiner

*Primary Examiner* — My-Chau T Tran
(74) *Attorney, Agent, or Firm* — Dunlap Codding, P.C.

(57) ABSTRACT

Compositions that are effective in inhibiting gamma-glutamyl transpeptidase are disclosed. Methods of producing and using these compositions are also disclosed.

23 Claims, 10 Drawing Sheets

Formula I

Formula IIA

Formula IIB

GAMMA-GLUTAMYL TRANSPEPTIDASE INHIBITORS AND METHODS OF USE

CROSS-REFERENCE TO RELATED APPLICATIONS/INCORPORATION BY REFERENCE STATEMENT

The present application is a continuation-in-part of U.S. Ser. No. 13/428,224, filed Mar. 23, 2012. The present application also claims the benefit under 35 USC §119(e) of U.S. Provisional Application Ser. No. 61/693,137, filed Aug. 24, 2012. The entirety of each of the above-referenced applications is hereby expressly incorporated herein by reference.

STATEMENT REGARDING FEDERALLY SPONSORED RESEARCH OR DEVELOPMENT

This invention was made with government support under Contract Numbers CA057530 and 1P20GM103640 awarded by the National Institutes of Health (NIH). The government has certain rights in the invention.

BACKGROUND

It is widely known that many chemotherapeutic regimens fail because the side-effects of the drugs used limit the dose that can be administered. This is particularly true of solid tumors. The clinically tolerated doses are often insufficient to kill all of the cells, thereby enriching the tumor population for drug resistant mutants. Among the surviving tumor cells in below-effective treatment regimens are mutant cells that arise spontaneously within the tumor cell population, and are resistant to the treatment drug. Each subsequent round of chemotherapy enriches the population for the resistant cells, which grow and continue to mutate, some to even higher levels of resistance. There is an established linear-log relationship between dose and tumor kill. The higher the dose of the drug, the greater the chance of eradicating the tumor. While methods have been developed to selectively target and kill tumor cells, many of the targeting methods either reduce the effectiveness of the drug, or call for a complex series of reactions to prepare a drug.

In the consideration of solid tumors, it should be recognized that local effective dosage, and systemic dosage, need not be the same. Thus, the only effective portion of the chemotherapeutic agent administered is that which reaches the tumor cell. Many chemotherapeutic agents are administered systemically, however, and only a limited portion (the local dosage) of the dosage administered actually reaches the cell. Thus, dose limitations frequently result in only a fraction of the permitted dosage actually reaching the cell.

The mechanism of inherent and acquired resistance of tumors to many forms of treatment involves glutathione. Elevated glutathione levels in tumors have been shown to contribute to resistance to chemotherapy and radiotherapy and prevent the initiation of the apoptotic cascade in tumor cells. The enzyme gamma-glutamyl transpeptidase (GGT, EC 2.3.2.2, also known as gamma-glutamyl transferase), which is localized to the cell surface, cleaves the γ-glutamyl bond of extracellular glutathione, releasing glutamic acid and cysteinyl-glycine, thus enabling the cell to use extracellular glutathione as a source of cysteine for increased synthesis of intracellular glutathione. GGT is induced in many human tumors, enhancing their resistance to chemotherapy. Inhibiting GGT prior to, during or after chemotherapy or radiation would sensitize GGT-positive tumors to treatment. Inhibiting GGT for as little as 2 hours lowers the intracellular cysteine concentration in GGT-positive tumors. However, all known glutamine analogs that inhibit GGT are too toxic for clinical use in humans at concentrations needed to inhibit GGT activity. Thus, identification of GGT inhibitors which could be used clinically has been a highly desired, yet unmet, need, until the present disclosure.

GGT is a cell surface enzyme that catalyzes the cleavage of the γ-glutamyl bond of glutathione (GSH), GSH-S conjugates, and leukotriene $C_4$ (1, 23, 46). In humans, the expression of GGT is restricted predominantly to the apical surface of ducts and glands where fluids leave the body (2). The highest concentration of GGT is on the apical surface of the proximal tubule cells in the kidney where it prevents excretion of GSH into the urine by cleaving GSH present in the glomerular filtrate (2-3).

Catabolism of GSH by GGT affects intracellular redox levels and cysteine homeostasis [3, 47]. GGT cleavage of GSH S-conjugates alters drug toxicity and inflammation [48-50]. Overexpression of GGT has been implicated in pulmonary disease, cardiovascular disease and cancer [6, 8, 51]. Therefore, development of potent inhibitors of human GGT (hGGT) for clinical use would have broad therapeutic impact.

Aberrant expression and localization of GGT is observed in many disease states including cancer (4). Inhibiting GGT would sensitize tumors to chemotherapy and may be therapeutic in other diseases (5-8). However, GGT inhibitors that have been evaluated clinically are glutamine analogs and are neurotoxic (9-13). The inventors have previously reported the discovery of a novel inhibitor of GGT, referred to herein as OU749 (also referred to herein as Compound 1—see FIG. 6A below), which is not a glutamine analog (14). Inhibitors of hGGT that are considerably less toxic than the glutamine analogs are highly desirable.

GGT can catalyze hydrolysis reaction or a transpeptidation reaction. The first steps in both reactions are the cleavage of the γ-glutamyl bond of the substrate in the enzyme-substrate complex (ES) and the formation of a transient enzyme-glutamyl substrate complex (F-form of the enzyme). As the substrate is cleaved, the γ-glutamyl group forms a transient acyl bond with the enzyme, and the remainder of the substrate is released (15-17). In human GGT, the acyl bond forms between the γ-carbon of the γ-glutamyl substrate and the hydroxyl (beta-oxygen) on the side chain of Thr-381 (18). In the hydrolysis reaction, water hydrolyzes the acyl bond between the γ-glutamyl group and the nucleophilic residue releasing both glutamate and the enzyme (19-20). In the transpeptidation reaction, the γ-glutamyl group is transferred to the amine of an acceptor, thereby forming a new γ-glutamyl compound (21). The transpeptidation reaction occurs by a modified ping-pong mechanism (16, 22). The pH and amino acid concentrations in extracellular fluids where GGT is localized favor the hydrolysis reaction, and previous studies have indicated that the hydrolysis reaction is the predominant reaction catalyzed by GGT in vivo (22-23).

Expression of GGT on the surface of the cell initiates the cleavage of extracellular GSH thereby releasing cysteine and providing an additional source of cysteine for increased intracellular GSH synthesis (5, 37). GSH and free cysteine within the cell are potent reducing agents that protect the cell against oxidative stress and detoxify electrophilic metabolites. Conjugation of many chemotherapy drugs to GSH result in their inactivation, and the conjugates are exported from the cell (38). GSH has been shown to be increased in various cancers including breast (39), lung (40), bone marrow (41), ovarian (42), and head and neck laryngeal (43). Increased intracellular GSH has also been shown to contribute to the inhibition of apoptosis by inducing Bcl-2 and inducing resistance to antihormonal therapy (44-45). Studies have shown that, in mice, GGT-positive tumors are more resistant to treatment with cisplatin than GGT-negative tumors (6). In Phase I clinical trials, acivicin was found to be neurotoxic and cannot be used clinically as an inhibitor of GGT (10-13). Therefore, less toxic inhibitors of GGT are highly desired.

The most commonly used assay for GGT activity monitors the transpeptidation reaction with the synthetic compound L-gamma-glutamyl para-nitroanilide (L-GpNA) as the donor substrate and glycylglycine (GlyGly) as the acceptor. L-GpNA can also serve as a weak acceptor and therefore cannot be used in the absence of GlyGly to measure the hydrolysis reaction. D-gamma-glutamyl para-nitroanalide (D-GpNA), a stereoisomer of L-GpNA, cannot serve as an acceptor and is therefore used as a substrate to measure the hydrolysis reaction [18, 21]. However, the D-isomer of glutamate is not a physiological compound and there have been concerns as to the relevance of D-GpNA as a substrate. OU749 and certain structural analogs thereof are the only known uncompetitive inhibitors of the GGT transpeptidation reaction and the hydrolysis of D-GpNA [14, 53]. Uncompetitive inhibitors bind the gamma-glutamyl intermediate (F-form) of the enzyme. In the transpeptidation reaction, the inhibitors exhibited competitive inhibition with the dipeptide acceptor, GlyGly, indicating that they have a shared or overlapping binding site with GlyGly on the enzyme [14]. The inventors have developed a novel assay (L-Glutamate Release Assay) that monitors GGT hydrolysis of GSH and other physiological substrates [46].

OU749 (Compound 1) was previously identified by high-throughput screening of small molecules as inhibitors of the transpeptidation reaction [14]. Results are provided herein which demonstrate the potency and mechanism by which OU749 and other benzylthiadiazol sulfonamides inhibit GGT activity as measured by the transpeptidation reaction with the synthetic substrate, L-GpNA, the hydrolysis reaction with the synthetic substrate, D-GpNA, and the physiological hydrolysis reaction with GSH as the substrate.

Physicians generally prescribe three main treatments for cancer: surgery, radiation therapy, chemotherapy, or a combination of these. Surgery is generally advisable when physicians can safely remove the cancer from the body. In situations where the cancerous cells have spread, surgeons sometimes must remove large areas of healthy tissue along with the tumor to insure that no malignancy remains. In these cases, physicians may remove lymph nodes from the tumor area because cancer can spread through nodes. However, unfortunately many cancers are discovered too late for surgical cure. In many cases, the patient does not experience symptoms until the cancer has progressed to a malignant stage. Radiation therapy is used to destroy cancer cells. However, radiation can both cause and destroy cancer and can cause damage to surrounding tissues. Side effects of radiation therapy include radiation sickness, which are nausea and skin redness in the tumor area. Reducing the negative side effects of radiation treatment is therefore highly desirable.

Drugs used in chemotherapy take advantage of cancer cells' rapid growth and consumption of large amounts of nutrients. Side effects of chemotherapy can include nausea and temporary full or partial hair loss. Antimetabolites, one group of these drugs, work by mimicking the nutrients the body's cells consume. Physicians inject these drugs into the bloodstream, where they travel throughout the body, consumed by every cell. Rapidly growing cancerous cells consume much more of the poisonous drugs than do normal cells. As a result, the drugs destroy cancerous cells faster than normal cells. Another group of chemotherapy drugs interferes with the duplication of DNA (cells reproduce by duplicating their genetic code, or DNA), so cells cannot reproduce. Chemotherapy can also be directed against mutated proteins in the tumor cells, overexpressed proteins or other properties of the tumor cell. However, chemotherapy drugs may act on both the cancerous cells and the healthy cells. A physician's challenge is to administer the drugs so that only the cancer cells, and not the healthy cells, are killed. Side effects such as those described above prevent the long term or recurrent use of these drugs. Furthermore, there are an increasing number of effective drugs that can no longer be used due to resistance by the causative agent. It is thus highly desirable to reduce the side effects of therapeutics while maintaining the cancer-reducing qualities thereof, thus enabling: (a) longer term usage of the therapeutics, (b) usage of higher dosages of the therapeutics, or (c) enhancement of the therapeutics' effects so that lower dosages thereof may be utilized in treatment protocols.

DETAILED DESCRIPTION

Figure 1:
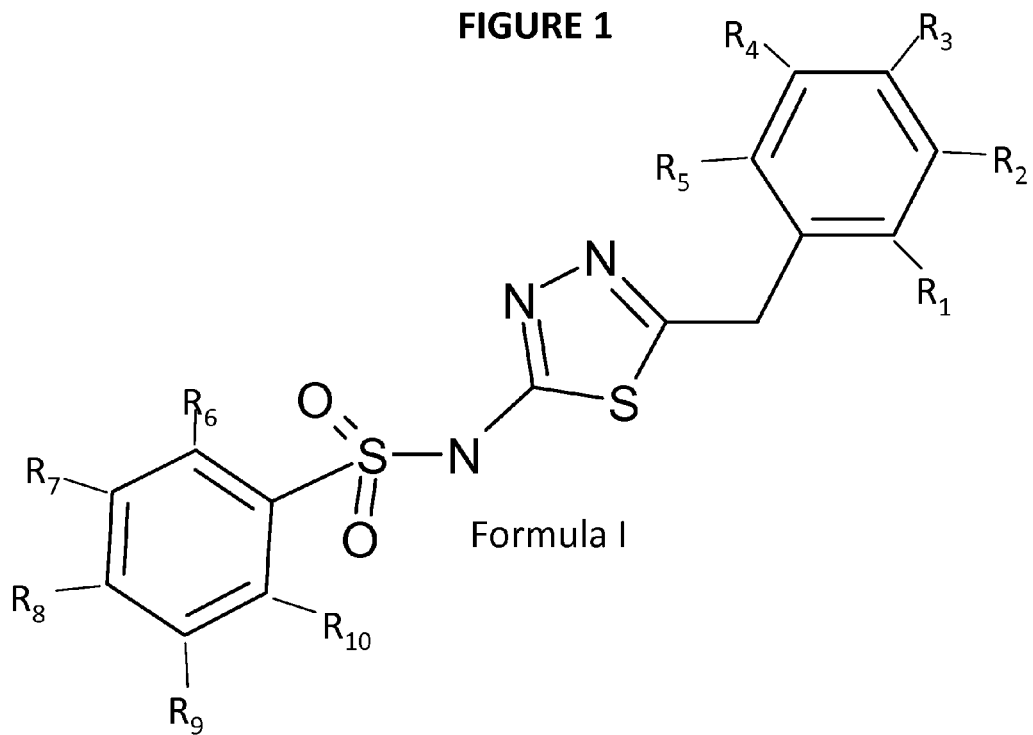
FIG. 1 illustrates Formula I, the base structure of several embodiments of GGT inhibitory compounds of the presently disclosed inventive concept(s).

Before explaining at least one embodiment of the presently disclosed and claimed inventive concept(s) in detail by way of exemplary description, drawings, experimentation, results, and laboratory procedures, it is to be understood that the inventive concept(s) is not limited in its application to the details of construction and the arrangement of the compositions, formulations, or components set forth in the following description or illustrated in the drawings, examples, experiments, and/or results. The presently disclosed and claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting except where indicated as such.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference. In particular, but not by way of limitation, the entire contents of U.S. Ser. Nos. 61/063,525; 61/693,137; 12/365,517; and 13/428,224 are expressly incorporated herein by reference.

All of the compositions and/or methods disclosed and claimed herein can be made and executed without undue experimentation in light of the present disclosure. While the compositions and methods of this presently disclosed and claimed inventive concept(s) have been described in terms of particular embodiments, it will be apparent to those of skill in the art that variations may be applied to the chemical compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation or error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent, or one-half percent. The term "substantially" will be understood to allow for minor variations and/or deviations that do not result in a significant impact thereto.

The use of the term "at least one" will be understood to include one as well as any quantity more than one, including but not limited to, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more. The term "at least one" may extend up to 500 or 1000 or more, depending on the term to which it is attached; in addition, the quantities of 500/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the term "carcinomas" refers to lesions that are cancerous. Non-limiting examples include malignant melanomas, breast cancer, and colon cancer. As used herein, the term "neoplasm" refers to both precancerous and cancerous lesions.

As used herein, the terms "inhibit" or "inhibiting," mean decreasing or reducing GGT activity and does not necessarily mean a complete cessation of GGT activity. In reference to tumor cell growth rate, the terms "inhibit" or "inhibiting" mean decreasing or reducing tumor cell growth rate from the rate that would occur without treatment of the GGT inhibitor and/or causing tumor mass to decrease. Inhibiting also includes causing a complete regression of the tumor. Thus the compounds of the presently disclosed inventive concept(s) can be either cytostatic or cytotoxic to the tumor cells, when used alone or in combination with other therapies.

As used herein, the terms "subject" and "patient" are used interchangeably. Subjects and patients are mammals, including but not limited to humans, primates, monkeys, cats, dogs, rabbits, mice, rats, guinea pigs, horses, cows, sheep, goats, pigs, llamas, zoo animals and grazing animals.

As defined herein, the term "treating cancer" (i.e., with an anticancer therapy) in a patient includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as, but not limited to, tissue or serum components).

As used herein, the terms "cytotoxic agent", "chemotherapeutic agent", "anticancer agent", and "antitumor agent" are used interchangeably herein and refer to agents that have the property of inhibiting the growth or proliferation of hyperproliferative cells (e.g., a cytostatic agent), or inducing the killing of hyperproliferative cells.

As used herein, a "therapeutically effective amount" of the GGT inhibitor and/or chemotherapeutic agent of the presently disclosed inventive concept(s) refers to an amount of a compound that is effective, upon single-dose or multiple-dose administration to the subject (e.g., a patient), at enhancing the inhibition of the growth or proliferation of hyperproliferative cells (e.g., cancer cells), or inducing the killing of hyperproliferative cells, by a chemotherapeutic compound and/or by radiation treatment. The term "therapeutically effective amount" may also refer to an amount of a GGT inhibitory compound that is co-administered (i.e., sequentially or concomitantly) with one or more cytotoxic agents such that the GGT inhibitory compound and the cytotoxic agent are effective, upon single- or multiple-dose administration to the subject (e.g., a patient), at inhibiting the growth or proliferation of hyperproliferative cells or inducing the killing of hyperproliferative cells. Such growth inhibition or killing can be reflected as a prolongation of the survival of the subject (e.g., a patient) beyond that expected in the absence of such treatment, or any improvement in the prognosis of the subject relative to the absence of such treatment.

As used herein, the term "pharmaceutically acceptable" refers to those properties and/or substances which are acceptable to the patient from a pharmacological/toxicological point of view, including bioavailability and patient acceptance, or are acceptable to the manufacturing chemist from a physical-chemical point of view regarding composition, formulation, stability, and isolatability thereof.

The terms "chemosensitization" and "chemosensitizing effect" are used interchangeably herein and refer to the enhancement of radiation and/or chemotherapy efficacy by the compound. "Chemosensitizer" refers to the agent that enhances the efficacy of another agent, such as the cytotoxic agent and/or radiation.

The terms "a compound for increasing sensitivity to an anticancer drug," "a compound for enhancing sensitivity to an anticancer drug," "a compound for increasing and/or enhancing sensitivity to an anticancer drug," "a compound for overcoming a resistance to an anticancer drug," "an anticancer-drug-resistance overcoming compound," "a pharmaceutical composition for increasing and/or enhancing sensitivity to an anticancer drug," "a pharmaceutical composition for overcoming a resistance to an anticancer drug," and "an anticancer-drug-resistance overcoming pharmaceutical composition" refer to a compound (or a pharmaceutical composition containing the compound) which has no carcinostatic activity itself, but which functions to reduce the resistance of cancer cells to an anticancer drug. In other words, the compound increases and/or enhances the anticancer drug sensitivity level of cancer cells that have an acquired resistance to the anticancer drug. The compound may increase and/or enhance the anticancer drug sensitivity level of the anticancer-drug-resistant cells to a level that is approximately equal to the anticancer agent sensitivity level of anticancer-drug-sensitive cells; optionally, the compound may increase and/or enhance the anticancer drug sensitivity level of the anticancer-drug-resistant cells to a level that is higher than the anticancer agent sensitivity level of anticancer-drug-sensitive cells. Further, other term equivalents to those utilized herein above include "restraining or inhibiting resistance", "releasing resistance", "releasing tolerance", and the like.

The terms "a compound for enhancing an effect of an anticancer drug," "an anticancer-drug-effect enhancing compound," "a pharmaceutical composition for enhancing an effect of an anticancer drug," and "an anticancer-drug effect enhancing pharmaceutical composition" refer to a compound (or a pharmaceutical composition containing the compound) which has no carcinostatic activity itself but which enhances an activity of an anticancer drug or therapy (i.e., a carcinostatic effect of an anticancer drug itself) by administering it together with or apart from the anticancer drug. In this case, the terms "enhancing" and "increasing" mean not only to increase an anticancer drug's effect level on anticancer-drug resistant cells to a level that is approximately equal to or higher than that the drug's effect level on anticancer-drug sensitive cells, but also to increase a sensitivity level of cancer cells that have not acquired any resistance to the anticancer drug.

Therefore, by using the anticancer-drug-resistance overcoming compound or the anticancer-drug-effect enhancing compound according to the methods of the presently described inventive concept(s), a sensitivity of cancer cells having an acquired resistance to an anticancer drug can be increased. The increased sensitivity will allow for a reduction in the dosage of the anticancer drug and/or an extension in the intervals between administrations of the anticancer drug.

The term "a method for overcoming a resistance to an anticancer drug" as used herein refers to a method for reducing a resistance of cancer cells to an anticancer drug, such as but not limited to, a method for increasing an anticancer drug sensitivity level in cancer cells that have acquired a resistance to an anticancer drug.

The phrase "a method for enhancing and/or increasing an effect of an anticancer drug" as used herein refers to a method for enhancing and/or increasing an anticancer drug's activity, such as but not limited to, a method for enhancing and/or increasing a carcinostatic effect of an anticancer drug itself.

The phrase "administering together with" as used herein refers to a protocol that involves the administration of two kinds of drugs/compounds. The phrase covers protocols in which the two kinds of drugs/compounds are administered simultaneously as well as sequentially (or a combination thereof). When administered simultaneously, the two kinds of drugs/compounds may be administered as a mixture or as separate drugs/compounds. When administered separately (whether simultaneously or sequentially), the administration routes of the two kinds of drugs/compounds may be the same or different. In addition, each of the two kinds of drugs/compounds may be administered continuously and/or at intervals.

Turning now to the presently disclosed and claimed inventive concept(s), benzylthiadiazol benzenesulfonamide and benzylthiadiazol naphthylsulfonamide compounds having anti-GGT inhibitory activity are disclosed herein. These compounds, as well as compositions containing same, methods of production of the compounds/compositions, and methods that utilize the compounds/compositions, are encompassed within the scope of the presently disclosed and claimed inventive concept(s).

In certain embodiments, the benzylthiadiazol benzenesulfonamide compounds are represented by the general structure of Formula I (FIG. 1), wherein any one of $R_1$-$R_{10}$ may be H, Cl, F, Br, I, OH, an alkoxy, $NO_2$, an alkyl, $C(CH_3)_3$, NHOH, $NH_2$, or $N(CH_3)_2$; optionally, any two or more of $R_1$-$R_{10}$ may be any combination of H, Cl, F, Br, I, OH, an alkoxy, $NO_2$, an alkyl, $C(CH_3)_3$, NHOH, $NH_2$, or $N(CH_3)_2$. Other R groups include, but are not limited to, carrier groups linked by C, N, or O.

Figure 2:
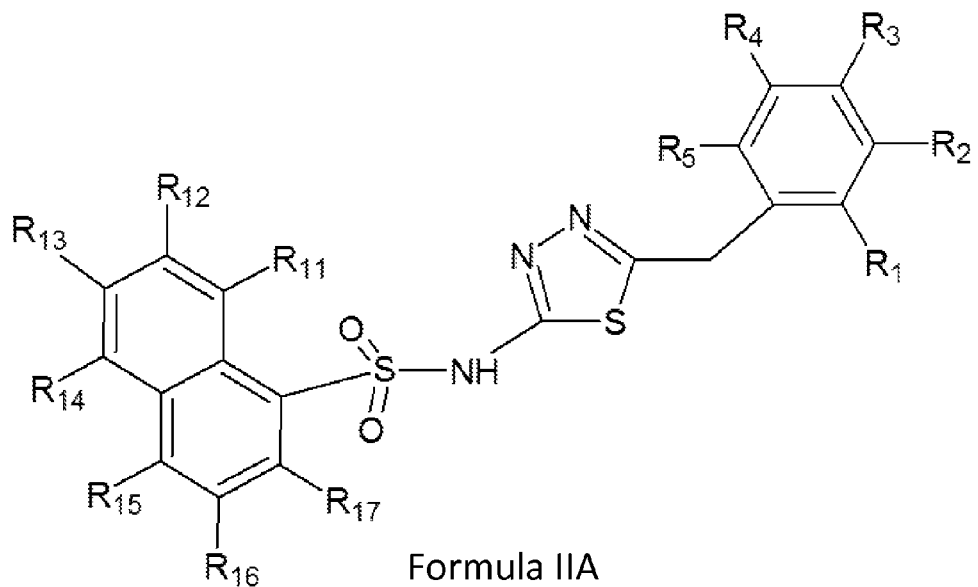
FIG. 2 illustrates Formula IIA, the base structure of alternate embodiments of GGT inhibitory compounds of the presently disclosed inventive concept(s).
Figure 3:
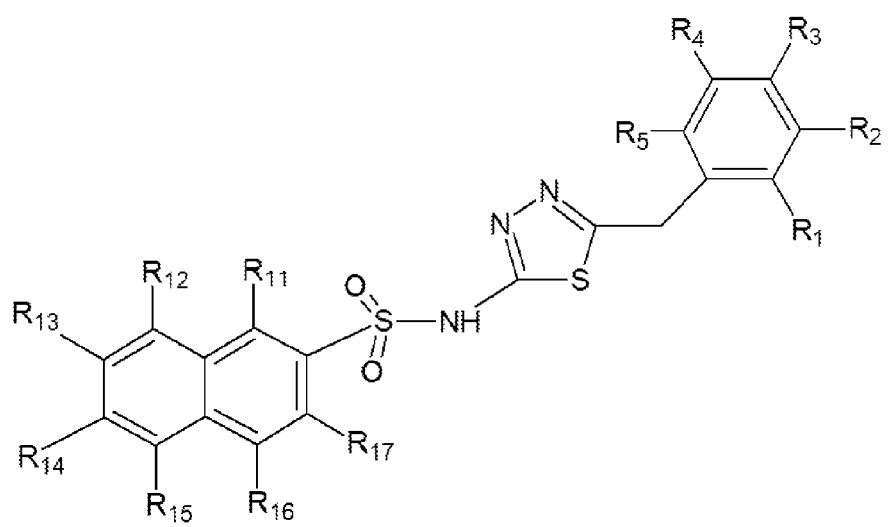
FIG. 3 illustrates Formula IIB, the base structure of alternate embodiments of GGT inhibitory compounds of the presently disclosed inventive concept(s).

In certain other embodiments, the benzylthiadiazol naphthylsulfonamide compounds are represented by the general structures of Formula IIA (FIG. 2) and Formula IIB (FIG. 3), wherein any one of $R_1$-$R_5$ and $R_{11}$-$R_{17}$ may be H, Cl, F, Br, I, OH, an alkoxy, $NO_2$, an alkyl, $C(CH_3)_3$, NHOH, $NH_2$, or $N(CH_3)_2$; optionally, any two or more of $R_1$-$R_5$ and $R_{11}$-$R_{17}$ may be any combination of H, Cl, F, Br, I, OH, an alkoxy, $NO_2$, an alkyl, $C(CH_3)_3$, NHOH, $NH_2$, or $N(CH_3)_2$. Other R groups include, but are not limited to, carrier groups linked by C, N, or O. Further, in the compounds of either Formula IIA or Formula IIB, one or more of adjacent pairs $R_{11}$ and $R_{12}$, $R_{12}$ and $R_{13}$, $R_{13}$ and $R_{14}$, $R_{15}$ and $R_{16}$, and $R_{16}$ and $R_{17}$ may comprise a benzene ring. For example but not by way of limitation, a benzene ring between the adjacent pair $R_{12}$ and $R_{13}$ of Formula IIA would transform the 1-naphthylsulfonamide moiety into an anthracenesulfonamide moiety. In an alternative non-limiting example, a benzene ring between the adjacent pair $R_{13}$ and $R_{14}$ of Formula IIB would transform the 2-naphthylsulfonamide moiety into an anthracenesulfonamide moiety.

In particular non-limiting embodiments, the benzylthiadiazol naphthylsulfonamide compounds are represented by the general structure of Formula IIA (FIG. 2), wherein $R_1$-$R_5$ and $R_{11}$-$R_{17}$ are the same or different from each other, and wherein each of $R_1$-$R_5$ and $R_{11}$-$R_{17}$ represent H, Cl, F, Br, I, OH, an alkoxy, or $NO_2$. When the structure of Formula IIA contains an alkoxy, the alkoxy may be selected from the group consisting of methoxy, ethoxy, n-propoxy, iso-propoxy, n-butoxy, tert-butoxy, sec-butoxy, pentoxy, hexoxy, octoxy, nonoxy, decoxy, undecoxy, and dodecoxy. In one non-limiting example, at least one of $R_1$-$R_5$ and $R_{11}$-$R_{17}$ of Formula IIA is Cl. In another non-limiting example, at least one of $R_1$-$R_5$ and $R_{11}$-$R_{17}$ of Formula IIA is an alkoxy group, such as a methoxy group or an ethoxy group. In another non-limiting example, $R_3$ of Formula IIA is an alkoxy group (such as a methoxy group), and each of $R_1$, $R_2$, $R_4$, $R_5$, and $R_{11}$-$R_{17}$ is H. In yet another non-limiting example, $R_3$ of Formula IIA is an alkoxy group (such as a methoxy group), and at least one of $R_1$, $R_2$, $R_4$, $R_5$, and $R_{11}$-$R_{17}$ is Cl. In a further non-limiting example, at least one of $R_1$-$R_5$ of Formula IIA is a methoxy group.

The compounds may be used as antitumor agent effect enhancers that assist and/or enhance the effects of antitumor agents and/or increase the sensitivity of therapy-resistant tumor cells to the antitumor agents, such as chemotherapeutic agents and/or radiation therapies. For example, in one non-limiting embodiment, the compounds of the presently disclosed inventive concept(s) may cause their effect by inhibiting GGT activity such that the chemotherapeutic agents are not conjugated to GSH, thereby maintaining the therapeutic effects of the chemotherapeutic agents. The compounds may thus be used in methods for enhancing the inhibition and/or killing of neoplastic (cancer) cells, for example for the treatment, inhibition, reduction in the occurrence of, and/or prevention of tumors, malignant growths, and/or other neoplasias in a subject in need of such therapy. The compounds can also be used in methods for the prophylaxis and/or treatment of a reversible airways obstruction in a subject in need of such therapy. Non-limiting examples of reversible airways obstructions include asthma, chronic obstructive pulmonary disease (COPD), an allergic reaction, a respiratory tract infection, and upper respiratory tract disease. The compounds cause their effect in the treatment of cancers, reversible airways obstructions, and other conditions by inhibiting GGT. For example, the efficacy of the anticancer therapy is enhanced by reducing resistance to the drug and/or therapy and sensitizing the tumor cells to apoptosis, thereby enabling usage of a higher dosage of the anticancer therapy, and/or by reducing the toxicity of the anticancer therapy. Other embodiments of the presently disclosed inventive concept(s) will become apparent upon review of the present description; thus the presently disclosed inventive concept(s) are not to be construed as limited to those hereby summarized.

Expression of gamma-glutamyl transpeptidase (GGT, EC 2.3.2.2, also known as gamma-glutamyl transferase) in neoplastic tumors contributes to resistance of tumors to radiation and chemotherapy. GGT has numerous roles in the body, including enabling cells to use extracellular glutathione as a source of additional cysteine. The inhibitors of GGT activity described or otherwise contemplated herein can be used prior to (or with) the administration of chemotherapy to limit the supply of cysteine to the tumor, thereby blocking the tumor's ability to maintain high levels of intracellular glutathione.

The benzylthiadiazol benzenesulfonamide and benzylthiadiazol naphthylsulfonamide compounds of the presently disclosed inventive concept(s) constitute a novel class of inhibitors of GGT that are structurally distinct from and less toxic than the glutamine analog inhibitors of GGT. This new class of compounds occupies the acceptor site, not the γ-glutamyl site.

The benzylthiadiazol benzenesulfonamide and benzylthiadiazol naphthylsulfonamide compounds of the presently disclosed inventive concept(s) will be understood to include stereoisomers and salts of the compounds described hereinabove. Thus, when reference is made herein to compounds represented by Formulas I, IIA, and/or IIB, it is intended that the compounds also include pharmaceutically acceptable salts of the compounds represented by Formulas I, IIA, and/or IIB. Examples of various embodiments of the compounds represented by Formulas I and IIA include, but are not limited to, the examples shown in Tables 2, 3, 4, 5, 6, and 7, as further discussed below.

Where used herein, the term "alkyl" means a monovalent linear or branched saturated hydrocarbon moiety, consisting solely of carbon and hydrogen atoms and having 1, 2, 3, 4, 5, 6, 7, 8, 9, 10, 11, or 12 carbon atoms. "Lower alkyl" refers to an alkyl group of one to six carbons. Examples of alkyl groups include, but are not limited to, methyl, ethyl propyl, isopropyl, isobutyl, sec-butyl, tert-butyl, pentyl, n-hexyl, octyl, nonyl, and dodecyl, and the like.

Where used herein, the term "alkoxy" means a lower alkoxy group, methoxy, ethoxy, propoxy (including n-propoxy and iso-propoxy), butoxy (including n-butoxy, tert-butoxy, and sec-butoxy), a pentoxy, a hexoxy, an octoxy, a nonoxy, a decoxy, a undecoxy, a dodecoxy, and heterogeneous alkoxys which comprise, for example, two or more different alkyl groups, in a configuration such as 1,2-dimethylbutoxy. The term "lower alkoxy group" includes straight or branched chain alkoxy group with one to six carbon atoms, such as methoxy, ethoxy, propoxy, iso-propoxy, butoxy, tert-butoxy, pentoxy, tert-pentoxy, or hexoxy group, and more particularly, methoxy, ethoxy, propoxy, or isopropoxy group of one to three carbon atoms.

Salts of the presently described benzylthiadiazol benzenesulfonamide and benzylthiadiazol naphthylsulfonamide compounds include, but are not limited to, those formed with both organic acids or bases and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, benzenesulphonic, naphthalenesulphonic or naphthalenedisulphonic), salicylic, glutaric, gluconic, tricarballylic, cinnamic, substituted cinnamic (for example, phenyl, methyl, methoxy, or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Another embodiment of the presently disclosed and claimed inventive concept(s) includes a pharmaceutical composition that comprises at least one of any of the GGT inhibitory compounds disclosed or otherwise contemplated herein in combination with a pharmaceutically acceptable additive, diluent, carrier, and/or excipient (such as, but not limited to, phosphate buffered saline (PBS)). The pharmaceutical composition comprising the GGT inhibitor may further comprise a quantity of glutathione for acting as a substrate for endogenous GGT protein acted on by the GGT inhibitors of the presently disclosed and claimed inventive concept(s); optionally, the glutathione may be provided and/or administered separately in the methods described in greater detail herein below. Also, the GGT inhibitory compounds of the presently disclosed inventive concept(s) may be connected to a molecule to enhance the physiological half-life of the inhibitor; non-limiting examples of molecules that may be utilized in this fashion include polyethylene glycol (PEG), "miniPEG", or a carrier protein such as a serum albumin (for example, via carboxymethylcellulose).

One embodiment of the presently disclosed and claimed inventive concept(s) is directed to a method of treating cancer in which an effective amount of radiation and/or a chemotherapeutic agent is administered to a patient in need of a cancer treatment. The method also includes the administration to a patient of a therapeutically effective amount of any of the benzylthiadiazol benzenesulfonamide or benzylthiadiazol naphthylsulfonamide compounds or compound-containing compositions described herein above or otherwise contemplated herein (including but not limited to, at least one GGT inhibitory compound represented by Formula I, IIA, and/or IIB or a pharmaceutically acceptable salt thereof, or a pharmaceutical composition containing same), wherein said compound has anti-GGT inhibitory activity.

In another embodiment, the presently disclosed inventive concept(s) is directed to a method for the prophylaxis and/or treatment of a reversible airways obstruction in a subject. A therapeutically effective amount of any of the benzylthiadiazol benzenesulfonamide or benzylthiadiazol naphthylsulfonamide compounds or compound-containing compositions described herein above or otherwise contemplated herein (including but not limited to, at least one GGT inhibitor represented by Formula I, IIA, and/or IIB or a pharmaceutically acceptable salt thereof, or a pharmaceutical composition containing same) is administered to the subject, wherein the compound has anti-GGT inhibitory activity. Other conditions and/or diseases which may be treated with the GGT inhibitory compounds described or otherwise contemplated herein include, but are not limited to, renal and liver diseases, cardiovascular disease, inner ear diseases and conditions, and degenerative diseases, as described in further detail below. In one embodiment, the compounds of the presently disclosed inventive concept(s) cause their effect by inhibiting GGT activity such that the chemotherapeutic agents are not conjugated to GSH, thereby maintaining the therapeutic effects of the chemotherapeutic agents.

In one embodiment, the presently disclosed inventive concept(s) includes a method of enhancing the efficacy of an anticancer therapy in a subject having a cancer. In the method, any of the benzylthiadiazol benzenesulfonamide or benzylthiadiazol naphthylsulfonamide compounds or compound-containing compositions described herein above or otherwise contemplated herein (including but not limited to, at least one GGT inhibitor represented by Formula I, IIA, and/or IIB or a pharmaceutically acceptable salt thereof, or a pharmaceutical composition containing same) is administered to the subject, and at least one anticancer therapy (chemotherapy and/or radiation therapy) is also administered to the subject, wherein the efficacy of the at least one anticancer therapy is enhanced. Enhancement of the at least one anticancer therapy's efficacy may enable usage of a higher dosage of the anticancer therapy and/or reduce the toxicity of the anticancer therapy.

Certain embodiments of the methods of the presently disclosed inventive concept(s) involve the administration of one or more GGT inhibitory compounds or compound-containing compositions as described or otherwise contemplated herein to a subject in need of such therapy, such as but not limited to, a subject having a susceptible cancer (i.e., a malignant cell population or tumor which expresses extracellular GGT). Compounds used in the presently disclosed inventive concept(s) are effective on tumor cell lines in vitro as well as on human tumors in vivo, and the compounds may be particularly useful for the treatment of solid tumors for which relatively few treatments are available. Non-limiting examples of such solid tumors include epidermoid and myeloid tumors, acute or chronic, nonsmall cell, and squamous cell carcinomas. Specific cancers which are susceptible to treatment by administration of the presently disclosed compounds include, but are not limited to, prostate cancer, colon cancer, small cell lung cancer, large cell lung cancer, lung adenocarcinoma, epidermoid lung cancer, melanoma (including amelanotic subtypes), renal cell carcinoma, gastric carcinoma, cancers of the central nervous system, including brain tumors, neuroblastomas, gastric carcinoma, breast cancer, ovarian cancer, testicular cancer, lymphoma and leukemia, esophageal cancer, stomach cancer, liver cancers, cervical cancer, head and neck cancers, adrenal cancer, oral or mucosal cancer, bladder cancer, pancreatic cancer, lymphoma, Hodgkins disease, and sarcomas, hematopoeitic cell cancers such as B cell leukemia/lymphomas, myelomas, T-cell leukemias/lymphomas, small cell leukemias/lymphomas, null cell, sezary, monocytic, myelomonocytic and Hairy cell leukemias. These lymphomas/leukemias can be either acute or chronic.

The presently disclosed inventive concept(s) also include the use of pharmaceutical compositions which comprise one or more of the GGT inhibitory compounds disclosed or otherwise contemplated herein (including pharmaceutically acceptable salts, derivatives, metabolites, analogues, and/or mimics thereof) in combination with one or more pharmaceutically acceptable additives, diluents, carriers, and/or excipients for the manufacture of a medicament for a cancerous condition. As noted, the pharmaceutical formulations may be administered in combination (before and/or simultaneously) with other therapeutic treatments, such as but not limited to, radiation treatment and/or chemotherapeutic drugs. While it is possible for the compound of the presently disclosed inventive concept(s) thereof to be administered alone, in one particular embodiment, the compound is presented as part of a pharmaceutical formulation. Accordingly, the presently disclosed inventive concept(s) further provides a pharmaceutical formulation comprising at least one compound described herein as represented by Formula I, IIA, and/or IIB, including pharmaceutically acceptable salts thereof, and at least one pharmaceutically acceptable carrier or excipient; in addition, the pharmaceutical formulation may optionally include one or more other therapeutic ingredients used for the treatment of a condition described herein.

In one embodiment, the pharmaceutical formulations of the presently disclosed inventive concept(s) further include one or more conventional chemotherapeutic agents. Particular non-limiting examples of chemotherapeutic agents that may be disposed in a pharmaceutical composition in combination with the GGT inhibitory compounds described or otherwise contemplated herein include melphalan, doxorubicin, methotrexate, taxol, vincristine, 6-mercaptopurine, cytosine arabinoside, carboplatin, cisplatin, codetaxel, 5-fluorouracil, cyclophosphamide, and erlotinib. In particular, platinum agents and alkylating agents are contemplated. In alternative embodiments, the one or more conventional chemotherapeutic agents may be selected from the group comprising flutamide and luprolide; antiestrogens such as tamoxifen; antimetabolites; cytotoxic agents such as daunorubicin, fluorouracil, floxuridine, hexamethylmelamine, interferon alpha, methotrexate, plicamycin, mercaptopurine, thinguanine, adramycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, streptozocin, bleomycin, dactinomycin and idamycin; hormones such as medroxyprogesterone, ethinyl estradiol, estradiol, leuprolide, megestrol, octreotide, diethylstilbestrol, chlorotrianisene, etoposide, podophyllotoxin, and goserelin; nitrogen mustard derivatives such as chlorambucil, methlorethamine, and thiotepa; steroids such as betamethasone; and other antineoplastic agents such as live *Mycobacterium bovis*, dicarbazine, asparaginase, leucovoribn, mitotane, vincristine, vinblastine, texotere, and cyclophosphamide. Other chemotherapeutic agents that may be utilized in accordance with the presently disclosed and claimed inventive concept(s) include, but are not limited to, adriamycin, aclarubicin; acodazole hydrochloride; acrqnine; adozelesin; aldesleukin; ambomycin; ametantrone acetate; aminoglutethimide; amsacrine; anastrozole; anthremycin; asperlin; azacitidine; azetepa; azotomycin; abiraterone; acylfulvene; adecypenol; All-TK antagonists; ambamustine; amidox; arnifostine; aminolevulinic acid; amrubicin; anagrelide; andrographolide; angiogenesis inhibitors; antagonist D; antagonist G; antarelix; anti-dorsalizing morphogenetic protein-1; antiandrogen, antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2: axinastatin 3; azasetron; azatoxin: azatyrosine; batimastat; benzodepa; bicalutamide; bisantrene hydrochloride; bisnafide dimesylate; bizelesin; bleomycin sulfate; brequinar sodium; bropirimine; busulfan; baccatin III derivatives; balanol; BCR/ABL antagonists; benzochlorins; benzoyllaurosporine; beta lactam derivatives; beta-alethine; betaclamycin B; betulinic acid; bFGF inhibitor; bisaziridinylspermine; bistratene A; breflate; budotitane; buthionine sulfoximine; bromineepiandrosterone; cactinomycin; calusterone; carecemide; carbetimer; carubicin hydrochloride; carzelesin; cedefingol; cirolemycin; cisplatin; cladribine; crisnatol mesylate; calcipotriol; calphostin C; camptothecin derivatives; canarypox IL-2; capecitabine; carboxamide-aminotriazole; carboxyamidotriazole; CaRest M3; CARN 700; cartilage derived inhibitor; casein kinase inhibitors (ICOS); castanospermine; cecropin R4; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacarbazine; daunorubicin hydrochloride; decitabine; dexormaplatin; dezaguanine; dezaguanine mesylate; diaziquone; docetaxel; doxorubicin hydrochloride; droloxifene; droloxifene citrate; dromostanolone propionate; duazomycin; DHEA; dacliximab; dehydrodidemnin B; deslorelin; dexifosfamide; dexrazoxane; dexverapamil; didemnin B; didox; diethylnorspermine; dihydro-5-azacytidine; dihydrotaxol; dioxamycin; diphenyl spiromustine; docosanol; dolasetron; doxifluridine; dronabinol; duocannycin SA; edatrexate; eflornithine hydrochloride; elsamitrucin; enloplatin; enpromate; epipropidine; epirubicin hydrochloride; erbulozole; esorubicin hydrochloride etanidazole; ethiodized oil |131; etoposide phosphate; etoprine; epiandrosterone; ebselen; ecomustine; edelfosine; edrecolomab; elemene; emitefur; epristeride; estramustine analogue; estrogen agonists; estrogen antagonists; exemestane; fadrozole hydrochloride; fazarabine; fenretinide; floxuridine; fludarabine phosphate; fluorocitabine, fosquidone; fostriecin sodium; filgrastim; finasteride; flavopiridol; flezelastine; fluasterone; fluorodaunorunicin hydrochloride; torfenimex; formestane; fotemustine; gemcitabine; gemcitabine hydrochloride; gold Au 198; gadolinium texaphyrin; gallium nitrate; galocitabine; ganirelix; gelatinase inhibitors; glutathione inhibitors, hepsulfam; heregulin; hexamethylene bisacetamide; hypericin; idarubicin hydrochloride; ilmofosine; interferon alfa-2a; interferon alfa-2b; interferon alfa-n1; interferon alfa-n3; interferon beta-Ia; interferon gamma-Ib; iproplatin; irinotecan hydrochloride; ibandronic acid; idoxifene; idramantone; ilomastat; imidazoacridones; imiquimod; immunostimulant peptides; insulin-like growth factor-1 receptor inhibitor; interferon agonists; interleukins; iobenguane; Iododoxarubicin; ipomeanol; irinotecan; iroplact; irsogladine; isobengazole; isohomohalicondrin B; itasetron; jasplakinolide; kahalalide F; lanreotide acetate; letrozole; leuprolide acetate; liarozole hydrochloride; lometrexol sodium; losoxantrone hydrochloride; lamellarin-N triacetate; lanreotide; leinamycin; lenograstim; lentinan sulfate; leptolstatin; leukemia inhibiting factor; leukocyte alpha interferon; leuprolide+estrogen+progesterone; leuprorelin; levamisole; linear polyamine analogue; lipophilic disaccharide peptide; lipophilic platinum compounds; lissoclinamide 7; lobaplatin; lombricine; lonidamine; lovastatin; loxoribine; lurtotecan; lutetium texaphyrin; lysofylline; lytic peptides; masoprocol; maytansine; mechlorethamine hydrochloride; megestrol acetate; melengestrol acetate; menoageril; methotrexate sodium; metoprine; meturedepa; mitindomide; mitocarcin; mitocromin; mitogillin; mitomalcin; mitomycin; mitosper; mycophenolic acid; maitansine; mannostatin A; marimastat; maspin; matrilysin inhibitors; matrix metalloproteinase inhibitors; merbarone; meterelin; methioninase; metoclopramide; MIF inhibitor; mifepristone; miltefosine; mirimostim; mismatched double stranded RNA; mitoguazone; mitolactol; mitonafide; mitotoxin fibroblast growth factor-saporin; mofarotene; molgramostim; monophosphoryl lipid A+myobacterium cell wall SK; mopidamol; multiple drug resistance genie inhibitor; multiple tumor suppressor 1-based therapy; mustard anticancer agent; mycaperoxide B; mycobacterial cell wall extract; myriaporone; nocodazole; nogalamycin; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide anti-oxidant; nitrullyn; ormaplatin; oxisuran; O6-benzylguanine; octreotide; okicenone; oligonucteotides; onapristone; ondansetron; ondansetron; oracin; oral cytokine inducer;

osaterone; oxaliplatin; oxaunomycin; paclitaxel; pegaspargase; pellomycin; pentamustine; peplomycin sulfate; perfosfamide; pipobroman; piposulfan; piroxantrone hydrochloride; plomestane; porfimer sodium; porfiromycin; prednimustine; puromycin; puromycin hydrochloride; pyrazofurin; paclitaxel analogues; paclitaxel derivatives; palauamine; palmitoylrhizoxin; pamidronic acid; panaxytriol; panomifene; parabactin; pazelliptine; peldesine; pentosan polysulfate sodium; pentostatin; pentrozole; perflubron; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds: platinum-triamine complex; porfiromycin; propyl bis-acridone; prostaglandin J2; proteasome inhibitors; protein A-based immune modulator; protein kinase C inhibitor; protein kinase C inhibitors; protein tyrosine-phosphatase inhibitors; purine nucleoside phosphorylase inhibitors, purpurins; pyrazoloacridine; pyridoxylated hemoglobin polyoxyethylon conjugate; riboprine; rogletimide; raf entagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; safingol hydrochloride; semustine; simtrazene; sparfosate sodium; sparsomycin; spirogermanium hydrochloride; spiromustine; spiroplatin; streptonigrin; strontium chloride Sr 89; saintopin; sarCNU; sarcophytol A; sargramostim; sdi 1 mimetics; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; sornatomedin binding protein; sonermin; sparfosic acid; spicamycin D; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; sulofenur; tallsomycin; taxane; taxoid; tecogalan sodium; tegafur; teloxantrone hydrochloride; temoporfin; teniposide; teroxirone; testolactone; thiamiprine; tiazofurin; tirapazamine; topotecan hydrochloride; toremifene citrate; trestolone acetate; triciribine phosphate; trimetrexate; trimetrexate glucuronate; triptorelin; tubulozole hydrochloride; tallimustine; tamoxifen methiodide; tauromustine; tazarotene; tellurapyrylium; telomerase inhibitors; temozolomide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; titanocene dichloride; topsentin; totipotent stem cell factor; translation inhibitors; tretinoin; triacetyluridine; tropisetron; turosteride; tyrosine kinase inhibitors; tyrphostins; uracil mustard; uredepa; UBC inhibitors; ubenimex; urogenital sinus-derived growth inhibitory factor; urokinase receptor antagonists; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; variolin B; vector system, erythrocyte gene therapy, velaresol; venom; antivenom; veramine; verdins; vinorelbine; vinxaltine: vitaxin; zeniplatin; zinostatin; zorubicin hydrochloride, zanoterone; zilascorb; 20-epi-1,25 dihydroxyvitamin D3; 5-ethynyluracil; and other immunostimulating drugs or therapeutic agents as well as metabolites, salts, and derivatives of the above.

One embodiment of the presently disclosed inventive concept(s) includes a method of suppressing tumor growth in a subject in need of such therapy by first administering to the subject an amount of any of the GGT inhibitory compounds or compound-containing compositions described herein above or otherwise contemplated herein (including derivatives, metabolites, analogues and/or mimic molecules thereof), then administering a chemotherapeutic agent and/or radiation effective to suppress tumor growth in the subject. The compounds/compositions of the presently disclosed inventive concept(s) provide an enhanced antitumor effect when used in combination with the chemotherapeutic agent and/or radiation. In one particular embodiment, the compound(s)/composition(s) is administered several hours prior to administering the chemotherapeutic agent and/or radiation. The compounds/compositions can be administered by any efficacious and suitable route.

The GGT inhibitory compounds and chemotherapeutic agents of any of the pharmaceutical formulations (and/or radiation) disclosed or otherwise contemplated herein can be administered simultaneously (e.g., in a combination formulation), essentially simultaneously (e.g., administration of each compound a few minutes or a few hours apart), or sequentially (e.g., several days apart, or more than a week apart). For example, a GGT inhibitory compound disclosed herein and a conventional chemotherapeutic agent can be administered together, essentially simultaneously, or sequentially. All such variations in administration of the combination therapy are encompassed within the scope of the presently disclosed inventive concept(s).

In one embodiment, the presently disclosed inventive concept(s) includes a method for the prophylaxis and/or treatment of a reversible airways obstruction in a mammal, such as a human, comprising administration of a therapeutically effective amount of any of the compounds/compositions described or otherwise contemplated herein for the prophylaxis and/or treatment of a disease associated with reversible airways obstruction such as, but not limited to, asthma, chronic obstructive pulmonary disease (COPD) (e.g. chronic and wheezy bronchitis, emphysema), allergic reaction, respiratory tract infections, or upper respiratory tract disease (e.g. rhinitis, including seasonal and allergic rhinitis).

The presently disclosed inventive concept(s) also provides for the use of any of the compounds/compositions described or otherwise contemplated herein in the manufacture of a medicament for the prophylaxis and/or treatment of a clinical condition associated with reversible airways obstruction such as, but not limited to, those conditions described above.

In one embodiment, the pharmaceutical formulation comprising the compound(s) described herein has an enteric coating. The enteric coating may be made of a polymer or copolymer. In one embodiment, the polymer or copolymer is selected from the group consisting of poly(lactic-glycolic acid) polyester, cellulose acetate phthalate, hydroxypropylmethyl cellulose phthalate poly(butyl methacrylate), (2-dimethyl aminoethyl) methacrylate, and methyl methacrylate.

The pharmaceutical formulations of the presently disclosed inventive concept(s) can be administered to a patient in any of a wide range of routes. It is well known to those having ordinary skill in the art that such formulations can be provided in a wide variety of types and for a wide variety of possible administration routes, and thus it is well within the skill of an ordinary artisans to select a specific formulation (including the type of formulation that can be administered and additive(s) that can be included in the formulation) and a route of administration, and then test the suitability of those selections for use in accordance with the methods of the presently disclosed and claimed inventive concept(s).

By way of example but not limitation, suitable routes of administration include enteric, parenteral, topical, oral, rectal, nasal, and/or vaginal routes. Parenteral routes include subcutaneous, intramuscular, intravenous, intraperitoneal, intradermal, and sublingual administration. Also, compositions may be implanted and/or injected into a patient using a drug delivery system. The pharmaceutical formulation may be administered locally and/or systemically. The term "systemic administration" refers to any mode or route of administration that results in effective amounts of active ingredient appearing in the blood and/or at a site remote from the route of administration of the active ingredient. Further, the pharmaceutical formulation may be administered intermittently. The advantage of this administration protocol is that it allows the patient to suspend therapy for periods without the worry of inactivity of the drug resulting from the development of resistant cells. As noted, the pharmaceutical formulation may be formulated for enteral, parenteral, and/or topical administration. Indeed, all three types of formulations may be used simultaneously to achieve systemic administration of the active ingredient.

Compounds useful in the methods of the presently disclosed inventive concept(s) may be formulated into compositions together with pharmaceutically acceptable carriers for oral administration in solid and/or liquid form and/or for rectal administration. Pharmaceutically acceptable carriers for oral administration include, but are not limited to, capsules, tablets, pills, powders, troches, and granules. In such solid dosage forms, the carrier can comprise at least one inert diluent such as, but not limited to, sucrose, lactose, or starch. Such carriers can also comprise, as is normal practice, additional substances other than diluents, e.g., lubricating agents such as magnesium stearate. In the case of capsules, tablets, troches, and pills, the carriers may also comprise buffering agents. Carriers such as tablets, pills, and granules can be prepared with enteric coatings on the surfaces of the tablets, pills, or granules. Alternatively, the coated compound can be pressed into a tablet, pill, or granule for administration to the patient. Non-limiting examples of enteric coatings that may be utilized in accordance with the presently disclosed and claimed inventive concept(s) include those that dissolve and/or disintegrate at colonic pH, such as shellac and EUDRAGIT® S anionic copolymers (Evonik Industries AG, Essen, Germany). Additional non-limiting examples of pharmaceutically acceptable carriers include liquid dosage forms for oral administration, e.g. pharmaceutically acceptable emulsions, solutions, suspensions, syrups, and elixirs containing inert diluents commonly used in the art, such as water. Besides such inert diluents, compositions can also include adjuvants such as wetting agents, emulsifying and suspending agents, and sweetening, flavoring, and perfuming agents. Non-limiting examples of pharmaceutically acceptable carriers for rectal administration include suppositories that may contain, in addition to the compounds of the presently disclosed and claimed inventive concept(s), excipients such as cocoa butter and/or a suppository wax.

Suitable injectable solutions include, but are not limited to, intravenous, subcutaneous, and intramuscular injectable solutions. Non-limiting examples of injectable forms include solutions, suspensions, and emulsions. Typically, the compound(s) is injected in association with a pharmaceutical carrier, such as normal saline, Ringers solution, dextrose solution, or other aqueous carrier known in the art. Appropriate non-aqueous carriers may also be used, and non-limiting examples thereof include cyclodextrins (such as but not limited to hydroxypropyl beta cyclodextrin), mixed oils (such as but not limited to, vitamin E oil), polyethylene glycol, and ethyl oleate. One particular non-limiting carrier that may be utilized in accordance with the presently disclosed and claimed inventive concept(s) includes cyclodextrin in water. Frequently, it is desirable to include additives in the carrier; non-limiting examples of additives that may be utilized include buffers, preservatives, and other substances that enhance isotonicity and chemical stability.

When prepared as a solid composition for oral administration, as noted above, the compound may be formed in any suitable dosage form, including tablet, pill, powder, and granule. In such a solid composition, one or more active substances are mixed with at least one of inactive diluent, dispersant, and adsorbent, such as, but not limited to, lactose, mannitol, glucose, hydroxypropylcellulose, microcrystalline cellulose, starch, polyvinyl pyrrolidone, magnesium aluminate metasilicate, or silicic acid anhydride powder. In addition, the composition may be mixed with additives other than diluents based on common methods known in the art. When prepared as tablets or pills, they may be coated, if necessary, with one or more films of gastric or enteric coating substances, such as, but not limited to, saccharose, gelatin, hydroxypropylcellulose, or hydroxymethylcellulose phthalate. Further, they may be capsuled with a substance, such as, but not limited to, gelatin or ethyl cellulose.

When prepared as a liquid composition for oral administration, the compound may be formed in any suitable dosage form, including a pharmaceutically acceptable emulsion, resolvent, suspension, syrup, elixir, or the like. Non-limiting examples of suitable diluents include purified water, ethanol, vegetable oil, or emulsifier. Further, this composition may be mixed with an auxiliary agent other than diluent, such as humectant, suspension, sweetening agent, flavor agent, fragrance agent, or antiseptic agent.

When prepared as an injectable composition for parenteral administration, axenic aqueous or non-aqueous solution agents, solubilizing agents, suspensions, or emulsifiers may be used. Aqueous solution agents, solubilizing agents, or solution agents may include water for injection, distilled water for injection, physiological saline, cyclodextorin and derivatives thereof, organic amines such as triethanolamine, diethanolamine, monoethanolamine, and triethylamine, inorganic alkali solution, or the like. For example, propylene glycol, polyethylene glycol, vegetable oils such as olive oil, or alcohols such as ethanol may be used. Further, a surface-active agent (mixed micelle formation) such as polyoxyethylene hydrogenated castor oil, sucrose fatty acid ester, lecithin, or hydrogenated lecithin (liposome formation) may be used as the solubilizing agent. Further, the compound may be prepared as an emulsion comprising a water insoluble resolvent, such as but not limited to, vegetable oils, lecithin, polyoxyethylene hydrogenated castor oil, or polyoxyethylene polyoxypropylene glycol.

Alternatively, for parenteral administration, the composition may be prepared as a lotion, liniment (such as ointment), suppository, or pessary, which contains one or more active substances and is prepared by well-known processes. The composition can also be administered topically. Suitable formulations for topical administration include creams, gels, jellies, mucliages, pastes, and ointments. The compounds may be formulated for transdermal administration, for example in the form of transdermal patches, so as to achieve systemic administration. The composition may also be administered in the form of an implant. The composition may also be administered in the form of an infusion solution or as a nasal or bronchial inhalation, aerosol, or spray. In another embodiment, the composition is incorporated in a pharmaceutically acceptable carrier, diluent, vehicle, or the like for systemic administration by feeding. A non-limiting example of such a carrier is a cyclodextrin (e.g., α-cyclodextrin, β-hydroxypropylcyclodextrin, or γ-cyclodextrin).

The pharmaceutical compositions of the presently disclosed inventive concept(s) may be formulated into unit dosage forms for administration to a patient. The dosage levels of the GGT inhibitor and/or other active ingredient(s) in the unit dosage may be varied so as to obtain an amount of active ingredient(s) effective to achieve cancer-therapeutic activity in accordance with the desired method of administration. The selected dosage level therefore depends upon the nature of the active compound(s) administered, the route of administration, the desired duration of treatment, individual needs, and other factors. If desired, the unit dosage may be such that the daily requirement for active compound is in one dose, or divided among multiple doses for administration, e.g., two to four times per day.

The dosage of the compound of the presently disclosed inventive concept(s) may be varied depending on age, weight, symptoms, therapeutic effects, administration route, treatment time, and other factors. In one embodiment, the compound may be administered orally or parenterally at an amount in the range of, but not limited to, 0.001 mg/kg to 1 g/kg per adult and one to several times a day. With regard to dosage and duration of treatment, it is recognized that the ability of an artisan skilled in pharmaceutical administration of drugs to determine suitable dosages depending on many inter-related factors is well known, and skilled artisans are readily able to monitor patients to determine whether treatment should be started, continued, discontinued, or resumed at any given time. For example, dosages of the compounds are suitably determined depending on the symptoms of the individual subject. The weight, age, and sex of the subject, as well as other similar factors, are also taken into consideration. The amount of the compound to be incorporated into the pharmaceutical composition of the presently disclosed and claimed inventive concept(s) varies with dosage route, solubility of the compound, administration route, administration scheme, and the like. An effective amount for a particular patient may vary depending on factors such as the condition being treated, the overall health of the patient, and the method, route, and dose of administration. A clinician can use parameters known in the art to determine the appropriate dose. Generally, the dose begins with an amount somewhat less than the optimum dose, and it is increased by small increments thereafter until the desired or optimum effect is achieved. Suitable dosages can be determined by further taking into account relevant disclosure known in the art. In one embodiment, the unit dose comprises (but is not limited to) 5-1000 mg of active ingredient comprising at least one compound of the presently disclosed inventive concept(s).

The amount of a compound described herein as represented by Formula I, IIA, or IIB, including pharmaceutically acceptable salts thereof, which is required to achieve a therapeutic effect in the treatment of a condition described herein will, of course, vary with the particular compound, the route of administration, the subject under treatment, and the particular disorder, disease, or condition being treated. For example but not by way of limitation, for treatment of a respiratory condition, the compounds of the presently disclosed inventive concept(s) may be administered by inhalation at a dose of from 0.0005 mg to 100 mg.

Dry powder compositions for topical delivery to the lung by inhalation may, for example but not by way of limitation, be presented in capsules and/or cartridges (such as but not limited to, those formed of gelatin) and/or blisters (such as but not limited to, those formed of laminated aluminium foil) for use in an inhaler or insufflator. Formulations generally contain a powder mix for inhalation of the compound of the presently disclosed and claimed inventive concept(s) and a suitable powder base (carrier substance), such as but not limited to, lactose or starch. Lactose is utilized in one particular, non-limiting embodiment. In one embodiment, each capsule or cartridge may generally contain between 20 μg-10 mg of the compound described herein as represented by Formula I, IIA, or IIB optionally in combination with another therapeutically active ingredient. Alternatively, the compound may be presented without excipients. Packaging of the formulation may be suitable for unit dose or multi-dose delivery.

Spray compositions for topical delivery to the lung by inhalation may for example be formulated as aqueous solutions or suspensions or as aerosols delivered from pressurized packs, such as a metered dose inhaler, with the use of a suitable liquefied propellant. Aerosol compositions suitable for inhalation can be either a suspension or a solution and generally contain the compound represented by Formula I, IIA, or IIB optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichloro-tetra-fluoroethane, especially 1,1,1,2-tetrafluoroethane; 1,1,1,2,3,3,3-heptafluoro-n-propane; or a mixture thereof. Carbon dioxide or other suitable gas may also be used as propellant. The aerosol composition may be excipient free or may optionally contain additional formulation excipients well known in the art such as surfactants (e.g., oleic acid or lecithin, and cosolvents e.g., ethanol). Pressurized formulations will generally be retained in a canister (e.g., an aluminum canister) closed with a valve (e.g., a metering valve) and fitted into an actuator provided with a mouthpiece.

Medicaments for administration by inhalation desirably have a controlled particle size. The optimum particle size for inhalation into the bronchial system is usually 1-10 μm in diameter, and in one particular embodiment, 2-5 μm in diameter. Particles having a size above 20 μm in diameter are generally too large when inhaled to reach the small airways. To achieve these particle sizes the particles of the active ingredient as produced may be size reduced by conventional means, e.g., by micronisation. The desired fraction may be separated out by air classification or sieving. In one particular embodiment, the particles will be crystalline. When an excipient such as lactose is employed, generally, the particle size of the excipient will be much greater than the inhaled medicament.

Intranasal sprays may be formulated with aqueous or non-aqueous vehicles with the addition of agents such as thickening agents, buffer salts or acid or alkali to adjust the pH, isotonicity adjusting agents or anti-oxidants. Solutions for inhalation by nebulation may be formulated with an aqueous vehicle with the addition of agents such as acid or alkali, buffer salts, isotonicity adjusting agents or antimicrobials. They may be sterilized by filtration or heating in an autoclave, or presented as a non-sterile product.

When used in treating respiratory conditions, the compounds and formulations of the presently disclosed inventive concept(s) may be used in combination with and/or include one or more other therapeutic agents, such as but not limited to, anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), and/or antihistamines. The presently disclosed inventive concept(s) thus provides, in a further aspect, a combination comprising at least one compound represented by Formulas I, IIA, and/or IIB, together with one or more other therapeutically active agents, such as but not limited to, an anti-inflammatory agent (e.g., a corticosteroid or an NSAID), an anticholinergic agent, another $\beta_2$-adrenoreceptor agonist, an anti-infective agent (e.g., an antibiotic or an antiviral), and/or an antihistamine. One particular combination includes a corticosteroid, and/or an anticholinergic, and/or a PDE-4 inhibitor. Other particular combinations are those comprising one or two other therapeutic agents in combination with at least one of the compounds disclosed or otherwise contemplated herein.

It will be clear to a person skilled in the art that, where appropriate, the other suitable therapeutic ingredient(s) of the formulations of the presently disclosed inventive concept(s) may be used in the form of salts (e.g. as alkali metal or amine salts or as acid addition salts), esters (e.g. lower alkyl esters), solvates (e.g. hydrates), or as prodrugs to optimize the activity, stability, and/or physical characteristics (e.g. solubility) of the therapeutic ingredient. It will be clear also that where appropriate, the therapeutic ingredients may be used in optically pure form. Suitable anti-inflammatory agents include, but are not limited to, corticosteroids and NSAIDs. Suitable corticosteroids which may be used in combination with the compounds of the presently disclosed inventive concept(s) include, but are not limited to, those oral and inhaled corticosteroids and their prodrugs which have anti-inflammatory activity. Non-limiting examples include methyl prednisolone, prednisolone, dexamethasone, fluticasone propionate, 6α,9α-difluoro-17α-[(2-furanylcarbonyl)oxy]-11β-hy-droxy-16α-methyl-3-oxo androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl)ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Particular non-limiting examples of corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl) oxy]-11β-hydroxy-16α-methyl-3-oxo-androsta-1,4-diene-17β-carbothioic acid S-fluoromethyl ester, and 6α,9α-difluoro-17α-[(2-furanylcarbonyl)oxy]-11β-hy-droxy-16α-methyl-3-oxo-androsta-1,4-diene-17β-carbothioic acid S-fluoromethyl ester.

Suitable NSAIDs include, but are not limited to, sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, β2 integrin antagonists, adenosine receptor agonists or antagonists (e.g. adenosine 2a agonists), cytokine antagonists (e.g. chemokine antagonists), and inhibitors of cytokine synthesis. Other suitable $\beta_2$-adrenoreceptor agonists include, but are not limited to, salmeterol (e.g. as the xinafoate), salbutamol (e.g. as the sulphate or the free base), formoterol (e.g. as the fumarate), fenoterol, or terbutaline, and salts thereof.

The presently disclosed inventive concept(s) is also directed to compositions comprising at least one compound described herein as represented by Formula I, IIA, or IIB and another compound acting as a prodrug compound analogous to a chemotherapeutic compound disclosed herein. Such prodrug compounds are generally themselves inactive or low in activity until converted in vivo into active compounds. Thus, for example, prodrugs such as the methyl ester of any acid functionality, which is not active per se or has very low activity, could be hydrolyzed, either uncatalytically or catalytically with an enzyme such as an esterase, to an active compound. In one non-limiting embodiment, such prodrug compounds may be utilized as one desired therapeutic form of the presently disclosed compounds. These analogous prodrugs can be produced from active compounds based on procedures and factors that are well known to one of ordinary skill in the art. Accordingly as used in the present application, the term "prodrug analogue" refers to a chemical which is relatively non-toxic and pharmacologically inert but which can be transformed in vivo to a pharmacologically active drug. More specifically, the term refers to a derivative, metabolite, or analogue of the presently disclosed compounds which have low or no ability as anti-neoplastic agents until converted in the body to a derivative, metabolite, or analogue with such ability or abilities. Such prodrugs should have favorable properties including, but not limited to, enhanced absorption, water solubility, lower toxicity, or better targeting to the tumor cell (such as by reason of greater affinity to the tumor cell or a larger quantity of activating enzyme in the tumor cell as opposed to a normal cell so that larger concentrations of the active compound are produced in the tumor cell). Non-limiting examples of such compounds include esters, such as methyl, ethyl, phenyl, N,N-dimethylaminoethyl; acyl derivatives such as benzoyl, p-N,N-dimethylaminobenzoyl, N,N-dimethylaminoglycyl; peptide derivatives such as γ-glutamyl, glycyl, and D-Val-Leu-Lys.

The compositions containing the active compounds or prodrugs of the presently disclosed and claimed inventive concept(s) can be formulated so as to be specifically targeted to tumors. The compounds can be attached to or otherwise associated with a reagent that is capable of binding a tumor-associated antigen. For example, but not by way of limitation, the compounds could be covalently attached to a monoclonal antibody capable of specifically binding to a tumor-associated antigen. The antigen may be located on a tumor or in the area of the tumor cell. Such linkages can be made through peptide bond formation with amino groups of an antibody. Suitable reagents include polyclonal and monoclonal antibodies. Accordingly, the presently disclosed inventive concept(s) also provides a method comprising treating cancer (i.e. inhibiting tumor cell growth) by administering a pharmaceutical composition comprising at least one of the compounds of the presently disclosed and claimed inventive concept(s) and a reagent (i.e., monoclonal or polyclonal antibody or other targeting agent) which is capable of binding to a tumor-associated antigen.

Alternatively, the compounds of the presently disclosed inventive concept(s) could be attached to and/or incorporated into liposomes and/or carbohydrate vehicles, which are known to be useful for targeting anti-cancer drugs. In one particular embodiment, the liposomes and/or carbohydrate vehicles can be specifically targeted to tumors by covalently attaching a monoclonal antibody directed to a tumor-associated antigen.

The presently disclosed inventive concept(s) is exemplified in terms of in vitro and in vivo activity against various neoplastic cell lines. The test cell lines employed in the in vitro assays are well recognized and accepted as models for anti-tumor activity in animals.

In one aspect, the presently disclosed inventive concept(s) features the use of a GGT inhibitory compound disclosed herein as a chemosensitizer, in combination with at least one other chemotherapeutic agent and/or radiation dosage. In a particular embodiment, the compound is co-administered with the chemotherapeutic agent and/or radiation dosage to a subject. In another particular embodiment, the compound is co-administered with repeated dosages of the same chemotherapeutic agent and/or a different chemotherapeutic agent (and/or a radiation dosage) to a subject. In one embodiment, the GGT inhibitory compound enhances the efficacy of the chemotherapeutic agent (e.g., a cytotoxic agent and/or radiation dosage) relative to the effect of the cytotoxic agent and/or radiation dosage in the absence of the compound.

As noted elsewhere herein, in one embodiment of the presently disclosed inventive concept(s), the any of the compounds described or otherwise contemplated herein is administered in combination with at least one cytotoxic agent. The phrase "in combination" as used in this context means that the agents are given substantially contemporaneously, either simultaneously or sequentially (when delivered sequentially, the cytotoxic agent may be administered before and/or after the compound, and vice versa). If given sequentially, at the onset of administration of the second compound, the first of the two compounds may still be detectable at effective concentrations at the site where the treatment effect is desired. In a non-limiting example, the compound is used in a combination therapy with conventional cancer chemotherapeutics and/or treatments. Conventional treatment regimens for tumors include, but are not limited to, radiation, antitumor agents, interferons, interleukins, tumor necrosis factors, or a combination of two or more of these agents, as well as other chemotherapeutic (cytotoxic) agents described herein or otherwise known in the art.

In an alternative embodiment, the compounds of the presently disclosed inventive concept(s) are present in pharmaceutical compositions that are used for the treatment of degenerative diseases. In particular, the pharmaceutical compositions may be utilized for the treatment of chronic renal and/or inner ear conditions and/or injuries which are reactive oxygen species (ROS)-induced. Degenerative diseases are considered to be diseases which are linked to chronic disorders and/or chronic physiological damages in the human or animal body. Besides degenerative diseases of, inter alia, the central nervous system, chronic disorders of the kidneys or the liver may lead to degeneration of the corresponding tissues. For example, renal diseases and inner ear degenerative diseases are frequent pathological conditions for which few treatments are available. In particular, glomerulosclerosis and other renal diseases are a frequent complication of many chronic conditions (including diabetes) where an excess of reactive oxygen species (ROS) is thought to play a crucial role, considering, for instance, the particular oxygen species to be scavenged as well as its site of action. It would be advantageous to inhibit specifically the enzymatic activity that generates the particular ROS responsible for the tissue damage. Recently, reaction conditions have been defined in vitro, in which ROS are formed as a consequence of the action of the enzyme GGT. Thus, the presently disclosed and claimed inventive concept(s) also relates to the use of GGT inhibitors described or otherwise contemplated herein for the preparation of pharmaceutical compositions for the treatment of a degenerative disease.

It has been found that overexpression of the enzyme GGT is a source of damaging ROS in the kidney and other cells, in particular cells of the inner ear. Thus, the inhibition of GGT (systemic and/or local) will lead to means and methods for successfully and effectively preventing the progress of the chronic tissue damage imposed by elevated ROS levels in the kidney and the inner ear. In particular, examples of chronic renal diseases contemplated for treatment herein include, but are not limited to, focal and/or segmental glomerulosclerosis, minimal change nephrosis, inflammatory and/or autoimmune glomerulopathies, and diabetic nephropathy.

Examples of inner ear injuries which may be treated using the GGT inhibitors described herein include, but are not limited to, sensineural deafness induced by age, physiological status, metabolical status and/or drugs. One example of an inner ear degenerative condition treatable according to the presently disclosed inventive concept(s) is otosclerosis.

Thus, in one embodiment, the presently disclosed inventive concept(s) includes a method of treating a patient for a degenerative disease and/or condition comprising a chronic renal disease, cardiovascular disease, and/or an inner ear degenerative condition and/or injury, as described herein, comprising administering to the patient a composition comprising any of the GGT inhibitory compounds described or otherwise contemplated herein.

As noted above, OU749 (Compound 1) was previously identified as an inhibitor of the GGT transpeptidation reaction (14). Studies of OU749's inhibitory activity revealed that it is uncompetitive against L-γ-glutamyl paranitroanalide (L-GpNA) in the transpeptidation reaction, binding the enzyme-glutamyl substrate complex (F-form) and competing with the acceptor (14). Without wishing to be bound by theory, it is hypothesized that OU749 and several of its structural analogs inhibit both the hydrolysis and transpeptidation reactions catalyzed by GGT. The experimental evidence described hereinbelow provides in depth kinetic analyses of the inhibition of both reactions by OU749 and a series of new benzylthiadiazol sulfonamide analogs. The potency with which the compounds inhibited the reactions and the mechanisms of inhibition was analyzed. These data were compared to the inhibition by the glutamine analog, acivicin, a slow binding inhibitor with a slow rate of release. The analyses of both the hydrolysis and transpeptidation reactions were conducted at physiologic pH. The standard GGT assay, used by other investigators, is conducted at pH 8.0 or higher, which may alter the physiologic cleavage mechanism due to decreased protonation of the amino acid side chains within the active site (24). In addition, in the transpeptidation reaction, the presence of high concentrations of acceptor may induce conformational changes in the enzyme similar to the effects of hippurate (24). The present data provide insights into the essential features of both the acceptors and inhibitors of the GGT reaction.

The presently disclosed inventive concept(s), having now been generally described, will be more readily understood by reference to the following examples and embodiments, which are included merely for purposes of illustration of certain aspects and embodiments of the presently disclosed inventive concept(s), and are not intended to limit the presently disclosed inventive concept(s). Without further elaboration, it is believed that one skilled in the art can, using the preceding description, practice the presently disclosed inventive concept(s) to the fullest extent. The following detailed examples and methods describe how to make and use the various compounds of the presently disclosed inventive concept(s) and are to be construed, as noted above, only as illustrative, and not limitations of the preceding disclosure in any way whatsoever. Those skilled in the art will promptly recognize appropriate variations from the procedures.

EXAMPLES

Synthesis of Compounds

Compounds 2-20

Figure 4:
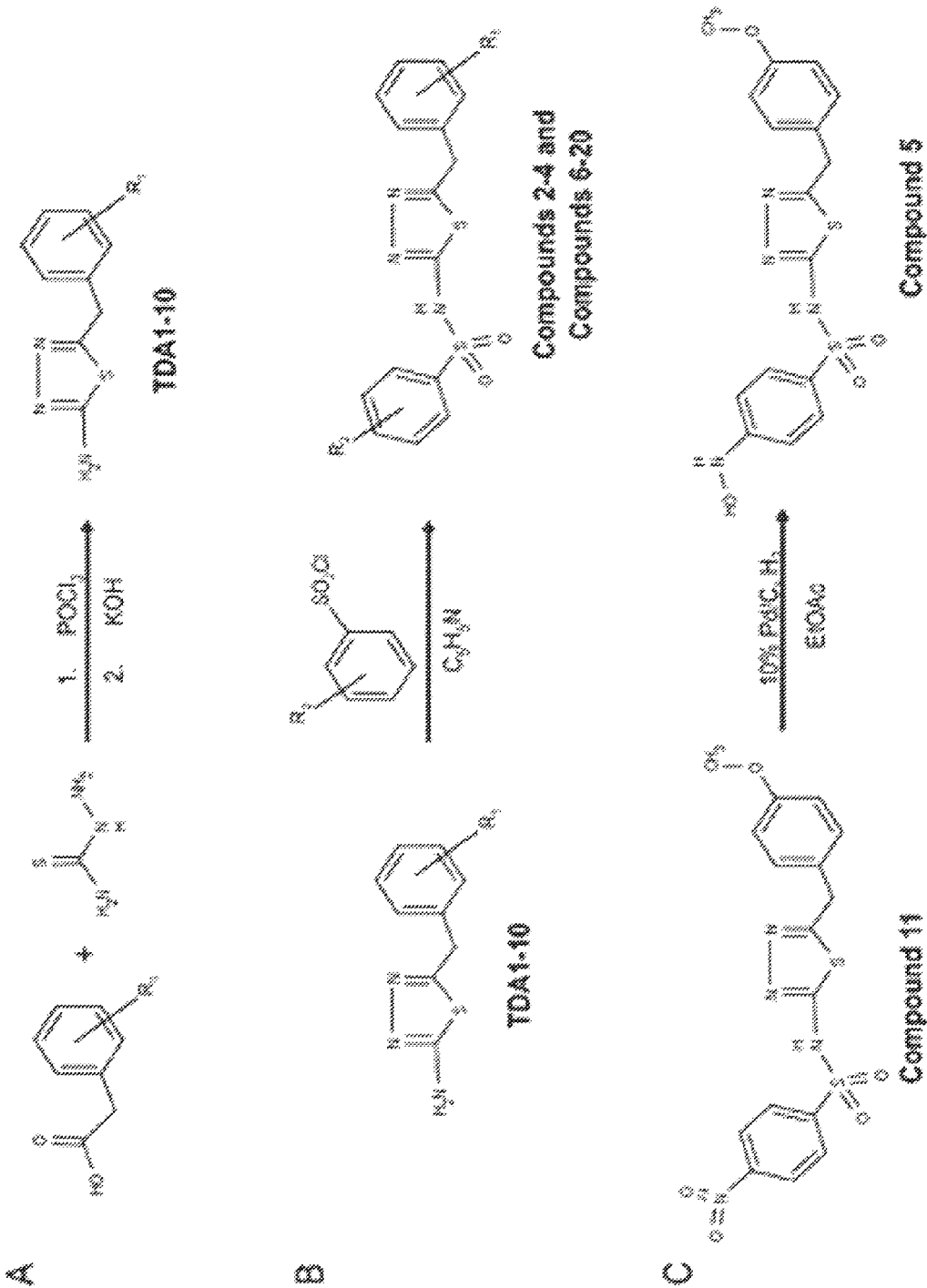
FIG. 4 depicts a synthetic scheme for several thiadiazol sulfonamide compounds. (A) Synthesis and purification of the synthetic thiodiazole intermediates TDA1-10. (B) Use of TDA1-10 in synthesis of Compounds 2-4 and Compounds 6-20. (C) Synthesis of Compound 5 from Compound 11.

Synthesis of synthetic thiodiazole intermediates TDA1-10 (FIG. 4A): Two mmol of the appropriate phenyl acetic acid and 2 mmol of thiosemicarbazide were dissolved in 1 mL of $POCl_3$ and refluxed for 45 minutes. The reaction was then cooled to room temperature, and 3 mL of water were added carefully. The solution was then refluxed for 4 hrs. The reaction mixture was filtered hot, and the solid was washed with warm water. The filtrate was basified with saturated KOH, and the solid was isolated by filtration. The solid was recrystallized from ethanol. The characteristics of each intermediate are as follows: TDA-1: 283 mg (64%), off-white crystals, mp 195-197° C.; $^1$H NMR (300 MHz, DMSO) δ 3.81 (s, 3H), 4.19 (s, 2H), 5.01 (br s, 2H), 6.88 (d, 2H, 8.4), 7.22 (d, 2H, 8.4). MS (m/z)=244.05 [M+Na]$^+$; TDA-2: 203 mg (53%), off-white crystals, mp 182-184° C.; $^1$H NMR (300 MHz, DMSO) δ 4.14 (s, 2H), 7.04 (s, 2H), 7.31 (m, 5H). MS (m/z)=214.04 [M+Na]$^+$; TDA-3: 317 mg (61%), off-white crystals, mp 182° C.; $^1$H NMR (300 MHz, DMSO) δ 4.19 (s, 2H), 7.10 (s, 2H), 7.28 (d, 1H, 8.1), 7.58 (s, 1H), 7.60 (d, 1H, 8.1). MS (m/z)=281.96 [M+Na]$^+$; TDA-4: 307 mg (68%), off-white crystals, mp 196-198° C.; $^1$H NMR (300 MHz, DMSO) δ 4.16 (s, 2H), 7.06 (s, 2H), 7.30 (d, 2H, 8.1), 7.39 (d, 2H, 8.1). MS (m/z)=248.00 [M+Na]$^+$; TDA-5: 205 mg (50%), off-white crystals, mp 204-206° C.; $^1$H NMR (300 MHz, DMSO) δ 2.27 (s, 3H), 4.09 (s, 2H), 7.02 (s, 2H), 7.14 (s, 4H). MS (m/z)=228.06 [M+Na]$^+$; TDA-6: 217 mg (52%), off-white crystals, mp 206-208° C.; $^1$H NMR (300 MHz, DMSO) δ 4.15 (s, 2H), 7.04 (s, 2H), 7.16 (t, 2H, 8.4) 7.32 (t, 2H, 8.4). MS (m/z)=232.03 [M+Na]$^+$; TDA-7: 368 mg (78%), off-white crystals, mp 187° C.; $^1$H NMR (300 MHz, DMSO) δ 4.34 (s, 2H), 7.12 (s, 2H), 7.57 (d, 2H, 8.7), 8.20 (d, 2H, 8.7). MS (m/z)=259.03 [M+Na]$^+$; TDA-8: 216 mg (48%), off-white crystals, mp 193-195° C.; $^1$H NMR (300 MHz, DMSO) δ 4.18 (s, 2H), 7.07 (s, 2H), 7.25 (d, 1H, 7) 7.34 (m, 3H). MS (m/z)=248.00 [M+Na]$^+$; TDA-9: 194 mg (41%), off-white crystals, mp 185-187° C.; $^1$H NMR (300 MHz, DMSO) δ 2.86 (s, 6H), 3.99 (s, 2H), 6.68 (d, 2H, 8.4), 6.97 (s, 2H), 7.07 (2, 2H, 8.4). MS (m/z)=257.08 [M+Na]$^+$; TDA-10: 207 mg (50%), off-white crystals, mp 194-196° C.; $^1$H NMR (300 MHz, DMSO) δ 2.26 (s, 3H), 4.10 (s, 2H), 7.02 (s, 2H), 7.06 (m, 3H), 7.21 (t, 1H, 7.5). MS (m/z)=228.05 [M+Na]$^+$.

Synthesis of Compounds 2-4 and Compounds 6-20 (FIG. 4B): One mmol of the appropriate thiodiazole compound (TDA1-10) was dissolved in 1 mL of pyridine and cooled to 0° C. The appropriate benzenesulfonyl chloride (1.1 mmol) was then dissolved in 0.5 mL of pyridine and added to the reaction mixture. The reaction was allowed to warm to room temperature and stirred overnight. The reaction was diluted with 10 mL of water and acidified with dilute HCl. The solid was then filtered and washed with water. The product was recrystallized from ethanol. The characteristics of each OU749 analogs are as follows: OU749 (Compound 1): 153 mg (42%), off-white crystals, mp 122-124° C.; $^1$H NMR (300 MHz, DMSO) δ 3.75 (s, 3H), 4.12 (s, 2H), 6.93 (d, J=8.6 Hz, 2H), 7.25 (d, J=8.5 Hz, 2H), 7.64-7.45 (m, 3H), 7.76 (dd, J=6.9, 1.5 Hz, 2H), 14.06 (s, 1H). MS (m/z)=384.04 [M+Na]$^+$; Compound 2: 259 mg (69%), off-white crystals, mp 143-145° C.; $^1$H NMR (300 MHz, CDCl$_3$) δ 2.41 (s, 3H), 3.84 (s, 3H), 4.07 (s, 2H), 6.91 (d, J=8.8 Hz, 2H), 7.19 (d, J=8.8 Hz, 2H), 7.25 (d, J=7.9 Hz, 2H), 7.79 (d, J=8.3 Hz, 2H), 11.57 (s, 1H). MS (m/z)=398.06 [M+Na]$^+$; Compound 10: 155 mg (39%), off-white crystals, mp 124-126° C.; $^1$H NMR (300 MHz, CDCl$_3$) δ 3.82 (s, 3H), 4.05 (s, 2H), 6.90 (d, J=8.6 Hz, 2H), 7.17 (d, J=8.4 Hz, 2H), 7.41 (d, J=8.4 Hz, 2H), 7.81 (d, J=8.4 Hz, 2H), 11.46 (s, 1H). MS (m/z)=418.01 [M+Na]$^+$; Compound 8: 208 mg (48%), off-white crystals, mp 135-137° C.; $^1$H NMR (300 MHz, DMSO) δ 3.75 (s, 3H), 4.14 (s, 2H), 6.92 (d, J=8.5 Hz, 2H), 7.25 (d, J=8.5 Hz, 2H), 7.71 (dd, J=8.4, 2.1 Hz, 1H), 7.82 (d, J=8.4 Hz, 1H), 7.91 (d, J=2.1 Hz, 1H), 14.25 (s, 1H). MS (m/z)=451.97 [M+Na]$^+$; Compound 9: 178 mg (45%), off-white crystals, mp 168-170° C.; $^1$H NMR (300 MHz, CDCl$_3$) δ 3.82 (s, 3H), 3.84 (s, 3H), 4.04 (s, 2H), 6.89 (d, J=6.9 Hz, 2H), 6.92 (d, J=7.2 Hz, 2H), 7.17 (d, J=8.5 Hz, 2H), 7.82 (d, J=8.8 Hz, 2H), 11.00 (s, 1H). MS (m/z)=414.06 [M+Na]$^+$; Compound 6 (the R$_3$=OCH$_3$ analog of Formula IIA): 27 mg (7%), off-white crystals, mp 170° C.; $^1$H NMR (300 MHz, CDCl$_3$) δ 3.81 (s, 3H), 4.01 (s, 2H), 6.88 (d, J=8.6 Hz, 2H), 7.15 (d, J=8.6 Hz, 2H), 7.48 (t, J=7.8 Hz, 1H), 7.51-7.60 (m, 2H), 7.93-7.80 (m, 1H), 8.01 (d, J=8.2 Hz, 1H), 8.24 (d, J=7.3 Hz, 1H), 8.80-8.60 (m, 1H), 10.60 (s, 1H). MS (m/z)=434.06 [M+Na]$^+$; Compound 3: 185 mg (47%), off-white crystals, mp 134-136° C.; $^1$H NMR (300 MHz, CDCl$_3$) δ 3.83 (s, 3H), 4.09 (s, 2H), 6.91 (d, J=8.5 Hz, 2H), 7.19 (d, J=8.5 Hz, 2H), 7.39 (t, J=7.8 Hz, 1H), 7.51 (d, J=7.8 Hz, 1H), 7.78 (d, J=7.8 Hz, 1H), 7.91 (s, 1H). MS (m/z)=418.01 [M+Na]$^+$; Compound 4: 113 mg (26%), off-white crystals, mp 104-106; $^1$H NMR (300 MHz, DMSO) δ 3.74 (s, 3H), 4.13 (s, 2H), 6.92 (d, J=8.4 Hz, 2H), 7.24 (d, J=8.5 Hz, 2H), 7.60 (dd, J=8.3, 2.3 Hz, 1H), 7.82 (d, J=2.1 Hz, 1H), 7.99 (d, J=8.4 Hz, 1H), 14.27 (s, 1H). MS (m/z)=451.97 [M+Na]$^+$; Compound 11: 214 mg (53%), off-white crystals, mp 187-190° C.; $^1$H NMR (300 MHz, DMSO) δ 3.74 (s, 3H), 4.14 (s, 2H), 6.92 (d, J=8.7 Hz, 2H), 7.25 (d, J=8.7 Hz, 2H), 8.00 (d, J=9.0 Hz, 2H), 8.35 (d, J=9.0 Hz, 2H), 14.34 (s, 1H). MS (m/z)=429.03 [M+Na]$^+$; Compound 7: 110 mg (26%), off-white crystals, mp 178-179° C.; $^1$H NMR (CDCl$_3$) (δ, ppm; J, hertz) 1.27 (s, 9H), 3.75 (s, 3H), 4.12 (s, 2H), 6.93 (d, 2H, 8.7), 7.25 (d, 2H, 8.7), 7.56 (d, 2H, 8.4), 7.67 (d, 2H, 8.4). MS (m/z)=440.15 [M+Na]$^+$; Compound 12: 254 mg (59%), off-white crystals, mp 169-170° C.; $^1$H NMR (CDCl$_3$) (δ, ppm; J, hertz) 3.75 (s, 3H), 4.14 (s, 2H), 6.93 (d, 2H, 8.7), 7.25 (d, 2H, 8.7), 7.93 (d, 2H, 8.4), 7.97 (d, 2H, 8.4). MS (m/z)=452.03 [M+Na]$^+$; Compound 13: 223 mg (59%), off-white crystals, mp 198-200° C.; $^1$H NMR (300 MHz, DMSO) δ 4.23 (s, 2H), 7.52-7.24 (m, 5H), 8.01 (d, J=8.7 Hz, 2H), 8.36 (d, J=8.7 Hz, 2H), 14.36 (s, 1H). MS (m/z)=399.02 [M+Na]$^+$; Compound 20: 219 mg (49%), off-white crystals, mp 199-201° C.; $^1$H NMR (300 MHz, DMSO) δ 4.26 (s, 2H), 7.35 (dd, J=8.1, 1.7 Hz, 1H), 7.63 (d, J=8.2 Hz, 1H), 7.66 (d, J=1.5 Hz, 1H), 8.03 (d, J=8.9 Hz, 2H), 8.36 (d, J=8.8 Hz, 2H), 14.41 (s, 1H). MS (m/z)=466.94 [M+Na]$^+$; Compound 16: 201 mg (49%), off-white crystals, mp 156-158° C.; $^1$H NMR (300 MHz, DMSO) δ 4.24 (s, 2H), 7.37 (d, J=8.4 Hz, 2H), 7.43 (d, J=8.4 Hz, 2H), 8.02 (d, J=8.9 Hz, 2H), 8.36 (d, J=8.8 Hz, 2H), 13.86 (s, 1H). MS (m/z)=432.98 [M+Na]$^+$; Compound 17: 256 mg (66%), off-white crystals, mp 207-209° C.; $^1$H NMR (300 MHz, DMSO) δ 2.29 (s, 3H), 4.16 (s, 2H), 7.17 (d, J=8.4 Hz, 2H), 7.22 (d, J=8.2 Hz, 2H), 8.00 (d, J=8.6 Hz, 2H), 8.35 (d, J=8.5 Hz, 2H), 14.34 (s, 1H). MS (m/z)=413.04 [M+Na]$^+$; Compound 19: 215 mg (55%), off-white crystals, mp 189-192° C.; $^1$H NMR (300 MHz, DMSO) δ 4.22 (s, 2H), 7.19 (t, J=8.8 Hz, 2H), 7.47-7.33 (m, 2H), 8.01 (d, J=8.8 Hz, 2H), 8.35 (d, J=8.8 Hz, 2H), 14.37 (s, 1H). MS (m/z)=417.01 [M+Na]$^+$; Compound 14: 153 mg (36%), off-white crystals, mp 180-183° C.; $^1$H NMR (300 MHz, DMSO) δ 4.42 (s, 2H), 7.63 (d, J=8.7 Hz, 2H), 8.02 (d, J=9.0 Hz, 2H), 8.23 (d, J=8.8 Hz, 2H), 8.36 (d, J=9.0 Hz, 2H), 14.55 (s, 1H). MS (m/z)=422.02 [M+H]$^+$; Compound 15: 194 mg (47%), off-white crystals, mp 185-188° C.; $^1$H NMR (300 MHz, DMSO) δ 4.26 (s, 2H), 7.34-7.28 (m, 1H), 7.39 (dd, J=5.4, 2.9 Hz, 2H), 7.45 (t, J=1.9 Hz, 1H), 8.02 (d, J=8.8 Hz, 2H), 8.36 (d, J=8.8 Hz, 2H), 14.41 (s, 1H). MS (m/z)=432.98 [M+Na]$^+$; Compound 18: 211 mg (54%), off-white crystals, mp 178-180° C.; $^1$H NMR (300 MHz, DMSO) δ 2.30 (s, 3H), 4.18 (s, 2H), 7.12 (d, J=7.9 Hz, 3H), 7.26 (t, J=7.6 Hz, 1H), 8.01 (d, J=8.8 Hz, 2H), 8.35 (d, J=8.8 Hz, 2H), 14.34 (s, 1H). MS (m/z)=413.04 [M+Na]$^+$.

Synthesis of Compound 5 (FIG. 4C): Compound 11 (130 mg, 0.32 mmol) and 10% Pd/C (15.4 mg) were dissolved in EtOAc (7 mL). The reaction was degassed 5 times and stirred at RT for 24 hr under H$_2$. The reaction was filtered through celite and concentrated in vacu. Product was recrystallized from EtOAc and Hexanes. The characteristics of Compound 5 are: 112 mg (89%), off-white crystals, mp 167-168° C.; $^1$H NMR (300 MHz, DMSO) δ 3.74 (s, 3H), 4.10 (s, 2H), 6.83 (d, J=8.8 Hz, 2H), 6.92 (d, J=8.6 Hz, 2H), 7.24 (d, J=8.6 Hz, 2H), 7.52 (d, J=8.7 Hz, 2H), 8.65 (s, 1H), 8.93 (s, 1H), 13.87 (s, 1H). MS (m/z)=415.05 [M+Na]$^+$.

Compounds 21-30

General procedure A: Two mmol of the appropriate phenyl acetic acid and 2 mmol of thiosemicarbazide were dissolved in 1 mL of POCl$_3$ and refluxed for 45 minutes. The reaction was then cooled to room temperature and 3 mL of water were added carefully. The solution was then refluxed for 4 hours. The reaction mixture was filtered hot and the solid was washed with warm water. The filtrate was basified with saturated KOH and the solid was isolated by filtration. The solid was recrystallized from ethanol.

General procedure for the reduction of Compounds 21-30 to the amine: The appropriate nitro-Compound (0.25 mmol) and SnCl$_2$.H$_2$O (8 g/g of Compound) were dissolved in 15 mL of ethanol dichloromethane (DCM) (1:1) and heated to 40° C. Concentrated HCl (0.2 mL) was added and reaction was stirred for 2 hr. The reaction mixture was poured into H$_2$O and filtered through celite. The filtrate was neutralized with solid NaHCO$_3$ and extracted with ethylacetate (EtOAc). The organic layer was dried with Na$_2$SO$_4$ and concentrated in vacu. Compound 21: 89.5 mg (97%), off white crystals, mp 120-121° C.; $^1$H NMR (300 MHz, DMSO) δ 3.74 (s, 3H), 4.08 (s, 2H), 5.89 (s, 2H), 6.54 (d, J=8.6 Hz, 2H), 6.91 (d, J=8.6 Hz, 2H), 7.23 (d, J=8.5 Hz, 2H), 7.35 (d, J=8.6 Hz, 2H), 13.71 (s, 1H). MS (m/z)=399.06 [M+Na]$^+$. Compound 25: 85 mg (98%), white solid, mp 94-96° C. $^1$H NMR (300 MHz, DMSO) δ 4.16 (s, 2H), 5.91 (s, 2H), 6.54 (d, J=8.3 Hz, 2H), 7.39-7.27 (m, 7H). MS (m/z)=369.02 [M+Na]$^+$. Compound 29: 86 mg (83%), orange solid, mp 186-188° C. $^1$H NMR (300 MHz, DMSO) δ 4.20 (s, 2H), 5.94 (s, 2H), 6.56 (d, J=8.6 Hz, 2H), 7.32 (dd, J=8.2, 1.8 Hz, 1H), 7.38 (d, J=8.6 Hz, 2H), 7.60 (t, J=8.2 Hz, 1H), 7.64 (d, J=1.7 Hz, 1H).). MS (m/z)=436.90 [M+Na]$^+$. Compound 28: 89 mg (93%), white solid, mp 198-202° C. $^1$H NMR (300 MHz, DMSO) δ 4.16 (s, 2H), 5.87 (s, 2H), 6.54 (d, J=8.4 Hz, 2H), 7.44-7.30 (m, 6H). MS (m/z)=403.02 [M+Na]$^+$. Compound 22: 85 mg (94%), white solid, mp 136-139° C. $^1$H NMR (300 MHz, DMSO) δ 2.28 (s, 3H), 4.10 (s, 2H), 5.91 (s, 2H), 6.54 (d, J=8.4 Hz, 2H), 7.29-7.10 (m, 4H), 7.42 (ddd, J=20.3, 8.4, 5.7 Hz, 4H). MS (m/z)=383.03 [M+Na]$^+$. Compound 26: 72 mg (79%), orange solid, mp 124-126° C. $^1$H NMR (300 MHz, DMSO) δ 4.16 (s, 2H), 5.90 (s, 2H), 6.54 (d, J=8.6 Hz, 2H), 7.18 (t, J=9.2 Hz, 2H), 7.48-7.29 (m, 5H). MS (m/z)=386.98 [M+Na]$^+$. Compound 23: 57 mg (63%), yellow solid, mp 125-127° C. $^1$H NMR (300 MHz, DMSO) δ 3.93 (s, 2H), 5.11 (s, 2H), 5.93 (s, 2H), 6.53 (dd, J=8.2, 3.5 Hz, 4H), 6.94 (d, J=8.4 Hz, 2H), 7.35 (d, J=8.1 Hz, 2H). MS (m/z)=384.01 [M+Na]$^+$. Compound 27: 78 mg (80%), orange solid, mp 125-127° C. $^1$H NMR (300 MHz, DMSO) δ 2.88 (s, 6H), 4.01 (s, 2H), 5.93 (s, 2H), 6.54 (d, J=8.4 Hz, 2H), 6.70 (d, J=8.1 Hz, 2H), 7.11 (d, J=8.2 Hz, 2H), 7.35 (d, J=8.3 Hz, 2H). MS (m/z)=412.07 [M+Na]$^+$. Compound 24: 87 mg (97%), white solid, mp 194-196° C. $^1$H NMR (300 MHz, DMSO) δ 2.29 (s, 3H), 4.11 (s, 2H), 5.92 (s, 2H), 6.54 (d, J=8.6 Hz, 2H), 7.14-7.08 (m, 3H), 7.27-7.22 (m, 1H), 7.36 (d, J=8.6 Hz, 2H). MS (m/z)=383.06 [M+Na]$^+$. Compound 30: $^1$H NMR (300 MHz, DMSO) δ 3.76 (s, 3H), 4.18 (s, 2H), 6.91 (d, J=8.6 Hz, 2H), 7.26 (d, J=8.6 Hz, 2H), 7.49-7.62 (m, 2H), 7.74 (d, J=8.8 Hz, 1H), 7.83-8.05 (m, 3H), 8.17 (s, 1H), 9.00 (s, 1H).

Methods—Study 1

Enzyme Isolation: Human GGT1 (P19440), lacking the transmembrane domain, was expressed in *Pichia pastoris* and isolated as previously described (14). The specific activity of the purified enzyme was 406.5 units/mg. One unit of GGT activity was defined as the amount of enzyme that released 1 μmol of paranitroaniline/min at 37° C. at pH 7.4 in the transpeptidation reaction.

Hydrolysis Reaction: The assay buffer contained: 100 mM Na$_2$HPO$_4$, 3.2 mM KCl, 1.8 mM KH$_2$PO$_4$, and 27.5 mM NaCl pH 7.4. The concentration of the D-GpNA (Bachem, Torrance, Calif.) substrate was varied from 0.25 mM to 3 mM D-GpNA. The reaction was initiated with the addition of 19 mU GGT. The reaction was incubated at 37° C. and monitored continuously at 405 nm by a Bio-Rad model 680 microplate reader with Microplate Manager 5.2 software (Bio-Rad, Hercules, Calif.).

Transpeptidation Reaction: The same assay buffer was used for both the hydrolysis reaction and the transpeptidation reaction. The transpeptidation reaction included 40 mM glycylglycine (glygly, Sigma, St. Louis, Mo.) as the acceptor. The concentration of the substrate for the transpeptidation reaction, L-GpNA (Sigma) was varied from 0.25 mM to 3 mM. The concentration of L-GpNA was 3 mM for experiments in which the concentration of glygly was varied. To initiate the transpeptidation reaction, 4 mU GGT were added. The reaction was incubated at 37° C. and monitored continuously at 405 nm.

Data Analysis: Samples in each experiment were run in triplicate. Each inhibitor was evaluated in two or more independent experiments. Double reciprocal plots were generated to assess data quality and determine the correct rate equation for data fitting. Data were fitted using the proper rate equation and the Marquardt-Levenberg algorithm supplied with the Enzfitter program (BIOSOFT, Cambridge, UK). Kinetic parameters with standard errors were estimated using a simple weighting method.

Data adhering to Michaelis-Menten Kinetics were fitted to eq. 1. Data for initial rate patterns with D-, L-GpNA varied at different fixed levels of glygly were fitted to eq. 2, which describes a ping pong kinetic mechanism. Data for competitive and uncompetitive inhibition were fitted to eqs. 3 and 4. Data for the dependence of $V_{max}$ and $V_{max}/K_{D\text{-}GpNA}$ on the concentration of activator were fitted using eq. 5 (25).

$$v = \frac{V_{max}A}{K_a + A} \quad (1)$$

$$v = \frac{V_{max}AB}{K_aB + K_bA + AB} \quad (2)$$

$$v = \frac{V_{max}A}{K_a\left(1 + \frac{1}{K_{is}}\right) + A} \quad (3)$$

$$v = \frac{V_{max}A}{K_a + A\left(1 + \frac{I}{K_{ii}}\right)} \quad (4)$$

$$y = \frac{a + \frac{X}{K_{IN}}}{1 + \frac{X}{K_{ID}}} \quad (5)$$

$$v = \frac{V_{max}A}{K_a\left(1 + \frac{I}{K_{is}}\right) + A\left(1 + \frac{I}{K_{ii}}\right)} \quad (6)$$

In eqs 1-6, $V_{max}$ are the initial and maximum rates, respectively, $K_a$ and $K_b$ are Michaelis constants for substrates A and B, respectively, and $K_{is}$ and $K_{ii}$ are slope and intercept inhibition constants. In eq. 5, a is the value of $V_{max}$ or $V_{max}/K_{D\text{-}GpNA}$ at zero activator/inhibitor, $K_{ID}$ is the activation or inhibition constant, and $K_{IN}$ is a constant that causes the parameter to go to a constant value at infinite concentrations of X, the activator/inhibitor. The product $a(K_{ID}/K_{IN})$ is the value of $V_{max}$ or $V_{max}/K_{D\text{-}GpNA}$ at infinite activator/inhibitor (25). Data for noncompetitive inhibition were fitted to eq. 6. Data for the dependence of $V_{max}$ and $V_{max}/K_{D\text{-}GpNA}$ on the concentration of activator were fitted using eq. 6 [25].

For irreversible inhibition studies, time courses were fit to eq. 7.

$$P = A(1 - e^{-kt}) \quad (7)$$

In eq. 7, A is the burst amplitude, t is time, and k is the first order rate constant for formation of the inactivated enzyme. Graphs, averages, and standard error between experiments were calculated using Prism GraphPad Software (San Diego, Calif.).

Methods—Study II

Enzyme Isolation: hGGT (P19440), lacking the transmembrane domain, was expressed in *Pichia pastoris* and isolated as previously described [14]. The specific activity of the purified GGT was 400 units/mg. One unit of GGT activity was defined as the amount of enzyme that released 1 μmol of paranitroaniline/min at 37° C. at pH 7.4 in the transpeptidation reaction with L-GpNA.

L-Glutamate Release Assay (Hydrolysis of GSH): This assay measures the production of glutamate from the hydrolysis of GSH by GGT enzyme and has been described in detail previously [46]. The concentration of the substrate, GSH, was varied from 5 μM to 20 μM. The concentration of the inhibitors, OU749 and its analogs, were varied from 15.6 μM to 250 μM. The reaction was initiated with the addition of 10 mU hGGT. The reaction was incubated at 37° C. and monitored continuously at 490 nm by a Bio-Rad model 680 microplate reader with Microplate Manager 5 software (Bio-Rad, Hercules, Calif.). All compounds were also evaluated as inhibitors of glutamate dehydrogenase, the enzyme in the second half of the L-glutamate release assay. None of the compounds in this study inhibited glutamate dehydrogenase.

L-GpNA Transpeptidation Assay: The assay has been described previously [53]. The concentration of the substrate for the transpeptidation reaction, L-GpNA (Sigma, St. Louis, Mo.) was varied from 0.25 mM to 3 mM in the presence of 40 mM GlyGly (Sigma) as the acceptor. The concentration of L-GpNA was 3 mM for experiments in which the concentration of GlyGly was varied. To initiate the transpeptidation reaction, 4 mU GGT were added. A comparison of the activity of GGT among assays showed that the amount of hGGT that had 10 mU activity in the L-GpNA transpeptidation reaction had 0.868 mU of hGGT activity in the L-Glutamate Release Assay.

D-GpNA Hydrolysis Assay: The assay was carried out as previously described [53]. Briefly, the concentration of the D-gamma-glutamyl paranitroanilide (D-GpNA, Bachem, Torrance, Calif.) substrate was varied from 0.125 mM to 1 mM D-GpNA. The reaction was initiated with the addition of 19 mU GGT as determined by the L-GpNA transpeptidation assay. The reaction was incubated at 37° C. and monitored continuously at 405 nm.

Cell Lines: 786-0 cells (ATCC CRL-1932), a human renal adenocarcinoma cell line, were grown in Dulbecco's Modified Eagle's Medium (DMEM) supplemented with 10% fetal bovine serum (FBS) and penicillin/streptomycin (50 units/ml, 50 μg/ml). NIH3T3 cells (ATCC CRL 1658) which are GGT-negative and NIH3T3 cells expressing hGGT [described previously [37] were grown in DMEM/F12 media supplemented with 5% FBS and 0.2 mg/ml G418.

Catabolism of Extracellular GSH: 786-O and NIH3T3 cells were plated in 96-well plates at a density of $5 \times 10^3$ cells/well. After 24 hours, the media was changed to 100 μl cysteine-free DMEM/F12 supplemented with either 20 μM GSH or 20 μM GSH and 100 μM compound 6. After one hour, 50 μl of media was removed and immediately acidified with 5 μl ice-cold 43.1% 5-sulfosalicylic acid. After 10 minutes on ice, the solution was neutralized with 15 μl of 1 M NaOH. The GSH concentration was determined by the method of Tietze [55].

Cytotoxicity Assays: 786-0 cells were plated at $10^3$ cells/well in a 96-well plate in DMEM supplemented with 10% FBS and penicillin/streptomycin (50 units/ml, 50 μg/ml). After 24 hours, the media was changed to fresh media containing OU749 analogs. A 100 mM stock of OU749 and each of its analogs were made in DMSO then diluted in DMEM. Control wells were treated with equivalent concentrations of DMSO. Cell viability was determined 72 hours after the addition of the inhibitors by the MTT assay [56]. For the toxicity of the OU749 and its analogs in 786-0 cells, all determinations were done in triplicate. The $LD_{50}$ of each compound and the standard deviation (S.D.) were calculated with a Prism log (inhibitor) versus normalized response (variable slope) curve fit (Prism, GraphPad Software Inc., San Diego, Calif.).

Results—Study I

Initial Rate Studies with D-GpNA and L-GpNA: In this study, the inhibition of both the GGT hydrolysis and transpeptidation reactions by OU749 and a new series of thiadiazol sulfonamide analogs was studied. The hydrolysis and transpeptidation reactions were analyzed separately by using different stereo-isomers of the γ-glutamyl-p-nitroanilide (GpNA) substrate. The kinetics of both reactions were first characterized in the absence of inhibitors. Cleavage of the γ-glutamyl bond of either D-GpNA or L-GpNA releases p-nitroanaline, which has an $OD_{405}$ of 7,680 $M^{-1}$ $cm^{-1}$, allowing for the reactions to be monitored continuously with high sensitivity. The D-glutamyl isomer of GpNA was used as the substrate for the hydrolysis reaction, in which water serves as the acceptor. The L-glutamyl isomer of GpNA, with glycylglycine (GlyGly) as an acceptor, was used for the transpeptidation reaction. L-GpNA can serve as both a substrate and a low affinity acceptor, while D-GpNA is unable to serve as an acceptor (18, 21, 26). Therefore, in the absence of an added acceptor GGT exclusively catalyzes a hydrolysis reaction with D-GpNA as the substrate. When L-GpNA is used as a substrate, the GGT reaction is a mixture of both the hydrolysis and transpeptidation reactions. Under these conditions, the rate of the reaction is the sum of hydrolysis and transpeptidation reactions, with the hydrolysis reaction contributing more at low L-GpNA concentrations and transpeptidation dominating at saturating substrate concentrations. For the hydrolysis reaction, the second order rate constants, $V/K_{GpNA}$, were similar for D-GpNA and L-GpNA (13.2±0.1 vs 7.8±0.2 $min^{-1}$ $nM^{-1}$), indicating that, at limiting substrate concentrations, the rate of the hydrolysis reaction is similar with D-GpNA and L-GpNA (Table 1). However, the maximum rate ($V_{max}$) obtained with L-GpNA was approximately 3-times faster than that measured with D-GpNA, and the $K_{GpNA}$ for L-GpNA was 5-times higher than that measured for D-GpNA. This is at least partially due to the ability of L-GpNA to serve as an acceptor, resulting in a transpeptidation reaction, which is faster than the hydrolysis reaction. Therefore, to study the hydrolysis reaction in isolation, D-GpNA was used as the substrate without any added acceptor.

Figure 5:
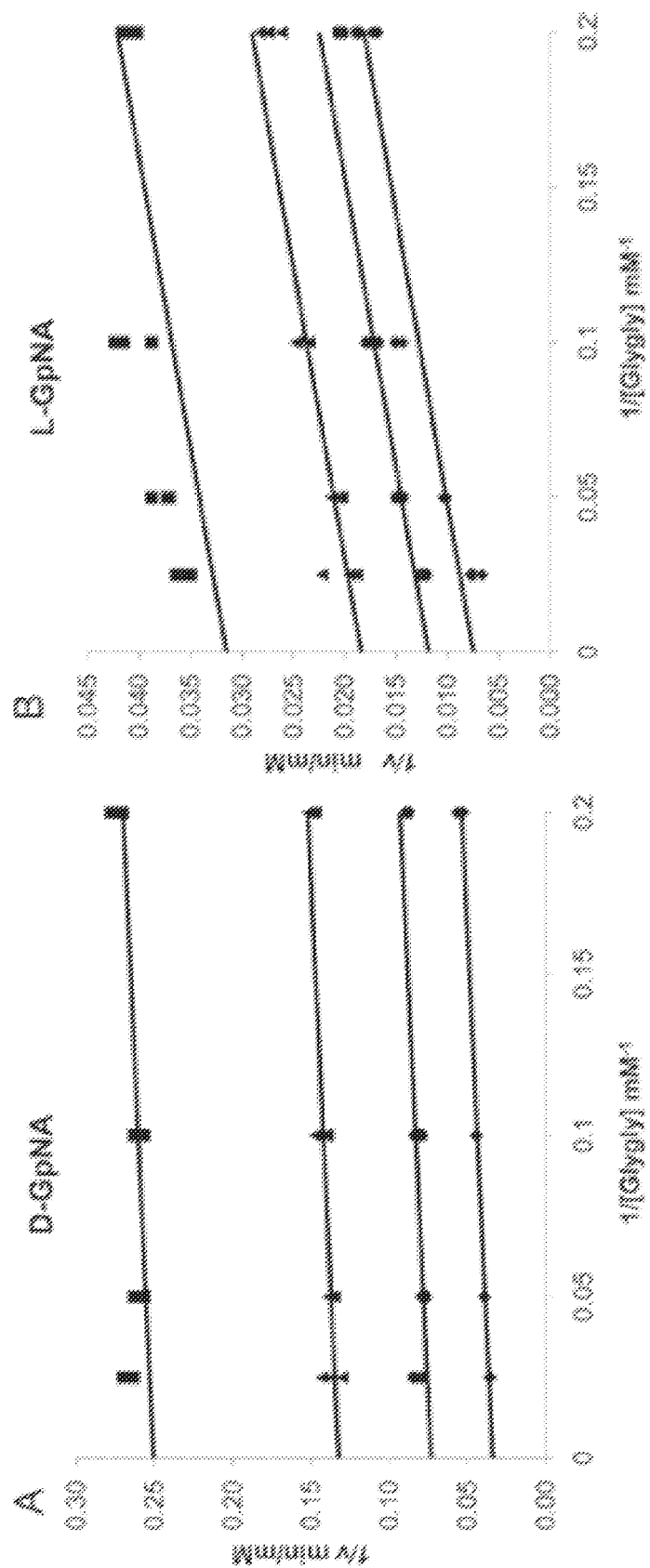
FIG. 5 graphically depicts initial velocity patterns with D-GpNA or L-GpNA as the substrate and glygly as an acceptor. Initial rates were measured at pH 7.4 and 37° C. Double reciprical plots of the initial velocity versus the glygly concentration with 0.25 mM (♦), 0.5 mM (●), 1 mM (▲), or 3 mM (■) D-GpNA (A) or L-GpNA (B).

Characterization of the transpeptidation reaction with both D-GpNA and L-GpNA showed that addition of the acceptor, GlyGly, accelerates the reaction with both substrates (Table 1). In the presence of GlyGly, the kinetic mechanism is ping-pong with D-GpNA or L-GpNA as the donor and GlyGly acting as an acceptor (21, 27). In both cases, data fit well to the rate equation for a ping-pong mechanism, eq. 2, as demonstrated by the parallel lines in the double reciprocal plots (FIGS. 5A and 5B). The measured $V_{max}$ for D- and L-GpNA reactions increased in the presence of GlyGly by 25- and 22-fold, respectively (Table 1). However, some notable differences were observed in the kinetics of the transpeptidation reaction with D-versus L-GpNA. The ratio of the maximum rates of the two reactions was almost 3:1 in favor of L-GpNA over D-GpNA in the presence of GlyGly (141±11 vs 53±11 mM/min·nM). While there was no change in the V/K for D-GpNA in the presence of an acceptor, the V/K for L-GpNA increased by about 15-fold in the presence of GlyGly. Insights into the mechanism of the reaction with L-GpNA provided by these data are included in the discussion. To evaluate the effect of the inhibitors on the transpeptidation reaction, the physiologic L-isomer was used as a substrate with GlyGly as the acceptor.

TABLE 1

Kinetic Parameters for Reaction With D-GpNA and L-GpNA

| Kinetic parameter | D-GpNA Minus acceptor | D-GpNA Plus acceptor | L-GpNA Minus acceptor | L-GpNA Plus acceptor |
|---|---|---|---|---|
| V (mM/min/nM) | 2.1 ± 0.2 | 53 ± 11 | 6.5 ± 0.2 | 141 ± 11 |
| $V/K_{GlyGly}$ ($min^{-1}nM^{-1}$) |  | 7.6 ± 1.5 |  | 14 ± 1 |
| $V/K_{GpNA}$ ($min^{-1}nM^{-1}$) | 13.2 ± 0.1 | 12.7 ± 2.5 | 7.8 ± 0.2 | 117 ± 9 |
| $K_{GlyGly}$ (mM) |  | 7.0 ± 0.3 |  | 9.9 ± 0.9 |
| $K_{GpNA}$ (mM) | 0.16 ± 0.02 | 4.2 ± 0.1 | 0.83 ± 0.06 | 1.2 ± 0.1 |

Acceptor is GlyGly.

Figure 6:
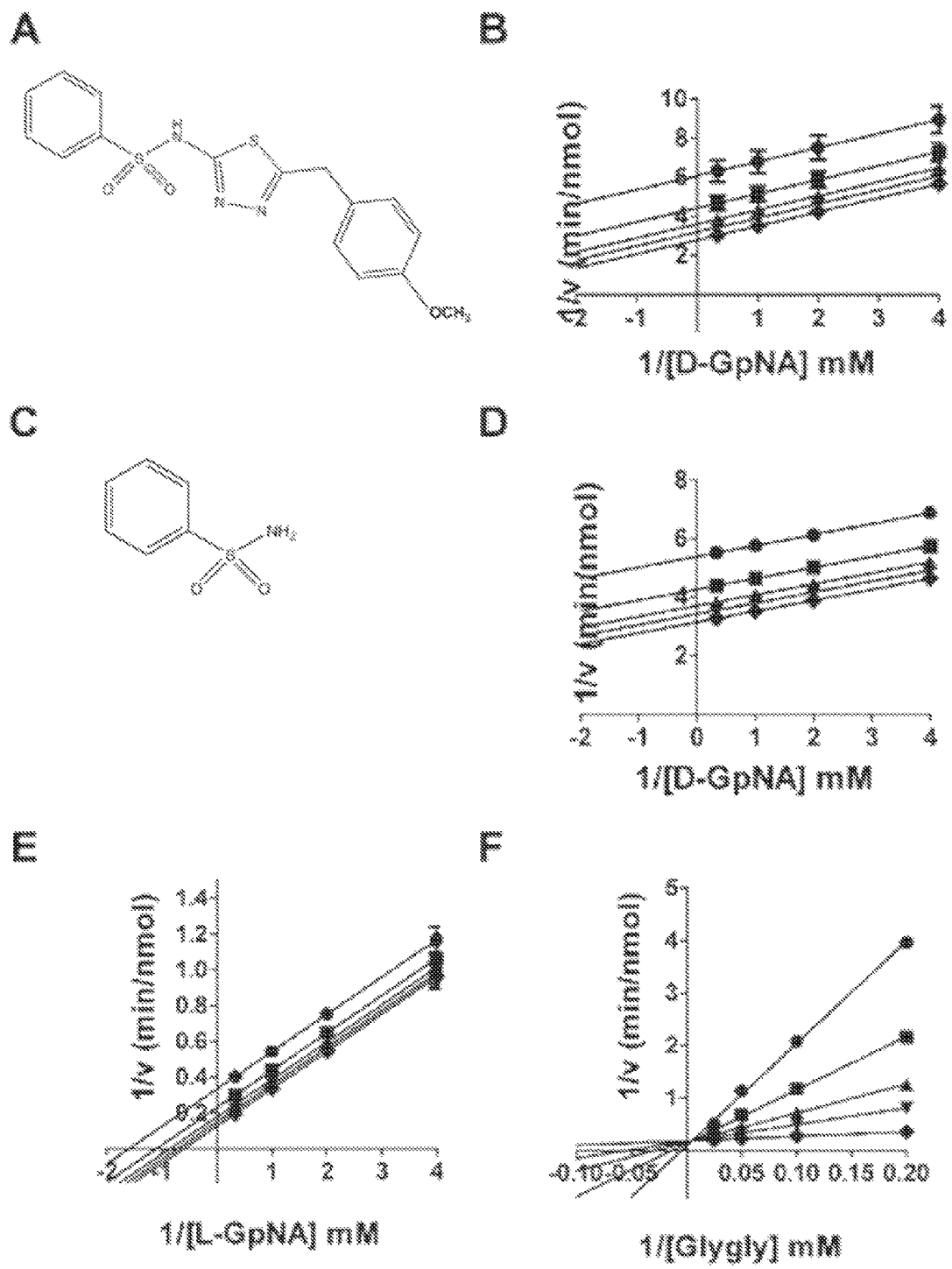
FIG. 6 contains a kinetic analysis of GGT inhibition by OU749 (Compound 1) and sodium benzosulfonamide (SBS). Compound 1 was purchased from ChemBridge Corp (San Diego, Calif.). SBS was purchased from Sigma (St. Louis, Mo.). (A) The structure of OU749 (Compound 1). (B) Double-reciprocal plot of the initial velocity of the hydrolysis of D-GpNA in the presence of 0 (♦), 15.2 µM (▼), 31.25 µM (▲), 62.5 µM (■), 125 µM (●) of OU749. (C) The structure of SBS. (D) Double reciprocal plot of the initial velocity of the hydrolysis of D-GpNA in the presence of 0 (♦), 6.25 mM (▼), 12.5 mM (▲), 25 mM (■), 50 mM (●) SBS. (E-F) Double reciprocal plot of the initial velocity of the transpeptidation reaction with varying concentrations of L-GpNA and 40 mM GlyGly (E) or varying concentrations of GlyGly with 3 mM L-GpNA (F) in the presence of 0 (♦), 6.25 mM (▼), 12.5 mM (▲), 25 mM (■), 50 mM (●) SBS. Data shown are average triplicate values±S.D. For many data points the S.D. is smaller than the symbol.

Inhibition of the GGT hydrolysis and transpeptidation reactions by OU749 (Compound 1): OU749 (FIG. 6A) is an uncompetitive inhibitor of GGT transpeptidation (14). To determine the mechanism by which OU749 inhibits the hydrolysis reaction, the rate of the hydrolysis reaction was determined as a function of D-GpNA concentration and different concentrations of OU749, including zero. Double reciprocal plots of the data gave rise to a series of parallel lines (FIG. 6B). This pattern is indicative of uncompetitive inhibition and binding of OU749 to the covalent E-γ-glutamyl complex (the F-form of the enzyme). This is the same mode of inhibition observed previously for OU749 versus L-GpNA with GlyGly as an acceptor (14). A $K_{ii}$ of ~73 μM was obtained for OU749 in the hydrolysis reaction, which is similar to the $K_{ii}$ of ~68 μM that was obtained in the transpeptidation reaction with the L-GpNA substrate plus acceptor GlyGly (Table 2). These values are comparable to the $K_{ii}$ value of ~73 μM for OU749 measured previously in the transpeptidation reaction (14). Maintaining the L-GpNA substrate concentration at 3 mM while varying the concentration of the acceptor, GlyGly, gave rise to a competitive inhibition profile with a $K_{is}$ of 54 μM, confirming previously reported data with GlyGly as an acceptor (14). Thus, OU749 inhibits GGT by binding to the acceptor site.

Inhibition of GGT by Sodium Benzenesulfonamide: Sodium benzenesulfonamide (SBS, FIG. 6C) is a substructural component of OU749. The effect of SBS on both the hydrolysis and transpeptidation reactions was evaluated. The data show that SBS is an uncompetitive inhibitor vs. D-GpNA in the hydrolysis reaction (FIG. 6D). This is the same mechanism observed for OU749 (FIG. 6B). However, in the hydrolysis reaction, SBS was more than 2.000-fold less effective than OU749 with a $K_{ii}$ of 160±81 mM, (Table 2). These data demonstrate that, although the SBS moiety provides some of the binding energy of OU749, it is a minor contributor. SBS also qualitatively mimics OU749 as an inhibitor of transpeptidation. It is uncompetitive vs L-GpNA (FIG. 6E) and competitive vs GlyGly (FIG. 6F). SBS was several orders of magnitude less potent than OU749 at inhibiting the transpeptidation reaction. For SBS, the $K_{ii}$ and $K_{is}$ values were, 28.8±1.6 mM and 2.28±0.07 mM, respectively, compared with 68 μM and 54 μM for OU749. The difference in the potency of SBS versus OU749 as an inhibitor of both the hydrolysis and transpeptidation reactions implies that the benzosulfonamide portion of OU749 contributes to the inhibition of GGT by blocking access of the acceptor to the acyl bond, although SBS is much less effective than OU749 in this regard. To determine the impact of the benzosulfonamide ring on GGT inhibition, this substructure was modified in the context of OU749, and the effect of these modifications in the hydrolysis and transpeptidation reactions was assessed.

Structural analogs: Modification of the benzenesulfonamide ring: A series of structural analogs of the compound of Formula I (FIG. 1), and Formula IIA (FIG. 2) in the case of compound 6 (the $R_3=OCH_3$ analog of Formula IIA), were tested. The base compound was OU749 (Compound 1) wherein $R_3=OCH_3$. Substitutions were made in the R6, R7, and R8 groups (the ortho, meta and para positions of the benzenesulfonamide ring, respectively). The compounds were evaluated as inhibitors of both the hydrolysis and transpeptidation reactions of GGT (Table 2). The compounds fall into a number of classes of inhibitory potency compared to OU749. Compounds 2-4, with p-methyl, m-chloro, or p, o-dichloro substitutions had no effect on inhibition of the hydrolysis reaction, but were 3-5 times more effective inhibitors of the transpeptidation reaction. These data demonstrate that the aforementioned substitutions do not alter the stability of the ES complex. These compounds are equivalent to OU749 in their ability to block access of water to the acyl bond, but are more effective than OU749 in blocking access of the dipeptide acceptors to the acyl bond in the transpeptidation reaction. Compound 6 had the structure of Formula IIA (FIG. 2) with a methoxy substitution at $R_3$. Compounds 5 with the hydrophilic p-hydroxylamino, compound 6 with the bulky m, o-benzyl, and compound 7 having a p-tBu substitution were 2-5 times less effective than OU749 in inhibiting the hydrolysis reaction but had smaller affects as inhibitors of transpeptidation. The latter was also true of compounds 8-10 with p, m-dichloro, p-methoxy or p-chloro substituents, which were 40-75 times poorer inhibitors of the hydrolysis reaction but, with the exception of the bulkier p-methoxy, were better inhibitors of the transpeptidation reaction. Comparison of the data obtained with compounds 3 and 4, to the data for compounds 8 and 10, reveals that the combination of Cl substituents alters the ability of the inhibitor to block hydrolysis of the acyl bond but has little effect on the transfer of the acyl bond to an acceptor. For the hydrolysis reaction, the detrimental effect of having a Cl substituent in the para position appears to be ameliorated by ortho, but not meta substitution in the same molecule, while meta substitution alone appears to generate no effect.

Figure 7:
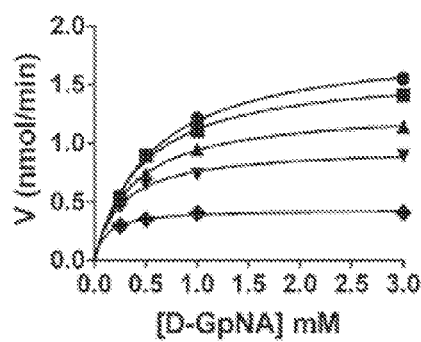
FIG. 7 contains a kinetic analysis of GGT inhibition by Compound 11. (A) Substrate velocity curve of the hydrolysis reaction versus D-GpNA concentration in the presence of 0 (♦), 15.2 µM (▼), 31.25 µM (▲), 62.5 µM (■), 125 µM (●) Compound 11. (B) Velocity vs. Compound 11 concentration (closed symbols) and V/K vs. Compound 11 concentration (open symbols) plots illustrate the activation of the hydrolysis reaction. (C-D) Double-reciprocal plots of the initial velocities of the transpeptidation reaction varying L-GpNA with 40 mM glygly (C) or varying glygly with 3 mM L-GpNA (D) in the presence of 0 (♦), 15.2 µM (▼), 31.25 µM (▲), 62.5 µM (■), 125 µM (●) Compound 11. Data shown are average triplicate values±S.D.
Figure 7:
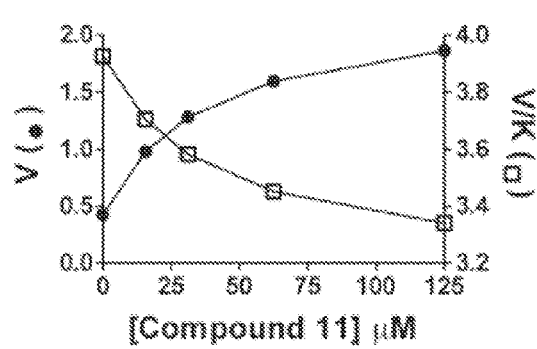
Figure 7:
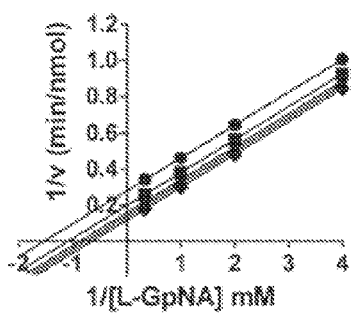
Figure 7:
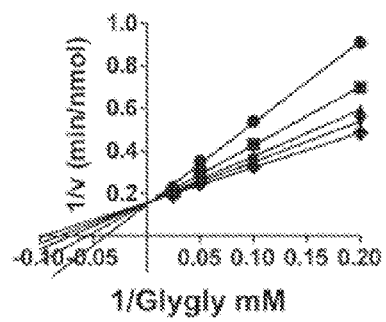

Introduction of a highly electron-withdrawing group, —$NO_2$ or —$CF_3$, in the $R_8$ (para) position (Compound 11 and 12, Table 2) resulted in activation of the hydrolysis reaction. However, addition of these groups maintained inhibition of the transpeptidation reaction, with less than a 2-fold affect on the relative to OU749. Data are shown for Compound 11 (FIG. 7). A detailed analysis of the kinetics of the hydrolysis reaction is shown in FIGS. 7A and 7B. At each of the concentrations of Compound 11, including zero, data were first fitted to eq. 1 to obtain estimates of $V_{max}$ and $V_{max}/K_{D-GpNA}$. The limiting rate constants were fitted to eq. 5, which allows for an estimate of the values of the rate constant at zero and infinite concentration of the compound and a determination of its activation constant ($K_{act}$). Note that activation is observed on $V_{max}$, while inhibition is observed for $V_{max}/K_{D-GpNA}$ (FIG. 7B). The compound is thus a V-type activator in the hydrolysis reaction. GGT inhibition by Compound 11 was also analyzed in the transpeptidation reaction. Compound 11 is an uncompetitive inhibitor vs. L-GpNA in the transpeptidation reaction, indicating that it binds to the L-γ-glutamyl intermediate, presumably at the acceptor site (FIG. 7C). The $K_{ii}$ was 93 μM. The $K_{ii}$ of Compound 11 while varying GlyGly in the transpeptidation reaction was 96 μM (FIG. 7D). The affinity of Compound 11 for the D-γ-glutamyl enzyme intermediate and the L-γ-glutamyl enzyme intermediate differ by only 2.5-fold, demonstrating that there may be a minor difference in the acceptor site or a slight difference in the orientation of the acyl bond depending on the isomer of glutamate that is bound.

TABLE 2

Inhibition of GGT by various thiadiazol sulfonamide compounds

| Compound # | Substitution | Hydrolysis D-GpNA $K_{ii}$ (μM) | Transpeptidation L-GpNA $K_{ii}$ (μM) | Transpeptidation GlyGly $K_{is}$ (μM) |
| --- | --- | --- | --- | --- |
| 1 (OU749) | $R_3 = OCH_3$ $R_{1-2}, R_{4-10} = H$ | 73.2 ± 8.9 | 67.6 ± 6.3 | 54.1 ± 3.9 |
| 2 | $R_3 = OCH_3$, $R_8 = CH_3$ | 73.3 ± 4.0 | 22.7 ± 0.5 | 10.0 ± 0.4 |
| 3 | $R_3 = OCH_3$, $R_7 = Cl$ | 74.9 ± 2.2 | 22.0 ± 0.7 | 11.9 ± 1.1 |
| 4 | $R_3 = OCH_3$, $R_8, R_6 = Cl$ | 75.6 ± 7.2 | 15.7 ± 0.7 | 3.7 ± 1.0 |
| 5 | $R_3 = OCH_3$, $R_8 = NHOH$ | 149.4 ± 13.6 | 64.4 ± 5.1 | 25.7 ± 1.3 |
| 6 (Formula IIA) | $R_3 = OCH_3$ | 161.0 ± 4.5 | 74.9 ± 3.6 | 45.7 ± 3.4 |
| 7 | $R_3 = OCH_3$, $R_8 = C(CH_3)_3$ | 341.5 ± 6.4 | 149.9 ± 13.0 | 143.2 ± 8.7 |
| 8 | $R_3 = OCH_3$, $R_8, R_7 = Cl$ | 3160 ± 90 | 18.2 ± 0.7 | 10.8 ± 0.8 |
| 9 | $R_3 = OCH_3$, $R_8 = OCH_3$ | 3800 ± 720 | 149 ± 23 | 133.3 ± 10.3 |
| 10 | $R_3 = OCH_3$, $R_8 = Cl$ | 5530 ± 1460 | 32.5 ± 0.9 | 13.4 ± 0.8 |
| 11 | $R_3 = OCH_3$, $R_8 = NO_2$ | Activator | 92.8 ± 4.3 | 95.7 ± 7.6 |
| 12 | $R_3 = OCH_3$, $R_8 = CF_3$ | Activator | 116.7 ± 7.4 | 46.3 ± 3.5 |

Compounds 1-5, and 7-12 are based on Formula I;
Compound 6 is based on Formula IIA.
R groups not indicated = H.

Structural analogs: Modification of the benzyl ring: In order to determine the effects of modification of the benzyl ring remote to the benzenesulfonamide moiety, a series of structural analogs of the compound having formula I with $R_8=NO_2$ were synthesized with optional substitutions in the $R_2$ and $R_3$ positions. These compounds are numbered 13-20 in Table 3. Kinetic parameters for modifications of the benzyl ring of nitro compounds are shown in Table 3. A 3- to 6-fold activation of the $V_{max}$ for hydrolysis (the ratio of $V_\infty$ to $V_o$ in Table 3) was observed with an activation constant, $K_{act}$, of 22-54 μM for compounds 13-19. These activators may alter the conformation of the enzyme or be oriented differently than OU749, allowing greater access of water to the acyl bond.

In the transpeptidation reaction, the nitro-containing analogs behave in a manner that is both qualitatively and quantitatively similar to the parent compound, OU749 (Compound 1). Addition of a chlorine group at the $R_3$ position resulted in an inhibitor (Compound 16) with a $K_{ii}$ of 61.9 μM in the transpeptidation reaction. An $OCH_3$ at the $R_3$ position increased the L-GpNA $K_{ii}$ in the transpeptidation reaction less than 2-fold and increased the GlyGly $K_{is}$ more than 2-fold (Compound 11) when compared with Compound 16. No substitution on the benzyl ring of the nitro ($R_8=NO_2$) analog (Compound 13) increased the L-GpNA $K_{ii}$ by almost 2-fold compared to Compound 16 while only slightly increasing the GlyGly $K_{is}$. Addition of a methyl group at the $R_3$ position yielded results similar to having no substitution (Compound 17). Addition of any of a series of chemical groups at the $R_2$ position reduced the strength of this family of inhibitors in the transpeptidation reaction by 2-fold while slightly increasing the strength of the compound as a competitive inhibitor of the acceptor, GlyGly (Compound 15 and 18). Addition of an $NO_2$ at the $R_3$ position (Compound 14) more than doubled the $K_{ii}$ and $K_{is}$ relative to Compound 16 in the transpeptidation. There is very little difference in the behavior of any of these compounds in the transpeptidation reaction with the exception of Compound 19 and Compound 20, which exhibited time dependent inhibition and, together with acivicin, will be discussed below.

TABLE 3

Kinetic Parameters for Activators of the D-GpNA Hydrolysis Reaction and Inhibition of the L-GpNA Transpeptidation Reaction: Effects of thiadiazol sulfonamide compounds

| | | Hydrolysis D-GpNA | | | | Inhibition L-GpNA | |
|---|---|---|---|---|---|---|---|
| | | | | | | Transpeptidation L- | Transpeptidation |
| Cmpd # | Substitution | $V_o^a$ (mM/min/nM) | $V_\infty$ (mM/min/nM) | $K_{Act}$ (μM) | Fold Activation | GpNA $K_{ii}$ (μM) | GlyGly $K_{is}$ (μM) |
| 13 | $R_8 = NO_2$ | 1.59 ± 0.06 | 9.09 ± 0.55 | 54.4 ± 3.0 | 5.72 ± 0.32 | 111.5 ± 5.5 | 59.6 ± 3.7 |
| 14 | $R_3, R_8 = NO_2$ | 1.27 ± 0.01 | 5.08 ± 0.41 | 51.9 ± 0.8 | 4.00 ± 0.11 | 132.5 ± 5.5 | 81.2 ± 8.8 |
| 15 | $R_2 = Cl, R_8 = NO_2$ | 1.30 ± 0.01 | 5.86 ± 0.23 | 38.6 ± 0.3 | 4.51 ± 0.05 | 119.1 ± 7.1 | 43.8 ± 7.7 |
| 11[b] | $R_3 = OCH_3$, $R_8 = NO_2$ | 1.59 ± 0.14 | 8.63 ± 1.21 | 37.1 ± 5.6 | 5.43 ± 2.04 | 92.8 ± 4.3 | 95.7 ± 7.6 |
| 16 | $R_3 = Cl, R_8 = NO_2$ | 1.71 ± 0.09 | 7.70 ± 0.46 | 31.4 ± 2.2 | 4.50 ± 0.63 | 61.9 ± 2.4 | 44.4 ± 3.4 |
| 17 | $R_3 = CH_3, R_8 = NO_2$ | 2.62 ± 0.79 | 11.25 ± 4.27 | 25.3 ± 7.6 | 4.29 ± 2.20 | 112.5 ± 5.2 | 56.9 ± 8.3 |
| 18 | $R_2 = CH_3, R_8 = NO_2$ | 1.15 ± 0.01 | 5.08 ± 0.20 | 25.2 ± 0.2 | 4.42 ± 0.64 | 121.5 ± 8.8 | 34.3 ± 0.9 |
| 19 | $R_3 = F, R_8 = NO_2$ | 1.53 ± 0.09 | 5.39 ± 0.28 | 22.2 ± 2.0 | 3.52 ± 0.60 | Time Dependent | 31.8 ± 0.7 |
| 20[c] | $R_2, R_3 = Cl$, $R_8 = NO_2$ | — | — | — | — | Time Dependent | 10.3 ± 0.5 |

Compounds are based on Formula I where $R_8 = NO_2$. R groups not indicated = H.
[a] $V_o$ = maximum velocity at zero activator; $V_\infty = V_o(K_{ID}/K_{IN})$ in eq. 2, maximum rate at infinite activator; $K_{act}$, activation constant or concentration that gives ½($V_\infty + V_o$), $K_{ID}$ in eq. 2; fold activation = $V_\infty/V_o$.
[b] Normalization of all values to Compound 11 yielded values similar to Compound 11
[c] Compound 20 competitively inhibited the hydrolysis reaction with a $K_{ii}$ with D-GpNA of 78.2 ± 1.9 μM.
Values are ± S.E.

Figure 8:
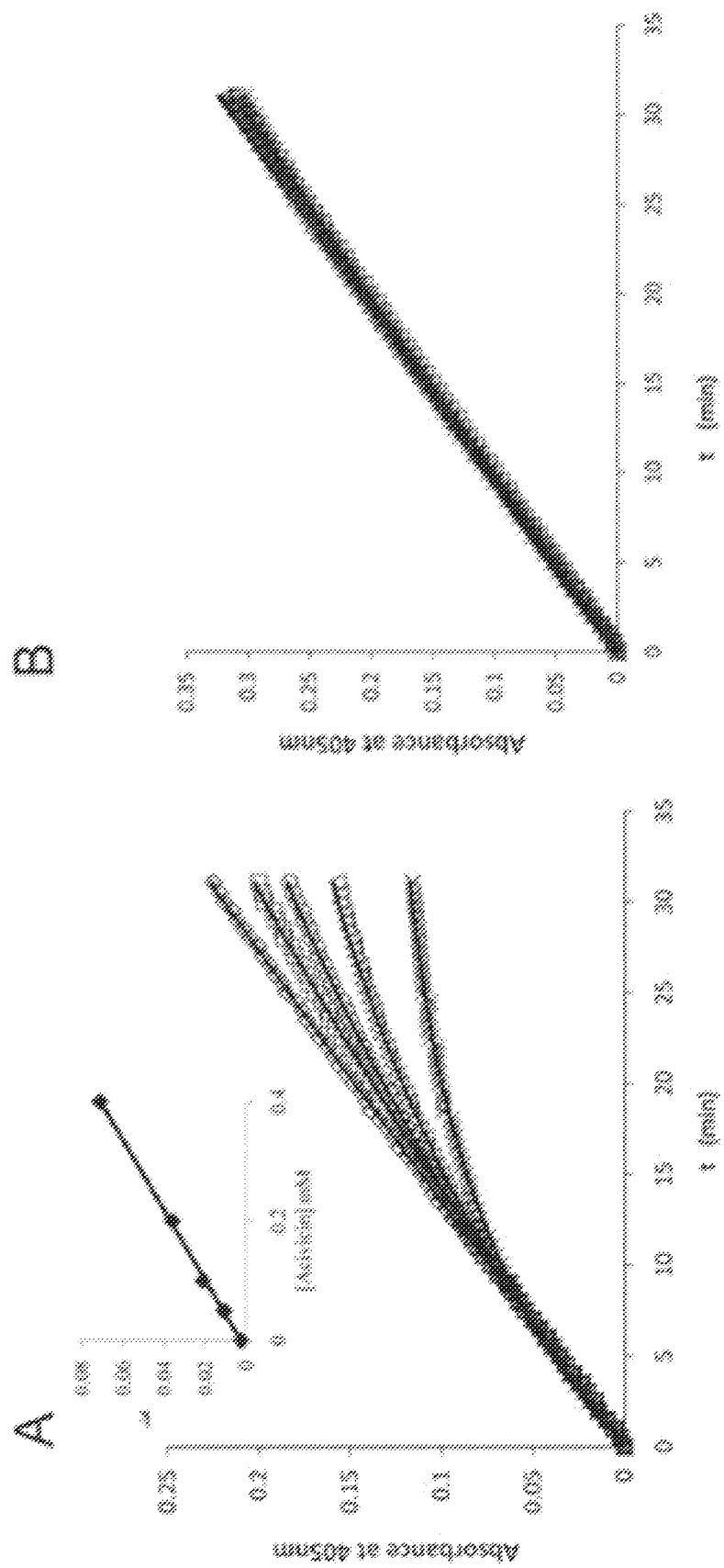
FIG. 8 graphically depicts time courses for the hydrolysis of D-GpNA in the presence of acivicin. The release of pNA from 0.287 mM D-GpNA (A) or 2 mM D-GpNA (B) was monitored over time in the presence of acivicin (concentrations of acivicin noted in A). The reactions were conducted at pH 7.4. The increase in the Km of D-GpNA with increasing concentrations of acivicin is shown (insert 6A).

Acivicin and Acivicin-like Inhibition: Acivicin is an analog of γ-glutamyl donor substrates [GpNA, GSH, etc.] and exhibits reversible competitive inhibition against these substrates with a very slow rate of release (27). The time course for production of pNA in the presence of increasing concentrations of acivicin is shown in FIG. 8. The time course for hydrolysis of 0.287 mM D-GpNA in the absence of acivicin is linear for at least 30 minutes (FIG. 8A). In the presence of increasing concentrations of acivicin, the initial rate is unchanged, but the rate decreases with increasing time, with the most pronounced decrease seen at the highest acivicin concentration (FIG. 8A). A fit of the time courses to the equation for a first-order process gives an observed rate constant, $k_{obs}$, that is a linear function of acivicin concentration. This linear dependence is expected for an irreversible inhibitor, where $k_{obs}$ is the pseudo-first order net on-rate constant for modification of enzyme by acivicin times the concentration of acivicin. The slope of the line depicted in the inset of FIG. 8 thus describes the second order rate constant, $k_{on}$, as 0.171 $mM^{-1}$ $min^{-1}$. Since acivicin is competitive vs. D-GpNA, $k_{obs}$ is equal to the pseudo-first order rate constant divided by $(1+[D-GpNA]/K_{D-GpNA})$. Given a $K_{D-GpNA}$ of 0.16 mM (Table 1) $k_{on}$ corrected for the presence of D-GpNA is 0.48 $mM^{-1}$ $min^{-1}$.

Kinetic analysis of acivicin was also carried out for the transpeptidation reaction using L-GpNA or L-GpNA with GlyGly, and the results were qualitatively the same (data not shown). In the transpeptidation reaction with L-GpNA, the time courses were curvilinear even in the absence of acivicin. Unlike D-GpNA, which can only act as a donor to form the γ-glutamyl enzyme intermediate (F-form), L-GpNA can also act as an acceptor (18, 21, 26). As a result, a complete analysis was only carried out for the hydrolysis reaction using D-GpNA.

Increasing the D-GpNA concentration to saturation eliminated the development of inhibition by acivicin over the same time course as would be expected for competitive inhibition against D-GpNA (FIG. 8B). Time dependent inhibition of the transpeptidation reaction was observed for the monofluoro- (Compound 19, Table 3) and dichloro- (Compound 20, Table 3) substituted compounds shown in Table 3, demonstrating that they also exhibit either irreversible or slow onset inhibition.

Figure 9:
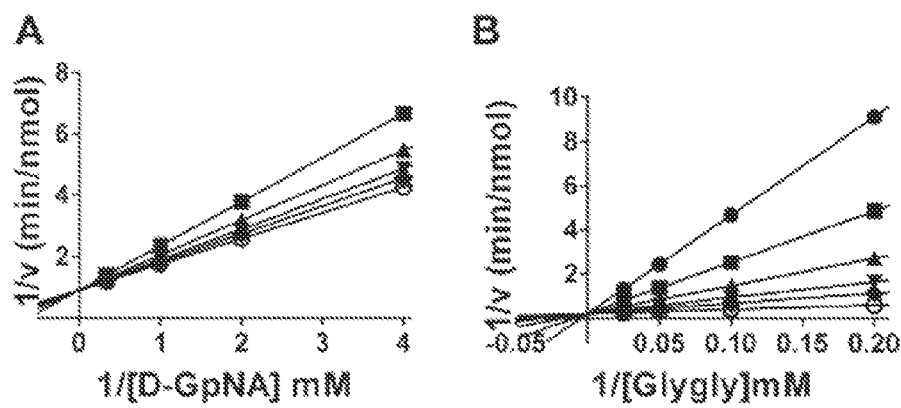
FIG. 9 contains a kinetic analysis of GGT inhibition by Compound 20. (A) Double-reciprocal plot of the initial velocity of the hydrolysis of D-GpNA in the presence of 0 (♦), 15.2 µM (▼), 31.25 µM (▲), 62.5 µM (■), 125 µM (●) Compound 20. (B) Double reciprocal plot of the initial velocity of the transpeptidation reaction with varying concentrations of glygly with 3 mM L-GpNA in the presence of 0 (○), 15.2 µM (♦), 31.25 µM (▼), 62.5 µM (▲), 125 µM (■), 250 µM (●) Compound 20. Data shown are average triplicate values±S.D. For many data points the S.D. is smaller than the symbol.

All of the nitro-containing analogs of Table 3 accelerated the hydrolysis reaction except Compound 20. Compound 20 has chlorines both para ($R_3$) and meta ($R_2$) on the benzyl ring and a $NO_2$ at the para ($R_8$) position on the benzenesulfonamide ring. The inhibition mechanism of Compound 20 is unique among the OU749 analogs, because it is competitive with the γ-glutamyl substrate in the hydrolysis reaction, yielding a $K_{ii}$ with D-GpNA of 78 µM (FIG. 9A). In addition to being competitive with the γ-glutamyl substrate, Compound 20 is also competitive with the acceptor GlyGly in the transpeptidation reaction (FIG. 9B), with a $K_{is}$ of 10 µM (Table 3). However, a $K_{ii}$ with L-GpNA was unable to be established in the transpeptidation reaction, because Compound 20 exhibits slow onset binding similar to acivicin. Thus, the transpeptidation reaction is too complex for accurate analysis and establishment of inhibition constants for this compound.

Discussion—Study I

New benzylthiadiazol sulfonamide compounds (2-20) were evaluated for their inhibitory activity in both the hydrolysis and transpeptidation reactions. All of the new compounds were weaker inhibitors of the hydrolysis reaction relative to OU749 (Compound 1), but some were more potent inhibitors than OU749 in the transpeptidation reaction. In addition to structure-activity information, the divergent results provide insights into the reaction catalyzed by GGT. In both the hydrolysis and transpeptidation reactions, OU749 is an uncompetitive inhibitor of the donor γ-glutamyl substrate. The data provided herein are consistent with OU749 binding to the F-form of the enzyme. Despite the fact that L-GpNA has the capacity to act as an acceptor in the transpeptidation reaction, its maximum turnover rate was only about 3-times higher than that measured for D-GpNA in the absence of GlyGly (Table 1). Thus, although L-GpNA can act as an acceptor, it is not very effective. The second order rate constant measured with L-GpNA is similar to the rate constant with D-GpNA (8 $min^{-1}$ $nM^{-1}$ and 13 $min^{-1}$ $nM^{-1}$, respectively), indicating that formation of the γ-glutamyl-enzyme intermediate (F-form) is independent of the stereochemistry of the γ-glutamyl moiety on the nitroanilide substrate. To develop effective inhibitors for therapeutic use, each compound must be evaluated in the physiologic hydrolysis reaction.

The comparative analyses were begun by characterizing the substructural elements of OU749 (FIG. 6A) that contribute to its efficacy as an inhibitor. The terminal benzosulfonamide moiety of OU749 (provided as the sodium salt, SBS) was evaluated for activity as an inhibitor. SBS is an uncompetitive inhibitor versus the both D-GpNA and L-GpNA and a competitive inhibitor vs. GlyGly in the L-GpNA reaction. The analysis was expanded to a series of OU749 analogs with modifications on the benzosulfonamide ring. As with SBS, compounds 2-10 were more potent inhibitors of the transpeptidation reaction than the hydrolysis reaction (Table 2). However, compared to OU749, all of these structural analogs bound with either equal (compounds 2-4) or lower (compounds 5-10) affinity to the D-γ-glutamyl enzyme. As observed for GlyGly, analogs of OU749 with a strong electron-withdrawing group (—$NO_2$ or —$CF_3$) para to the sulfonamide group activate the hydrolysis reaction with D-GpNA (Compounds 11 and 12, Table 2). Both analogs inhibit the reaction with L-GpNA and exhibit an affinity very similar to that of compounds 2-10 in Table 2. Thus, as was observed for GlyGly in the absence of inhibitors, compounds 11 and 12 activate the hydrolysis reaction. This demonstrates that like GlyGly, they bind to the acceptor site of the E⁻γ-D-glutamyl intermediate (F-form), and in doing so, they may alter the conformation of the intermediate in a manner that allows a more facile attack by water on the ester carbonyl. The $SO_2$ of the benzenesulfonamide group may interact with residues in or near the active site.

All of the OU749 analogs containing a nitroxide group (compounds 11, 13-20), except Compound 20, accelerated the hydrolysis reaction. However, these same analogs inhibited the transpeptidation reaction with an affinity ($K_{ii}$) very similar to that of compounds 2-10 (Table 2). A series of analogs in which the methoxyphenyl ring of compound 11 was modified (Table 3) elicited no major effect on the inhibition of the transpeptidation reaction with the exception of p-F or p-,m-dichloro analogs (compounds 19 and 20), which exhibited a distinct mode of inhibition, similar to that observed for acivicin.

Acivicin is an analog of the γ-glutamyl donor substrate (27-30). It exhibits time-dependent inhibition at low but not at high concentrations of L-GpNA (FIG. 8). The second order rate constant for binding acivicin, $k_{on}$, is 0.48 $mM^{-1}$ $min^{-1}$. This is the same type of inhibition of the transpeptidation reaction as was observed for compounds 19 and 20, indicating that they also exhibit either irreversible or time-dependent inhibition. Of further interest is the fact that the p-, m-dichloro analog (compound 20) is the only compound in this series of analogs that does not accelerate the hydrolysis reaction but rather serves as a competitive inhibitor of the D-GpNA substrate. This is the only analog considered that inhibited a GGT reaction by competing with the γ-glutamyl substrate.

To fully understand the affect of the OU749 analogs in the hydrolysis and transpeptidation reactions, the reactions had to be independently analyzed with both donor substrates, D-GpNA and L-GpNA. In the absence of the acceptor GlyGly, the second order rate kinetics are similar for both D-GpNA and L-GpNA in the GGT hydrolysis reaction, indicating the stereochemistry of the γ-glutamyl group of the substrate does not affect the binding and cleavage of the substrate in the hydrolysis reaction. However, when the acceptor GlyGly is present in the transpeptidation reaction with L-GpNA serving as the donor substrate, the second order rate kinetics increase by 15-fold. Without wishing to be bound by theory, these results suggest three possibilities: (1) the binding of GlyGly increases the rate of hydrolysis, (2) GlyGly could be binding to another site, perhaps an affector site, instead of to the acceptor site that increases the turnover rate, or (3) GlyGly could be binding free enzyme forming an E-GlyGly complex prior to L-GpNA binding. The third possibility would imply a sequential mechanism instead of a ping-pong mechanism. In a ping-pong mechanism, the donor substrate's second order rate constant (V/K) will not change in the absence or presence of an acceptor molecule. A sequential mechanism can also yield the classic ping-pong plots if the $K_m$ for GlyGly is greater than the $K_1$ of GlyGly for the E-GlyGly complex. This is only possible when the GlyGly concentration is varied around the $K_m$ of GlyGly, as was carried out in these studies and previous studies of the GGT transpeptidation reaction (14, 31-32).

It is difficult at best to model the results obtained in this study on a molecular level. The crystal structure for human GGT has not yet been determined. Homology models based on the crystal structures of bacterial GGT lack the resolution necessary for molecular modeling (33-35). Mutational analysis have indicated that the active nucleophile Thr-381, Arg-107 and Asp-423 interact with the alpha-amino and the alpha-carboxylate of glutamate (29-30, 36). Two adjacent serines (Ser-451 and Ser-452) have also been proposed to stabilize the rate-limiting transition state of the catalytic reaction (29). Identification of amino acids involved in the binding of the acceptor has been more elusive, and there is little solid structural work available to delineate the "acceptor" site of GGT from any organism. All of the inhibitors tested herein, with the exception of acivicin, target the acceptor site of human GGT.

Results—Study II

Figure 10:
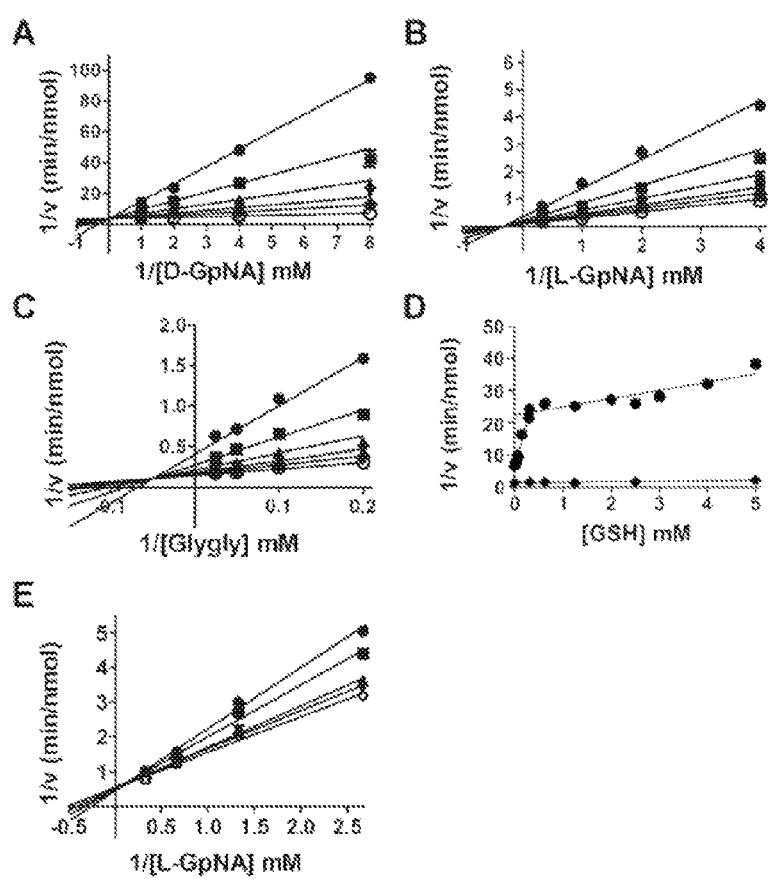
FIG. 10 contains a kinetic analysis of the interaction between GSH and other GGT substrates. (A) Double-reciprocal plot of the initial velocity of the hydrolysis of D-GpNA in the presence of 0 (○), 15 µM (♦), 31.25 µM (▼), 62.5 µM (▲), 125 µM (■), 250 µM (●) GSH showing competitive inhibition between these two gamma-glutamyl donor substrates. (B) Double-reciprocal plot of the initial velocity of the transpeptidation reaction with L-GpNA with 40 mM GlyGly or (C) GlyGly with 3 mM L-GpNA in the presence of 0 (○), 0.3125 mM (♦), 0.6125 mM (▼), 1.25 mM (▲), 2.5 mM (■), 5 mM (●) GSH. (D) A Dixon plot of the cleavage of 0.25 mM (●) or 3 mM (♦) L-GpNA versus GSH concentrations (0 to 5 mM). Data for 0.25 mM L-GpNA is biphasic. (E) Double-reciprocal plot of the initial velocity of the cleavage of L-GpNA in the presence of 0 (○), 5 µM (▼), 10 µM (▲), 20 µM (■), 40 µM (●) GSH. Data shown are average triplicate values±S.D. For many data points the S.D. is smaller than the symbol.

Human GGT (hGGT) can catalyze both a hydrolysis reaction and a transpeptidation reaction. When present at high concentrations, L-amino acids and dipeptides can serve as acceptors in the transpeptidation reaction. GSH has an L-gamma-glutamyl moiety, and the free amino group on the alpha carbon might serve as an acceptor. Our initial studies were designed to clarify whether GSH serves as both a donor substrate and an acceptor. The alpha carbon of D-amino acids is unable to act an acceptor, therefore, the substrate D-GpNA functions as a donor substrate but cannot function as an acceptor [21]. Kinetic analyses of D-GpNA cleavage in the presence of GSH showed that GSH was competitive with D-GpNA. These data reveal that GSH competes for the gamma-glutamyl donor binding site but did not function as an acceptor with a D-gamma-glutamyl donor (FIG. 10A). The $K_m$ of D-GpNA was 160±20 µM. The $K_{is}$ of GSH was 10±1.2 µM. Kinetic analyses were also performed with L-GpNA in the presence of GSH. Analysis of the GSH inhibition of the transpeptidation reaction with L-GpNA and the acceptor GlyGly show that GSH is a noncompetitive inhibitor of both (FIGS. 10B and 10C). The $K_m$ of L-GpNA in the transpeptidation reaction is 1.2±0.1 mM. In the presence of 40 mM GlyGly, GSH inhibits L-GpNA in the transpeptidation reaction with $K_{ii}$=1.70±0.02 mM and $K_{is}$=1.40±0.01 mM. When evaluated with GlyGly in the presence of 3 mM L-GpNA, GSH was a noncompetitive inhibitor of the transpeptidation reaction with $K_{ii}$=3±0.5 mM and $K_{is}$=0.8±0.1 mM (FIG. 10C). This noncompetitive inhibition profile indicates that GSH binds both the free enzyme and the F-form, competing with both the donor (L-GpNA), and the acceptor (GlyGly) substrate when GSH is present at high (millimolar) concentrations.

The interaction between GSH and L-GpNA was then analyzed in the absence of GlyGly. Both GSH and L-GpNA are donor substrates. They both have an L-glutamate as the gamma-glutamyl group and, thus, can also serve as acceptors. The complex data obtained from these experiments were most clearly presented as a Dixon plot (FIG. 10D). Initial velocity analysis of GSH inhibition of the L-GpNA cleavage is shown for two concentrations of L-GpNA (0.25 mM and 3 mM). In the presence of 3 mM L-GpNA, the Dixon plot was linear with GSH acting as a very weak inhibitor of L-GpNA as a donor substrate (FIG. 10D). The $K_m$ of L-GpNA in these studies was 0.83±0.06 mM. The $K_{is}$ of GSH is 0.073±0.006 mM. However, the biphasic nature of the Dixon plot at 0.25 mM L-GpNA indicates GSH has two modes of action under these reaction conditions (FIG. 10D). At concentrations up to 40 µM, GSH is a competitive inhibitor of L-GpNA (FIG. 10E). At concentrations of GSH above 0.31 mM, the Dixon plot shows a second phase, in which GSH is competitive with both L-GpNA as a donor substrate and with L-GpNA as an acceptor. Thus, at high concentrations GSH can act as an acceptor substrate, confirming data from Abbott and colleagues [59]. In the L-Glutamate Release Assay, GSH is used as a substrate over the range of 5-20 µM. Under these conditions GSH is functioning solely as a donor substrate. Therefore, data from the L-Glutamate Release Assay is a direct measurement of the hydrolysis of the gamma-glutamyl bond of glutathione.

Previous studies had shown that OU749 was an uncompetitive inhibitor of hGGT, binding to the gamma-glutamyl-enzyme intermediate (the F-form of the enzyme), while competing with the acceptor in the transpeptidation reaction. A large series of OU749 analogs were analyzed, and their effects on the hydrolysis of the acyl bond of the L-gamma-glutamyl-enzyme intermediate (GSH as substrate), the hydrolysis of the acyl bond of the D-gamma-glutamyl-enzyme intermediate (D-GpNA as a substrate) and the transfer of the L-gamma-glutamyl-enzyme moiety to an acceptor (L-GpNA as the substrate, GlyGly as the acceptor) were evaluated.

OU749 and a series of its analogs of Formula I bearing para-substitutions ($R_8$) on the benzenesulfonamide ring were the first set of compounds that were analyzed (Table 4). All of the compounds were uncompetitive inhibitors of GSH. They were also uncompetitive inhibitors of D-GpNA and L-GpNA, but competitive inhibitors of GlyGly as previously reported for OU749 [14, 53]. Substituting an amine in the para ($R_8$) position increased the potency of inhibition of GSH hydrolysis, while substituting a methyl group at this position decreased the potency. Bulky groups at the para-position also impeded the compound's function as an inhibitor of GSH hydrolysis. A comparison of the inhibition of the hydrolysis of D-GpNA by these same compounds showed that they were more potent inhibitors of the hydrolysis of the D-gamma-glutamyl enzyme acyl bond (D-GpNA substrate) than the L-gamma-glutamyl enzyme acyl bond (GSH substrate), but the rank order of potency remained the same (Table 4). Even though each of these compounds was an uncompetitive inhibitor of L-GpNA in the transpeptidation reaction, their potency correlated more directly with their competitive inhibition of the acceptor GlyGly than their inhibition of the cleavage of the L-gamma-glutamyl acyl bond (GSH hydrolysis). This may be due to the fact that acyl transfer to an acceptor is more rapid than hydrolysis of the acyl bond [30]. Therefore, competing with GlyGly would have a more potent effect on the rate of the reaction than inhibition of hydrolysis of the acyl bond. The methyl-substituted OU749 analog, Compound 2, was previously identified as a more potent inhibitor of hGGT based on its inhibition of the L-GpNA transpeptidation reaction [53]. However, Compound 2 was 1.3-fold less potent than OU749 in inhibiting the hGGT-mediated hydrolysis of GSH, the physiological reaction catalyzed by hGGT (Table 4). In contrast to Compound 2 and the other para-substituted OU749 analogs, Compound 21, with a para-amine, was 3.6-fold more potent than OU749 in inhibiting the catabolism of GSH.

TABLE 4

Inhibition of GGT by compounds represented by Formula I

| Compound # | Substitution | GSH $K_{ii}$ (µM) | D-GpNA $K_{ii}$ (µM) | L-GpNA with GlyGly $K_{ii}$ (µM) | GlyGly with L-GpNA $K_{is}$ (µM) |
|---|---|---|---|---|---|
| 21 | $R_3 = OCH_3$, $R_8 = NH_2$ | $105 \pm 14^a$ | $31 \pm 1$ | $36 \pm 1$ | $10 \pm 1$ |
| 1 (OU749) | $R_3 = OCH_3$ | $376 \pm 50$ | $73 \pm 9^b$ | $68 \pm 6^b$ | $54 \pm 4^b$ |
| 2 | $R_3 = OCH_3$, $R_8 = CH_3$ | $506 \pm 75$ | $73 \pm 4^b$ | $23 \pm 1^b$ | $10 \pm 0.4^b$ |
| 7 | $R_3 = OCH_3$, $R_8 = C(CH_3)_3$ | $NA^a$ | $342 \pm 6^b$ | $150 \pm 13^b$ | $143 \pm 9^b$ |
| 9 | $R_3 = OCH_3$, $R_8 = OCH_3$ | $NA^a$ | $3800 \pm 720^b$ | $149 \pm 23^b$ | $133 \pm 10^b$ |

Compounds are based on Formula I where $R_3 = OCH_3$.
R groups not indicated = H.
Values are ± S.E.
$^a$No GGT inhibition was observed up to 250 µM inhibitor.

Figure 11:
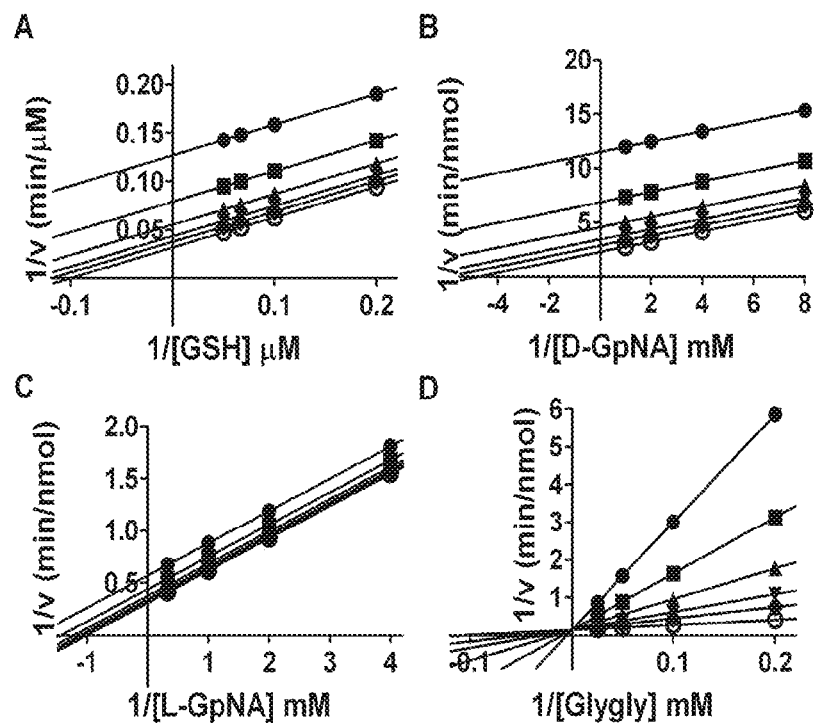
FIG. 11 contains a kinetic analysis of GGT inhibition by Compound 22. (A) Double-reciprocal plot of the initial velocity of the hydrolysis varying GSH or (B) D-GpNA in the presence of 0 (○), 15 mM (♦), 31.25 µM (▼), 62.5 µM (▲), 125 µM (■), 250 µM (●) Compound 22. (C) Double reciprocal plot of the initial velocity of the transpeptidation reaction with varying concentrations of L-GpNA and 40 mM GlyGly or (D) varying concentrations of GlyGly with 3 mM L-GpNA in the presence of 0 (○), 15 mM (♦), 31.25 µM (▼), 62.5 µM (▲), 125 µM (■), 250 µM (●) Compound 22. Data shown are average triplicate values±S.D. For many data points the S.D. is smaller than the symbol.

Based on the improved potency of Compound 21 compared with OU749 in inhibiting the hydrolysis of GSH, a series of structural "$R_8=NH_2$" analogs of the Formula I compound in which the $R_2$ and/or $R_3$ groups of the distal benzene ring was modified (Table 5). All of these compounds were found to be uncompetitive inhibitors of the hydrolysis of GSH, D-GpNA and L-GpNA but competitive inhibitors of GlyGly. The kinetic data for Compound 22 are shown in FIG. 11. As uncompetitive inhibitors, these compounds bind the gamma-glutamyl-enzyme intermediate (F-form) with all three donor substrates. The rank order of potency with which these compounds inhibit the hydrolysis of GSH versus D-GpNA differs (Table 5). These data indicate that there are differences in the F-form of the enzyme dependent on the sterochemistry of the bound glutamate group (L-glutamate in GSH and D-glutamate in D-GpNA) and that these differences affect the potency with which this class of compounds inhibits the reaction. Compound 22 and its analogs are uncompetitive inhibitors of L-GpNA (FIG. 11C). The F-form of the enzyme is the same with either GSH or L-GpNA as substrates, because both have an L-gamma-glutamyl group. However, as observed for the compounds in Table 4, the $K_{ii}$s for this group of compounds with GSH versus L-GpNA as a substrate do not correlate in part as result of L-GpNA binding as an acceptor and perhaps affecting the rate of hydrolysis. The most potent competitive inhibitors of GlyGly (Compounds 29, 22 and 28) are also the most potent inhibitors of the transpeptidation reaction with L-GpNA, again demonstrating the influence of the acceptor on the kinetics of the cleavage of the acyl bond. Among this group of compounds, Compound 22 and Compound 23 were more potent inhibitors of the hydrolysis of GSH by hGGT than the progenitor compound, Compound 21 (Tables 4 and 5). Compound 22 has a methyl group in the para position on the distal benzene ring. Compound 23, has an amine group in the para ($R_3$) position. OU749 analogs with a small neutral or slightly charged group on the distal benzyl ring paired with an amine group para ($R_3$) on the benzenesulfonamide ring are more potent inhibitors of the catabolism of GSH by hGGT than Compound 21.

TABLE 5

Inhibition of human GGT by Compound 21 analogs

| Compound # | Substitution | GSH $K_{ii}$ (µM) | D-GpNA $K_{ii}$ (µM) | L-GpNA with GlyGly $K_{ii}$ (µM) | GlyGly with L-GpNA $K_{is}$ (µM) |
|---|---|---|---|---|---|
| 22 | $R_3 = CH_3$, $R_8 = NH_2$ | $82 \pm 13$ | $31 \pm 1$ | $30 \pm 4$ | $6 \pm 1$ |
| 23 | $R_3 = NH_2$, $R_8 = NH_2$ | $102 \pm 16$ | $29 \pm 3$ | $181 \pm 20$ | $15 \pm 1$ |
| 24 | $R_2 = CH_3$, $R_8 = NH_2$ | $121 \pm 5$ | $109 \pm 4$ | $129 \pm 17$ | $30 \pm 5$ |
| 25 | $R_8 = NH_2$ | $242 \pm 6$ | $58 \pm 6$ | $74 \pm 4$ | $42 \pm 2$ |
| 26 | $R_3 = F$, $R_8 = NH_2$ | $355 \pm 16$ | $24 \pm 2$ | $58 \pm 4$ | $47 \pm 7$ |
| 27 | $R_3 = N(CH_3)_2$, $R_8 = NH_2$ | $363 \pm 35$ | $180 \pm 5$ | $275 \pm 12$ | $24 \pm 4$ |
| 28 | $R_3 = Cl$, $R_8 = NH_2$ | $419 \pm 27$ | $56 \pm 0$ | $54 \pm 1$ | $7 \pm 1$ |
| 29 | $R_2, R_3 = Cl$, $R_8 = NH_2$ | $905 \pm 53$ | $32 \pm 1$ | $34 \pm 4$ | $5 \pm 1$ |

Compounds are based on Formula I where $R_8 = NH_2$.
R groups not indicated = H.
Values are ± S.E.

Figure 12:
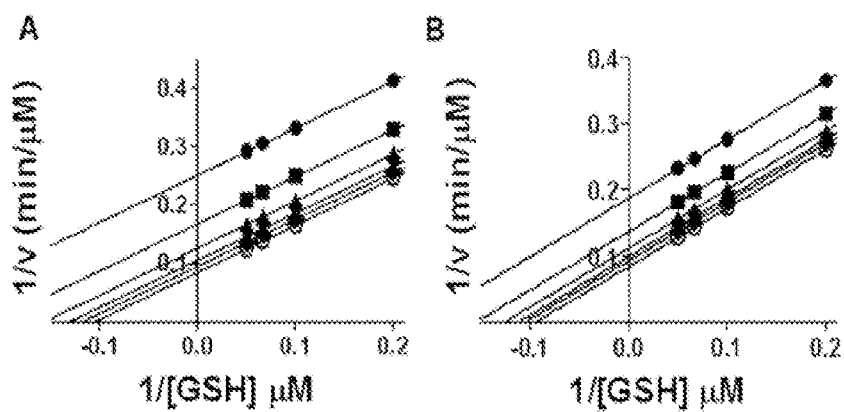
FIG. 12 contains kinetic analyses of GGT inhibition by Compound 3 and Compound 6. Double-reciprocal plots of the initial velocity of the hydrolysis of GSH in the presence of 0 (○), 15 mM (♦), 31.25 µM (▼), 62.5 µM (▲), 125 µM (■), 250 µM (●) Compound 3 (A) or Compound 6 (B). Data shown are average triplicate values±S.D. For many data points the S.D. is smaller than the symbol.

In this example, a series of OU749 analogs with chlorine or benzene substitutions on the sulfobenzene ring were also evaluated as inhibitors of GSH hydrolysis (Table 6). These compounds had previously been evaluated as inhibitors of D-GpNA hydrolysis and the transpeptidation reaction with L-GpNA and had been shown to be potent inhibitors hGGT1 transpeptidation [53]. Compound 3, which has a chlorine in the meta position on the benzenesulfonamide ring, was 5.6-fold more potent than OU749 in inhibiting GSH hydrolysis ($K_{ii}$ 67±6 µM and 376±50 µM, respectively). Interestingly, this same substitution had no effect on the inhibition of the cleavage of D-GpNA relative to that observed for the unsubstituted OU749 core (Compound 3 $K_{ii}$ 75±2 µM and OU749 $K_{ii}$ 73±9 µM). Similar to OU749, all of the compounds in Table 6 were uncompetitive inhibitors of the three donor substrates (GSH, D-GpNA and L-GpNA) and competitive inhibitors of GlyGly. The kinetic data for Compound 3 is shown in FIG. 12. Remarkably, shifting the chlorine substituent to the para position on the benzenesulfonamide ring (Compound 10) virtually abolished the inhibitory potency of the OU749 core structure in the hydrolysis of GSH. This result is in marked contrast to the enhanced GSH inhibition observed when an amine group was substituted at this position (OU749 and Compound 21, Table 4). When chlorine was present at both the meta and para positions, the para chlorine substitution counteracted the enhanced potency gained by a chlorine in the meta position (Compounds 3 and 8, Table 6). Addition and relative placement of the chlorines on the sulfobenzene ring (Table 6: Compounds 3, 4, 8 and 10) had the same relative effect on the hydrolysis of the acyl bond in the D-gamma-glutamyl enzyme intermediate (D-GpNA substrate) as on the L-gamma-glutamyl enzyme intermediate (GSH substrate). However, there was a dramatically different effect of the chlorine substitutions on the transpeptidation reaction. All three compounds with chlorines in the para position were potent inhibitors of the transpeptidation reaction (L-GpNA and GlyGly), while weak to ineffective inhibitors of the hydrolysis of GSH (Table 6: Compounds 4, 8, 10). Compound 3 is the most potent inhibitor of hGGT among all the compounds in Table 6 and among all of the OU749 analogs tested to date.

analogs (FIG. 12). Compound 6, the 1-napthylsulfonamide derivative, was 4-fold more potent than OU749 in inhibiting the catabolism of GSH ($K_{ii}$ 96±2 µM and 376±50 µM, respectively). Compound 30, a 2-napthylsulfonamide derivative, was evaluated to determine whether shifting the bulky, hydrophobic group to a more para position would decrease the potency, as was observed for the chloro-substituted OU749 analogs. Compound 30 was 2.1-fold less potent than Compound 6 in inhibiting the catabolism of GSH (206±37 µM vs 96±2 µM) (Table 6). Compound 30 was also less potent than Compound 6 in inhibiting both hydrolysis and transpeptidation reactions.

Figure 13:
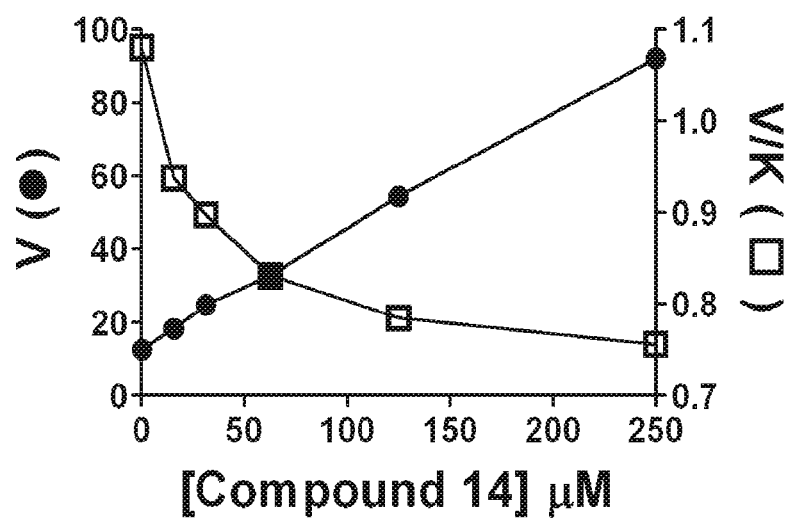
FIG. 13 contains a kinetic analysis of GGT activation of GSH hydrolysis by Compound 14. Initial velocity (V) vs. Compound 14 concentration (closed symbols) and $V/K_m$ of GSH vs. inhibitor concentration (open symbols) plots illustrate that Compound 14 activates GSH hydrolysis as a V-type activator. Data shown are average triplicate values±S.D.

A series of nitro-substituted compounds (11, 13-20) were then evaluated for their effect on the catabolism of GSH by hGGT. Previously, it had been observed that this series of OU749 analogs with a nitro substitution in the para position on the benzenesulfonamide ring were V-type activators of the hydrolysis of D-GpNA and uncompetitive inhibitors of the L-GpNA transpeptidation reaction of hGGT (Table 7, Compounds 11, 13-19) [53]. V-type activators increase the $V_{max}$ of the reaction. Using the L-Glutamate Release Assay, it was discovered that these compounds also accelerated the catabolism of GSH (Table 7). The kinetic analysis of the activation profiles of these compounds revealed that they are V-type activators of the hydrolysis of GSH, as was observed with D-GpNA. The kinetic data for Compound 14 is shown in FIG. 13. The $V_{max}$ increases with increasing concentration of Compound 14. Concomitantly, the $K_m$ of GSH increases to a greater extent than the $V_{max}$. An observed increase in the $V_{max}$ near saturating concentrations of the donor substrate with inhibition of $V/K_m$ correlates with other V-type activators [60]. None of these compounds activated the transpeptidation reaction; instead, they inhibited it (Table 7). If the compounds in Table 7 were accelerating the hydrolysis of GSH by acting as acceptors, a decrease in the rate of

TABLE 6

Inhibition of hGGT by thiadiazol benzenesulfonamide and thiadiazol naphthylsulfonamide compounds

| Compound # | Substitution | GSH $K_{ii}$ (µM) | D-GpNA $K_{ii}$ (µM)$^a$ | L-GpNA with GlyGly $K_{ii}$ (µM) | GlyGly with L-GpNA $K_{is}$ (µM) |
|---|---|---|---|---|---|
| 3 | $R_7$ = Cl, $R_3$ = OCH$_3$ | 67 ± 6 | 75 ± 2 | 22 ± 1 | 12 ± 1 |
| 6 (Formula IIA) | $R_3$ = OCH$_3$ | 96 ± 2 | 161 ± 5 | 75 ± 4 | 46 ± 3 |
| 30 (Formula IIB) | $R_3$ = OCH$_3$ | 206 ± 37 | 415 ± 50 | 364 ± 43 | 143 ± 20 |
| 4 | $R_6$, $R_8$ = Cl; $R_3$ = OCH$_3$ | 950 ± 242 | 76 ± 7 | 16 ± 1 | 4 ± 1 |
| 8 | $R_7$, $R_8$ = Cl; $R_3$ = OCH$_3$ | NA$^a$ | 3160 ± 90 | 18 ± 1 | 11 ± 1 |
| 10 | $R_8$ = Cl, $R_3$ = OCH$_3$ | NA$^a$ | 5530 ± 1460 | 33 ± 1 | 13 ± 1 |

Compounds 3, 4, 8, and 10 are based on Formula I where $R_3$ = OCH$_3$.
Compound 6 is based on Formula IIA where $R_3$ = OCH$_3$.
Compound 30 is based on Formula IIB where $R_3$ = OCH$_3$.
R groups not indicated = H.
Values are ± S.E.
$^a$NO GGT inhibition was observed up to 250 µM inhibitor.

Two compounds (Compounds 6 and 30) containing a bulky, hydrophobic group on the benzenesulfonamide ring were also evaluated as inhibitors of GSH hydrolysis. In these compounds a 1- or 2-napthylsulfonamide ring replaced the benzenesulfonamide ring (Table 6). These compounds are represented by Formulas IIA and IIB of FIGS. 2 and 3, respectively, wherein $R_3$=OCH$_3$. Both compounds inhibited the catabolism of GSH by an uncompetitive mechanism, the same mechanism observed with OU749 and its other glutamate release would be observed in the L-Glutamate Release Assay because glutamate would be converted into a new gamma-glutamyl compound prior to release from the enzyme. The accelerated release of glutamate in the presence of Compound 14 demonstrates that Compound 14 is accelerating the hydrolysis of the acyl-bond and not accelerating the reaction by acting as an acceptor. The potency with which the nitro compounds activate the reaction is similar for both the hydrolysis of GSH and D-GpNA, with only minor discrepancies in the rank order with which they accelerate the reactions (Table 7). These data indicate that the nitro compounds accelerate the hydrolysis of the acyl bond in the F-form of the enzyme with similar potency regardless of whether an L-glutamate or D-glutamate is bound in the F-form of the enzyme. Among the nitro compounds, the only compound that inhibited both the hydrolysis reaction and transpeptidation reaction was Compound 20 (Table 7) [53]. Compound 20 was shown previously to inhibit the hydrolysis of D-GpNA as a competitive inhibitor [53]. In the current analyses, it was found that it is also acted as a competitive inhibitor of the catabolism of GSH (data not shown), indicating this compound binds differently than the other OU749 analogs, competing with the donor substrate binding to the free enzyme.

TABLE 7

Activation of GGT Hydrolysis by thiadiazol benzenesulfonamide compounds

| Cmpd # | Substitution | GSH $K_{Act}$ (μM) | D-GpNA $K_{Act}$ (μM)$^a$ | L-GpNA with GlyGly $K_{ii}$ (μM)$^a$ | GlyGly with L-GpNA $K_{is}$ (μM)$^a$ |
|---|---|---|---|---|---|
| 14 | $R_3, R_8 = NO_2$ | 63 ± 8$^b$ | 52 ± 1 | 133 ± 6 | 81 ± 9 |
| 13 | $R_8 = NO_2$ | 61 ± 8 | 54 ± 3 | 112 ± 6 | 60 ± 4 |
| 15 | $R_2 = Cl$, $R_8 = NO_2$ | 46 ± 8 | 39 ± 1 | 119 ± 7 | 44 ± 8 |
| 11 | $R_3 = OCH_3$, $R_8 = NO_2$ | 41 ± 3 | 37 ± 6 | 93 ± 4 | 96 ± 8 |
| 16 | $R_3 = Cl$, $R_8 = NO_2$ | 34 ± 4 | 31 ± 2 | 62 ± 2 | 44 ± 3 |
| 18 | $R_2 = CH_3$, $R_8 = NO_2$ | 31 ± 7 | 25 ± 1 | 122 ± 9 | 34 ± 1 |
| 17 | $R_3 = CH_3$, $R_8 = NO_2$ | 28 ± 7 | 25 ± 8 | 113 ± 5 | 57 ± 8 |
| 19 | $R_3 = F$, $R_8 = NO_2$ | 28 ± 2 | 22 ± 2 | Slow Onset | 32 ± 1 |

| Cmpd # | Substitution | GSH $K_{ii}$ (μM) | D-GpNA $K_{ii}$ (μM)$^a$ | L-GpNA with GlyGly $K_{ii}$ (μM)$^a$ | GlyGly with L-GpNA $K_{is}$ (μM)$^a$ |
|---|---|---|---|---|---|
| 20$^a$ | $R_2, R_3 = Cl$, $R_8 = NO_2$ | 859 ± 83 | 78 ± 2 | Slow Onset | 10 ± 1 |

Compounds are based on Formula I where $R_8 = NO_2$.
R groups not indicated = H.
Values are ± S.E.
$^a$Compound 20 is a competitive inhibitor of GGT with regard to both the gamma-glutamyl substrate (GSH or D/L-GpNA) and the acceptor GlyGly.

TABLE 8

Toxicity of acivicin and various thiadiazol sulfonamide compounds toward dividing 786-O cells

| Compound | $LD_{50}$ μM |
|---|---|
| Acivicin | 1.3 ± 1.4$^a$ |
| OU749 | 128 ± 0.04 |
| Compound 3 | 382 ± 0.04 |
| Compound 22 | 727 ± 0.02 |
| Compound 6 | 2090 ± 20 |

$^a$Values are $LD_{50}$ ± S.E.

Figure 14:
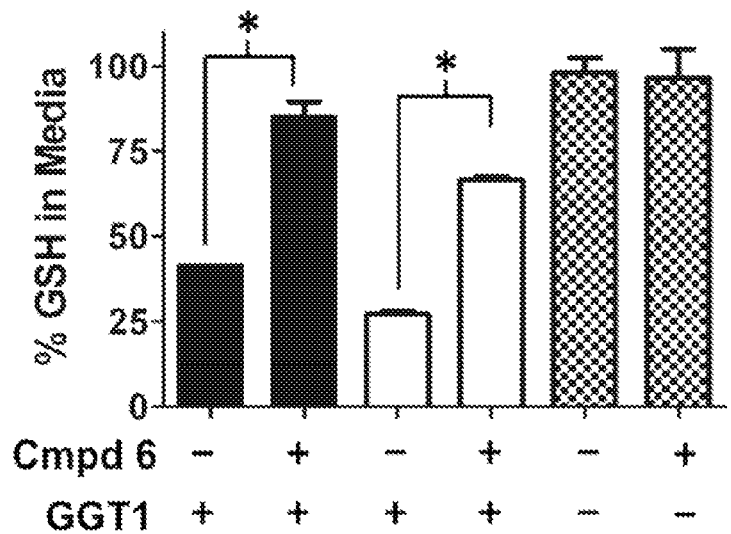
FIG. 14 graphically depicts that Compound 6 (Cmpd 6) inhibits the cleavage of GSH by GGT. GGT-positive 786-O cells (black bars), NIH3T3 cells transfected with human GGT (open bars), and GGT-negative NIH3T3 cells (checkered bars) were incubated in media with 20 µM GSH in the presence or absence 100 µM Compound 6 for one hour. Cleavage of extracellular GSH by GGT, which is expressed on the surface of the cells, was inhibited by Compound 6. Control was media incubated in the absence of cells. Data shown are average duplicate values±S.D. *$p<0.01$ between Compound 6 treated and untreated cells.

All of the kinetic studies were conducted with soluble purified hGGT. To assess inhibition under in vivo conditions, the ability of Compound 6 to inhibit membrane-bound Based on these analyses of hGGT inhibition with a physiological substrate (GSH), three compounds (Compounds 3, 6 and 22) from three distinct classes of OU749 structural derivatives were identified as more potent inhibitors than OU749. To assess their potential clinical utility, the toxicity of these inhibitors towards proliferating cells in culture was evaluated (Table 8). The glutamine analog, acivicin, is a potent inhibitor of hGGT, but it is too toxic for clinical use [52]. The inventors have reported previously that OU749 is less toxic than acivicin [14]. As shown in Table 8, OU749 is almost 100-fold less toxic than acivicin. Data from the current study reveal that, of the three optimized OU749 analogs evaluated, each was considerably less toxic than OU749. The 1-naphthylsulfonamide analog, Compound 6, which was almost four times more potent as an inhibitor of hGGT hydrolysis relative to OU749 ($K_{ii}$ of 96±2 μM vs. 376±50 μM, respectively), was also more than 16-fold less toxic than OU749, with a $LD_{50}$ of 2090±20 μM (Tables 6 and 8).

hGGT expressed on the surface of the hGGT-positive cell line, 786-0, was evaluated. The rate of cleavage of 20 μM GSH was measured by determining the concentration of GSH remaining in the media after one hour in the presence or absence of Compound 6 (FIG. 14). Compound 6 (100 μM) blocked the hGGT catabolism of GSH by 51% (FIG. 14). To confirm that the reduced catabolism of GSH was due to inhibition of hGGT, the experiment was repeated using a stably transfected hGGT-positive cell line (NIH3T3$^{GGT}$) and its GGT-negative parental line (NIH3T3). The control GGT-negative NIH3T3 cells were unable to metabolize extracellular GSH (FIG. 14). Constitutive expression of hGGT in NIH3T3$^{GGT}$ cells resulted in a dramatic increase in the cleavage of extracellular GSH (FIG. 14). Compound 6 reduced the ability of NIH3T3$^{GGT}$ to metabolize GSH in the media by 59%, demonstrating that this powerful new inhibitor is capable of efficiently blocking hGGT's enzymatic activity in its cellular context.

Discussion—Study II

To develop potent inhibitors of hGGT that can be used clinically, it is desirable to evaluate the compounds as inhibitors of the physiological hGGT reaction. This can now be performed with GSH as the substrate in our L-Glutamate Release Assay. GSH is the most abundant substrate of hGGT in vivo. The L-Glutamate Release Assay allows for kinetic analysis of compounds as inhibitors of hGGT-mediated GSH catabolism. Most studies of hGGT inhibition have been conducted using the L-GpNA transpeptidation assay with millimolar concentrations of the synthetic gamma-glutamyl donor substrate (L-GpNA) and the acceptor (GlyGly). Screening the analogs of OU749 in this study with the transpeptidation assay would have identified Compounds 2-4 and 8 as particularly potent inhibitors. However, the present analysis of their inhibition of the hydrolysis of GSH showed that Compounds 2, 4, and 8 were much less potent than OU479. In fact, Compound 8 had no detectible inhibitory activity towards the hydrolysis of GSH. In contrast, Compounds 3, 6, 21-25 and 30 were more potent inhibitors than OU749 of the physiologic reaction catalyzed by hGGT. These data illustrate that the use of synthetic substrates like D- and L-GpNA can result in the misdirected optimization of weak inhibitors of the physiological hGGT GSH reaction.

Compounds assessed in this study had various effects on the catabolism of GSH. There was no consistent correlation between the effect of a compound on the catabolism of GSH and its effect on the hydrolysis of D-GpNA or on the transpeptidation reaction with L-GpNA as the substrate and GlyGly as the acceptor. There are features of each of the three assays which provided unique insights into the mechanism by which these uncompetitive inhibitors alter the rate of the hGGT reaction. The results presented here show that at the physiological concentrations of GSH used in the L-Glutamate Release Assay, the reaction catalyzed by hGGT is the hydrolysis of the gamma-glutamyl bond of GSH. The gamma-glutamyl enzyme intermediate has an L-glutamate in the active site bound by an acyl bond to the oxygen on the side chain of Thr 381 [30]. Free glutamate is detected when it is released as the second product of the reaction. In the assay measuring the hydrolysis of D-GpNA, there is a D-gamma-glutamyl enzyme intermediate. In assays with either L- or D-GpNA as substrates, the release of p-NA is the product that is quantifiably measured. Use of L-GpNA and GlyGly as the donor and acceptor substrates, respectively, results in a transpeptidation reaction, with the production of a gamma-glutamyl-acceptor compound as the second product. This assay provides insight into the interaction of the test compound with the acceptor binding site. Therefore, data from a L-GpNA transpeptidation reaction can serve a complementary role with data from a GSH hydrolysis reaction to provide information regarding the relative contribution of the acceptor in accelerating acyl transfer or trapping the acyl-enzyme intermediate by the uncompetitive inhibitor.

In a previous report describing OU749 as an inhibitor of hGGT, it was demonstrated that it acts an uncompetitive inhibitor of the transpeptidation reaction with L-GpNA as a substrate, binding the F-form of the enzyme and competing with the acceptor GlyGly [14]. With the exception of Compounds 19 and 20, all of the OU749 analogs evaluated in this study showed the same mechanism of inhibition of the transpeptidation reaction.

A primary goal has been to identify potent analogs of OU749 as inhibitors of GSH hydrolysis. OU749 is a weaker inhibitor of hydrolysis of the acyl bond of the gamma-glutamyl enzyme intermediate when GSH is the substrate and an L-gamma-glutamyl group occupies the donor site than when D-GpNA is the substrate and a D-gamma-glutamyl group occupies the active site (OU749, Table 4). In the first set of compounds analyzed, addition of substituents in the para position on the sulfobenzene ring showed that an amine group enhanced the potency of OU749 as an inhibitor of GSH hydrolysis, while the addition of bulky, uncharged groups reduced its potency. Further analysis of modifications to the benzenesulfonamide ring (Table 6) showed that chlorine in the meta position (Compound 3) is preferential to a chlorine in the para (Compound 10), para and ortho (Compound 4), or para and meta positions (Compound 8). The chlorine in the para position could be eliciting an electrostatic repulsion with a charged amino acid or dipoles with the within the active site, thereby diminishing the affinity of the OU749 analog and its inhibitory potency. The compounds had the same rank order of potency with which they inhibited GSH and D-GpNA hydrolysis, demonstrating that, while substituents in the para position do not change the orientation of the compound relative to the acyl bond, they may either alter the affinity with which the compounds bind the enzyme or alter the electrophilicity of the sulfonamide group. Han and colleagues synthesized and evaluated a series of gamma-glutamyl phosphono diesters as inhibitors of hGGT [19]. They proposed that the mechanism of inhibition by these compounds included the phosphonate diesters reacting covalently with the catalytic Thr residue of GGT. Without wishing to be bound by theory, it is proposed that the sulfonamide of the present compounds interact electrostatically with the acyl bond of the gamma-glutamyl-enzyme intermediate. Modifications to the sulfobenzene rings, such as addition of chlorines or a benzyl group (Table 6) may act by altering alter the strength of interaction between the sulfonamide and the catalytic nucleophile of hGGT and/or the acyl bond.

The conversion of the benzenesulfonamide moiety to a naphthylsulfonamide moiety (Formulas IIA and IIB) not only altered the potency of the compounds but also elicited different effects on the hydrolysis of GSH versus D-GpNA (Table 6). Addition of benzene in the ortho position (1-naphthylsulfonamide ring, Compound 6) or in the meta position (2-naphthylsulfonamide ring, Compound 30) enhanced the inhibition of GSH hydrolysis yet reduced the inhibition of D-GpNA hydrolysis relative to OU749.

Addition of a para-nitro on the benzenesulfonamide ring resulted in a compound that accelerated the hydrolysis reaction but inhibited the transpeptidation reaction (Table 7). In the transpeptidation reaction, GlyGly accelerates acyl transfer of the gamma-glutamyl group to the free amine of GlyGly. Therefore, in the transpeptidation reaction OU749 analogs inhibit the transpeptidation reaction by two mechanisms: blocking GlyGly from the acceptor site and limiting access to the L-gamma-glutamyl acyl bond. One possible explanation for this effect is that the nitro-substituted OU749 analogs bind to the GlyGly site, inhibiting the transpeptidation reaction and destabilizing the acyl-bond to allow a more facile attack by water, thus promoting hydrolysis. The inventors have previously shown that GlyGly increases the L-GpNA cleavage rate by 22-fold [53]. Addition of a para nitro OU749 analog increased the D-GpNA cleavage rate by only 5-fold [53]. This difference in the rate of acceleration of hydrolysis of the acyl bond, which is observed with GSH and D-GpNA, is insufficient to offset the decreased rate of cleavage of L-GpNA due to the absence of GlyGly, resulting in an apparent inhibition of the transpeptidation reaction. All of the inhibitors and the activators are competitive inhibitors of GlyGly in the transpeptidation reaction, indicating that the inhibitors are binding at the acceptor site or at a site that overlaps with the acceptor site, thus blocking GlyGly from binding.

Modifications to the distal benzene ring of OU749 decreased the $K_{is}$ up to 11-fold as competitive inhibitors of GlyGly (Compound 29, Table 5). Two of the most potent inhibitors of GlyGly bear chlorines in the para position (Compound 28) or the meta and para positions (Compound 29). However, there was no correlation between the potency of these compounds as competitive inhibitors of GlyGly and their potency of inhibiting the hydrolysis of GSH. The effect of modifications to the distal benzene ring of the amine OU749 structural analogs on the inhibition of hydrolysis of GSH was analyzed. The data revealed that a small neutral (Compound 22 and Compound 24), small positive (electron donating, Compound 23), or small slightly negatively charged group (Compound 21) on the distal benzene ring was favorable for hGGT inhibition, whereas a bulky group (Compounds 26-29) on the distal benzene ring tended to diminish the inhibitory potency of the amine OU749 analogs (Table 5).

The toxicity of the OU749 analogs was not related to their potency as inhibitors of hGGT activity. Inhibitors of GGT that are glutamine analogs not only inhibit hGGT, but also inhibit other glutamine-dependent enzymes, which leads to the neurotoxicity observed with acivicin [52, 62, 63]. OU749 is not a glutamine analog and has been shown to be less toxic than acivicin [14]. The present work has identified potent inhibitors that are even less toxic than OU749. Compound 3 was the most potent hGGT inhibitor and was 3-fold less cytotoxic than OU749 with a $LD_{50}$ of 382 μM (Table 8). Compound 6 was the third most potent hGGT inhibitor (approximately four-fold more potent than OU749) and exhibited the least cytotoxicity with a $LD_{50}$ of approximately 2100 μM (Table 8).

The ability to measure inhibition of the extracellular catabolism of GSH by hGGT is valuable for inhibitor optimization, as the physiologic reaction is the hydrolysis of GSH on the cell surface. The most potent and least cytotoxic benzylthiadiazol sulfonamide analog, Compound 6, was also found to inhibit hGGT in vivo, blocking the cleavage of extracellular GSH.

Although the presently described inventive concept(s) and its advantages have been described in detail, it should be understood that various changes, substitutions and alterations can be made herein without departing from the spirit and scope of the presently described inventive concept(s) as defined in the appended claims. Moreover, the scope of the presently described inventive concept(s) is not intended to be limited to the particular embodiments of the process, items of manufacture, compositions of matter, means, methods and steps described in the specification. As one of ordinary skill in the art will readily appreciate from the present disclosure, processes, items of manufacture, compositions of matter, means, methods, or steps, presently existing or later to be developed that perform substantially the same function or achieve substantially the same result as the corresponding embodiments described herein may be utilized according to the presently described inventive concept(s). Accordingly, the appended claims are intended to include within their scope such processes, items of manufacture, compositions of matter, means, methods, or steps.

REFERENCES

The following references, to the extent that they provide exemplary procedural or other details supplementary to those set forth herein, are specifically incorporated herein by reference.

1. Hanigan, M. H. (1998) *Chem Biol Interact* 111-112, 333-342.
2. Hanigan, M. H., and Frierson, H. F., Jr. (1996) *J Histochem Cytochem* 44, 1101-1108.
3. Lieberman, M. W., Wiseman, A. L., Shi, Z. Z., Carter, B. Z., Barrios, R., Ou, C. N., Chevez-Barrios, P., Wang, Y., Habib, G. M., Goodman, J. C., Huang, S. L., Lebovitz, R. M., and Matzuk, M. M. (1996) *Proc Natl Acad Sci USA* 93, 7923-7926.
4. Hanigan, M. H., Frierson, H. F., Jr., Swanson, P. E., and De Young, B. R. (1999) *Hum Pathol* 30, 300-305.
5. Ruoso, P., and Hedley, D. W. (2004) *Cancer Chemother Pharmacol* 54, 49-56.
6. Hanigan, M. H., Gallagher, B. C., Townsend, D. M., and Gabarra, V. (1999) *Carcinogenesis* 20, 553-559.
7. Hanigan, M. H., and Pitot, H. C. (1985) *Carcinogenesis* 6, 165-172.
8. Lowry, M. H., McAllister, B. P., Jean, J. C., Brown, L. A., Hughey, R. P., Cruikshank, W. W., Amar, S., Lucey, E. C., Braun, K., Johnson, P., Wight, T. N., and Joyce-Brady, M. (2008) *Am J Respir Cell Mol Biol* 38, 509-516.
9. Ahluwalia, G. S., Grem, J. L., Hao, Z., and Cooney, D. A. (1990) *Pharmacol Ther* 46, 243-271.
10. Weiss, G. R., McGovren, J. P., Schade, D., and Kufe, D. W. (1982) *Cancer Res* 42, 3892-3895.
11. Earhart, R. H., Koeller, J. M., Davis, T. E., Borden, E. C., McGovren, J. P., Davis, H. L., and Tormey, D. C. (1983) *Cancer Treat Rep* 67, 683-692.
12. Fleishman, G., Yap, H. Y., Murphy, W. K., and Bodey, G. (1983) *Cancer Treat Rep* 67, 843-844.
13. Taylor, S., Belt, R. J., Joseph, U., Haas, C. D., and Hoogstraten, B. (1984) *Invest New Drugs* 2, 311-314.
14. King, J. B., West, M. B., Cook, P. F., and Hanigan, M. H. (2009) *J Biol Chem* 284, 9059-9065.
15. Tate, S. S., and Meister, A. (1974) *J Biol Chem* 249, 7593-7602.
16. Tate, S. S., and Meister, A. (1974) *Proc Natl Acad Sci USA* 71, 3329-3333.
17. Castonguay, R., Lherbet, C., and Keillor, J. W. (2003) *Biochemistry* 42, 11504-11513.
18. Keillor, J. W., Castonguay, R., and Lherbet, C. (2005) *Methods Enzymol* 401, 449-467.
19. Han, L., Hiratake, J., Kamiyama, A., and Sakata, K. (2007) *Biochemistry* 46, 1432-1447.
20. Lherbet, C., and Keillor, J. W. (2004) *Org Biomol Chem* 2, 238-245.
21. Thompson, G. A., and Meister, A. (1976) *Biochem Biophys Res Commun* 71, 32-36.
22. Elce, J. S., and Broxmeyer, B. (1976) *Biochem J* 153, 223-232.
23. Curthoys, N. P., and Hughey, R. P. (1979) *Enzyme* 24, 383-403.
24. Allison, R. D., and Meister, A. (1981) *J Biol Chem* 256, 2988-2992.
25. Cook, P. F., and Cleland, W. W. (2007) *Enzyme kinetics and mechanism*, Garland Science, London; New York.
26. Allison, R. D. (1985) gamma-Glutamyl transpeptidase: kinetics and mechanism, *Methods Enzymol* 113, 419-437.
27. Stole, E., Smith, T. K., Manning, J. M., and Meister, A. (1994) *J Biol Chem* 269, 21435-21439.
28. Smith, T. K., Ikeda, Y., Fujii, J., Taniguchi, N., and Meister, A. (1995) *Proc Natl Acad Sci U S A* 92, 2360-2364.
29. Ikeda, Y., Fujii, J., Anderson, M. E., Taniguchi, N., and Meister, A. (1995) *J Biol Chem* 270, 22223-22228.

30. Castonguay, R., Halim, D., Morin, M., Furtos, A., Lherbet, C., Bonneil, E., Thibault, P., and Keillor, J. W. (2007) *Biochemistry* 46, 12253-12262.
31. Thompson, G. A., and Meister, A. (1979) *J Biol Chem* 254, 2956-2960.
32. Tate, S. S., and Meister, A. (1978) *Proc Natl Acad Sci USA* 75, 4806-4809.
33. Okada, T., Suzuki, H., Wada, K., Kumagai, H., and Fukuyama, K. (2006) *Proc Natl Acad Sci USA* 103, 6471-6476.
34. Wada, K., We, M., Suzuki, H., and Fukuyama, K. (2010) *FEBS J* 277, 1000-1009.
35. Morrow, A. L., Williams, K., Sand, A., Boanca, G., and Barycki, J. J. (2007) *Biochemistry* 46, 13407-13414.
36. Ikeda, Y., Fujii, J., Taniguchi, N., and Meister, A. (1995) *J Biol Chem* 270, 12471-12475.
37. Hanigan, M. H., and Ricketts, W. A. (1993) *Biochemistry* 32, 6302-6306.
38. Estrela, J. M., Ortega, A., and Obrador, E. (2006) *Crit. Rev Clin Lab Sci* 43, 143-181.
39. Perry, R. R., Mazetta, J. A., Levin, M., and Barranco, S. C. (1993) *Cancer* 72, 783-787.
40. Oberli-Schrammli, A. E., Joncourt, F., Stadler, M., Alternatt, H. J., Buser, K., R is, H. B.,
Schmid, U., and Cerny, T. (1994) *Intl Cancer* 59, 629-636.
41. Joncourt, F., Oberli-Schrammli, A. E., Stadler, M., Buser, K., Franscini, L., Fey, M. F., and Cerny, T. (1995) *Leuk Lymphoma* 17, 101-109.
42. Raderer, M., and Scheithauer, W. (1993) *Cancer* 72, 3553-3563.
43. Mulder, T. P., Manni, J. J., Roelofs, H. M., Peters, W. H., and Wiersma, A. (1995) *Carcinogenesis* 16, 619-624.
44. Mena, S., Benlloch, M., Ortega, A., Carretero, J., Obrador, E., Asensi, M., Petschen, I.,
Brown, B. D., and Estrela, J. M. (2007) *Clin Cancer Res* 13, 2658-2666.
45. Rudin, C. M., Yang, Z., Schumaker, L. M., VanderWeele, D. J., Newkirk, K., Egorin, M. J., Zuhowski, E. G., and Cullen, K. J. (2003) *Cancer Res* 63, 312-318.
46. Wickham, S., West, M. B., Cook, P. F. and Hanigan, M. H. (2011) Anal. Biochem. 414, 208-214.
47. Rojas, E., Valverde, M., Kala, S. V., Kala, G. and Lieberman, M. W. (2000) Mutat. Res. 447, 305-316
48. Hanigan, M. H., Gallagher, B. C., Taylor, P. T., Jr. and Large, M. K. (1994) |Cancer Res. 54, 5925-5929
49. Anders, M. W. (2008) Chem. Res. Toxicol. 21, 145-159
50. Singh, R. K., Gupta, S., Dastidar, S, and Ray, A. (2010) Pharmacology. 85, 336-349
51. Lee, D. S., Evans, J. C., Robins, S. J., Wilson, P. W., Albano, I., Fox, C. S., Wang, T. J., Benjamin, E. J., D'Agostino, R. B. and Vasan, R. S. (2007) Arterioscler. Thromb. Vasc. Biol. 27, 127-133
52. Hidalgo, M., Rodriguez, G., Kuhn, J. G., Brown, T., Weiss, G., MacGovren, J. P., Von Hoff, D. D. and Rowinsky, E. K. (1998) Clin. Cancer Res. 4, 2763-2770
53. Wickham, S., Regan, N., West, M. B., Kumar, V. P., That, J., Li, P. K., Cook, P. F. and Hanigan, M. H. (2012) J. Enzyme Inhib. Med. Chem. 27, 476-489
54. Meister, A., Tate, S. S, and Griffith, O. W. (1981) Methods Enzymol. 77, 237-253
55. Tietze, F. (1969) Anal. Biochem. 27, 502-522
56. Hansen, M. B., Nielsen, S. E. and Berg, K. (1989) J. Immunol. Methods. 119, 203-210
57. West, M. B., Wickham, S., Quinalty, L. M., Pavlovicz, R. E., Li, C. and Hanigan, M. H. (2011) J. Biol. Chem. 286, 28876-28888
58. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T. and Warren, G. L. (1998) Acta Crystallogr. D Biol. Crystallogr. 54, 905-921
59. Abbott, W. A., Griffith, O. W. and Meister, A. (1986) J. Biol. Chem. 261, 13657-13661
60. Reinhart, G. D. (2004) Methods Enzymol. 380, 187-203
61. Hu, X., Legler, P. M., Khavrutskii, I., Scorpio, A., Compton, J. R., Robertson, K. L., Friedlander, A. M. and Wallqvist, A. (2012) Biochemistry. 51, 1199-1212
62. Sebolt, J. S., Aoki, T., Eble, J. N., Glover, J. L. and Weber, G. (1985) Biochem. Pharmacol. 34, 97-100
63. Chittur, S. V., Klem, T. J., Shafer, C. M. and Davisson, V. J. (2001) Biochemistry. 40, 876-887

What is claimed is:

1. A method of inhibiting the activity of gamma-glutamyl transpeptidase (GGT), the method comprising the steps of:
   obtaining a compound as represented by Formula (IIA), or a pharmaceutically acceptable salt thereof:

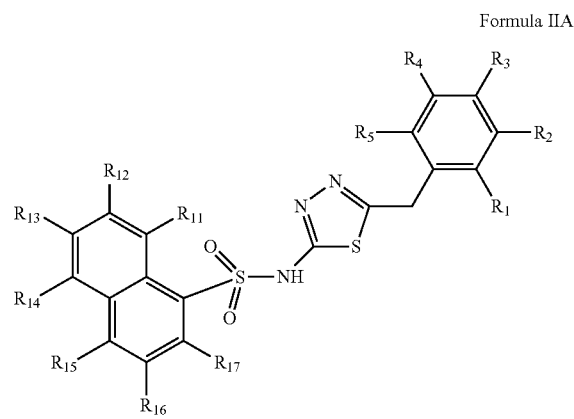

Formula IIA wherein $R_1$-$R_5$ and $R_{11}$-$R_{17}$ are the same or different from each other, and wherein each of $R_1$-$R_5$ and $R_{11}$-$R_{17}$ is selected from the group consisting of H, Cl, F, Br, I, OH, an alkoxy, and $NO_2$; and
   exposing the GGT to the compound, thereby inhibiting activity of the GGT.

2. The method of claim 1, wherein the alkoxy of Formula (IIA) of the compound is selected from the group consisting of methoxy, ethoxy, n-propoxy, iso-propoxy, n-butoxy, tert-butoxy, sec-butoxy, pentoxy, hexoxy, octoxy, nonoxy, decoxy, undecoxy, and dodecoxy.

3. The method of claim 1, wherein at least one of $R_1$-$R_5$ and $R_{11}$-$R_{17}$ of Formula (IIA) of the compound is Cl.

4. The method of claim 1, wherein at least one of $R_1$-$R_5$ and $R_{11}$-$R_{17}$ of Formula (IIA) of the compound is an alkoxy group.

5. The method of claim 4, wherein the alkoxy group is a methoxy group or an ethoxy group.

6. The method of claim 1, wherein $R_3$ of Formula (IIA) of the compound is an alkoxy group, and wherein each of $R_1$, $R_2$, $R_4$, $R_5$ and $R_{11}$-$R_{17}$ is H.

7. The method of claim 6, wherein $R_3$ is a methoxy group.

8. The method of claim 1, wherein $R_3$ of Formula (IIA) of the compound is an alkoxy group, and wherein at least one of $R_1$, $R_2$, $R_4$, $R_5$ and $R_{11}$-$R_{17}$ is Cl.

9. The method of claim 8, wherein $R_3$ of Formula (IIA) of the compound is a methoxy group.

10. The method of claim 1, wherein at least one of $R_1$-$R_5$ of Formula (IIA) of the compound is a methoxy group.

11. The method of claim 1, wherein the GGT is inhibited in vivo.

12. The method of claim 1, wherein the GGT is inhibited in vitro.

13. A compound represented by Formula (IIA) or a pharmaceutically acceptable salt thereof;

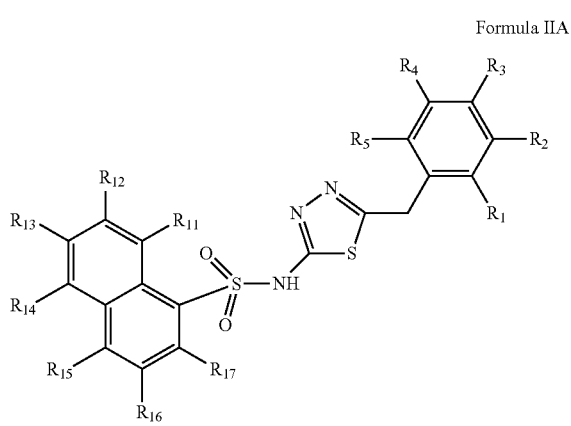

Formula IIA wherein $R_1$-$R_5$ and $R_{11}$-$R_{17}$ are the same or different from each other, and wherein each of $R_1$-$R_5$ and $R_{11}$-$R_{12}$ is selected from the group consisting of H, Cl, F, Br, I, OH, an alkoxy, and $NO_2$; and wherein the compound is effective in inhibiting gamma-glutamyl transpeptidase (GGT).

14. The compound of claim 13, wherein the alkoxy of Formula (IIA) is selected from the group consisting of methoxy, ethoxy, n-propoxy, iso-propoxy, n-butoxy, tert-butoxy, sec-butoxy, pentoxy, hexoxy, octoxy, nonoxy, decoxy, undecoxy, and dodecoxy.

15. The compound of claim 13, wherein at least one of $R_1$-$R_5$ and $R_{11}$-$R_{17}$ is Cl.

16. The compound of claim 13, wherein at least one of $R_1$-$R_5$ and $R_{11}$-$R_{17}$ is an alkoxy group.

17. The compound of claim 16, wherein the alkoxy group is a methoxy group or an ethoxy group.

18. The compound of claim 13, wherein $R_3$ is an alkoxy group, and each of $R_1$, $R_2$, $R_4$, $R_5$ and $R_{11}$-$R_{17}$ is H.

19. The compound of claim 18, wherein $R_3$ is a methoxy group.

20. The compound of claim 13, wherein $R_3$ is an alkoxy group, and at least one of $R_1$, $R_2$, $R_4$, $R_5$ and $R_{11}$-$R_{17}$ is Cl.

21. The compound of claim 20, wherein $R_3$ is a methoxy group.

22. The compound of claim 13, wherein at least one of $R_1$-$R_5$ is a methoxy group.

23. A pharmaceutical composition comprising the compound of claim 13 and a pharmaceutically-acceptable carrier.

* * * * *

UNITED STATES PATENT AND TRADEMARK OFFICE
CERTIFICATE OF CORRECTION

PATENT NO. : 9,540,337 B2
APPLICATION NO. : 13/974704
DATED : January 10, 2017
INVENTOR(S) : Marie H. Hanigan and Pui Kai Li It is certified that error appears in the above-identified patent and that said Letters Patent is hereby corrected as shown below:

In the Specification
Column 16, Line 14: After "oil" delete "1131;" and replace with -- I 131; --
Column 16, Line 19: Delete "fluorocitabine," and replace with -- flurocitabine, --
Column 32, Line 30: After "Cell Lines:" delete "786-0" and replace with -- 786-O --
Column 32, Line 48: After "Assays:" delete "786-0" and replace with -- 786-O --
Column 32, Line 58: Delete "786-0" and replace with -- 786-O --
Column 36, Line 13: Before "relative" insert -- $K_{ii}$ --
Column 48, Line 48: Delete "786-0," and replace with -- 786-O, --
Column 53, Line 11: After "Wada, K.," delete "We," and replace with -- Irie --
Column 53, Line 25: Delete "Alternatt," and replace with -- Altermatt, --
Column 53, Line 25: Delete "R is," and replace with -- Ris, --
Column 53, Line 26: Delete "Intl Cancer" and replace with -- Int J Cancer --
Column 53, Line 57: After "Kumar, V.P.," delete "That," and replace with -- Thai, --

Signed and Sealed this
Twenty-eighth Day of February, 2017

Michelle K. Lee
*Director of the United States Patent and Trademark Office*